(12) United States Patent
Hogaboam et al.

(10) Patent No.: US 8,795,668 B2
(45) Date of Patent: Aug. 5, 2014

(54) METHODS FOR TREATING PULMONARY FIBROSIS

(75) Inventors: Cory M. Hogaboam, Ann Arbor, MI (US); Steven L. Kunkel, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 631 days.

(21) Appl. No.: 11/641,465

(22) Filed: Dec. 18, 2006

(65) Prior Publication Data

US 2007/0172856 A1    Jul. 26, 2007

Related U.S. Application Data

(60) Provisional application No. 60/753,647, filed on Dec. 23, 2005.

(51) Int. Cl.
*A61K 39/395* (2006.01)

(52) U.S. Cl.
USPC .................................. 424/152.1; 424/130.1

(58) Field of Classification Search
CPC ................... A61K 2300/00; A61K 2309/505; C07K 16/2863; C07K 16/2866; C07K 231/24
See application file for complete search history.

(56) References Cited

U.S. PATENT DOCUMENTS

| | | | | |
|---|---|---|---|---|
| 2003/0003576 A1* | 1/2003 | Abe et al. | ...................... | 435/372 |
| 2005/0238620 A1 | 10/2005 | Gomer et al. | | |
| 2005/0244888 A1 | 11/2005 | Li et al. | | |

OTHER PUBLICATIONS

Garantziotis et al. Journal of Clinical Investigation 2004, 114:319-321.*
Abid et al. Current Opinion in Oncology 2001, 13:242-248.*
Baulcombe, "RNA as a target and an initiator of post-transcriptional gene silencing in transgenic plants," Plant Mol. Biol. 32:79 (1996).
Bonacchi et al., "The Chemokine CCL21 Modulates Lymphocyte Recruitment and Fibrosis in Chronic Hepatitis C," Gastroenterology, 2003, 125:1060-1076.
Bucala et al., "Circulating Fibrocytes Define a New Leukocyte Subpopulation That Mediates Tissue Repair" Mol. Med., 1:71-81 (1994).
Choi et al., "Focal interstitial CC chemokine receptor 7 (CCR7) expression in idiopathic interstitial pneumonia," J. Clin. Pathol. 59:28-39 (2006).
Cogoni et al., "Suppression of Gene Expression by Homologous Transgenes," Antonie Van Leeuwenhoek 65:205 (1994).
Crouch, "Pathobiology of pulmonary fibrosis," Am. J. Physiol. Lung Cell. Mol. Physiol. 259:L159-L184 (1990).
Flaherty et al., "Steroids in Idiopathic Pulmonary Fibrosis: A Propsective Assessment of Adverse Reactions, Response to Therapy, and Survival," Am. J. Med. 110:278-282 (2001).
Flaherty et al., "Radiological versus histological diagnosis in UIP and NSIP: survival implications," Thorax, 58:143-148 (2003).
Flaherty et al., "The role of pulmonary function testing in pulmonary fibrosis," Curr. Opin. Pulm. Med., 6:404-410 (2000).
Gharee-Kermani et al., "Animal Models of Pulmonary Fibrosis," Meths. Mol. Med., 2005, 117:251-259.
Ghobrial et al., "Expression of the Chemokine Receptors $CXCR_4$ and $CCR_7$ and Disease Progression in B-Cell Chronic Lymphocytic Leukemia/Small Lymphocytic Lymphoma," Mayo Clin. Proc. 79:318-325 (2004).
Hampton et al., "Mortality in Idiopathic Pulmonary Fibrosis (IPF):Predictors Prior to High Dose Corticosteroid Therapy," Am. J. Respir. Crit. Care Med., 149:A878 (1994).
Hogaboam et al., "Dynamic Interactions Between Lung Fibroblasts and Leukocytes: Implications for Fibrotic Lung Disease," Proc. Assoc. Am. Physicians, 110:313-320 (1998).
Hogaboam et al., "Approaches to Evaluation of Fibrogenic Pathways in Surgical Lung Biopsy Specimens," Meths. Mol. Med., 117:209-221 (2005).
Kapanci et al., "Cytoskeletal protein modulation in pulmonary alveolar myofibroblasts during idiopathic pulmonary fibrosis. Possible role of transforming growth factor beta and tumor necrosis factor alpha," Am. J. Respir. Crit. Care Med., 152:2163-2169 (1995).
Kazerooni et al., "Thin-Section CT Obtained at 10-mm Increments versus Limited Three-Level Thin-Section CT for Idiopathic Pulmonary Fibrosis: Correlation with Pathologic Scoring," AJR Am. J. Roentgenol., 169:977-983 (1997).
Keane et al., "The CXC Chemokines, IL-8 and IP-10, Regulate Angiogenic Activity in Idiopathic Pulmonary Fibrosis," J. Immunol., 159(3):1437-1443 (1997).
Kennerdell, "Use of dsRNA-Mediated Genetic Interference to Demonstrate that frizzled and frizzled 2 Act in the Wingless Pathway," Cell 95:1017-1026 (1998).
Lynch et al., "Corticosteroids in idiopathic pulmonary fibrosis," Curr. Opin. Pulm. Med 7:298-308 (2001).
Martinez et al., "Increased expression of the interleukin-10 gene by alveolar machrophages in interstitial lung disease," Am. J. Physiol., 273:L676-683 (1997).
Mauch "Matrix Metalloproteinase-19: What Role Does this Enzyme Play in Wound Healing?," J. Invest. Dermatol. 2003, 121.
Murakami et al., "Chemokine receptors and melanoma metastasis," J. Dermatol. Sci., 36:71-78 (2004).
Pardo et al., "Up-Regulation and Profibrotic Role of Osteopontin in Human Idiopathic Pulmonary Fibrosis," PLoS Med 2005, 2e251.
Puxeddu et al., "The CC chemokine eotaxin/CCL11 has a selective profibrogenic effect on human lung fibroblasts,"J. Allergy Clin. Immunol., 117(1):103-110 (2006).
Ryu et al., "Idiopathic Pulmonary Fibrosis: Current Concepts," Mayo Clin. Proc. 73:1085-1101 (1998).
Sallusto et al., "Rapid and coordinated switch in chemokine receptor expression during dendritic cell maturation," Eur. J. Immunol., 28:2760-2769 (1998).
Sallusto et al., "Distinct patterns and kinetics of chemokine production regulate dendritic cell function," Eur. J. Immunol., 29:1617-1625 (1999).

(Continued)

*Primary Examiner* — Sharon Wen
(74) *Attorney, Agent, or Firm* — Marshall, Gerstein & Borun LLP

(57) ABSTRACT

Methods and compositions for the treatment of fibrosing diseases are described. More specifically, the invention demonstrates that inhibiting or otherwise decreasing the activity of CCL21 either alone or in combination with CCL19 will be effective in reducing the presence of fibrotic lesions and ameliorating the symptoms of fibrosing disorders.

23 Claims, 16 Drawing Sheets

(56) References Cited

OTHER PUBLICATIONS

Suganuma et al., "Enhanced migration of fibroblasts derived from lungs with fibrotic lesions," Thorax, 50:984-989 (1995).
Travis et al., "Idiopathic Nonspecific Interstitial Pneumonia: Prognostic Significance of Cellular and Fibrosing Patterns," Am. J. Surg. Path., 24:19-33 (2000).
Van Den Blink et al., "Idiopathic Pulmonary Fibrosis: Molecular Mechanisms and Possible Therapeutic Strategies," Arch. Immunol. Ther. Exp. (Warsz), 48:539-545 (2000).
Wattiez at al., "Human bronchoalveolar lavage fluid protein two-dimensional database: Study of interstitial lung diseases," Electrophoresis, 21: 2703-2712 (2000).
Wianny et al., "Specific interference with gene function by double-stranded RNA in early mouse development," Natl. Cell Biol. 2:70 (2000).
Zhang et al., "Lung Monocyte Chemoattractant Protein-1 Gene Expression in Bleomycin-Induced Pulmonary Fibrosis," J. Immunol. 1994, 153:4733-4741.
Ziegenhagen et al., "Increased Expression of Proinflammatory Chemokines in Bronchoalveolar Lavage Cells of Patients with Progressing Idiopathic Pulmonary Fibrosis and Sarcoidosis," J. Investig. Med., 46:223-231 (1998).
Zisman et al., "Pulmonary Fibrosis," Meth. Mol. Med. 2005, 117:3-44.
"American Thoracic Society/European Respiratory Society International Multidisciplinary Consensus Classification of the Idiopathic Interstitial Pneumonias," Am. J. Respir. Crit. Care Med. 165:277-304 (2002).
Abe et al., "Peripheral Blood Fibrocytes: Differentiation Pathway and Migration to Wound Sites," J. Immunol., 166:7556-7562 (2001).
Adachi et al., "Evaluation of Fibronectin Gene Expression by in Situ Hybridization—Differential Expression of the Fibronectin Gene Among Populations of Human Alveolar Macrophages," Am J. Pathol, 133: 193-203 (1988).
Atamas et al., "Pulmonary and Activation-Regulated Chemokine Stimulates Collagen Production in Lung Fibroblasts," Am. J. Respir. Cell Mol. Biol., 29(6):743-9 (2003).
Banas et al., "Roles of SLC/CCL21 and CCR7 in Human Kidney for Mesangial Proliferation, Migration, Apoptosis, and Tissue Homeostasis," J. Immunol. 168:4301-4307 (2002).
Campbell et al., "6-C-kine (SLC), a Lymphocyte Adhesion-triggering Chemokine Expressed by High Endothelium, is an Agonist for the MIP-3β Receptor CCR7," J. Cell Biol. 141:1053-1059 (1998).
Caplen et al., "Specific inhibition of gene expression by small double-stranded RNAs in invertebrate and vertebrate systems," Proc. Natl. Acad. Sci. USA 98:9742 (2001).
Chapman, "Disorders of Lung Matrix Remodeling," J. Clin. Invest. 113:148-57 (2004).
Choi et al., "Enhanced Monocyte Chemoattractant Protein-3/CC Chemokine Ligand-7 in Usual Interstitial Pneumonia," Am. J. Respir. Crit. Care Med., 170:508-515 (2004).
Chua et al., "Pulmonary Fibrosis—Searching for Model Answers," Am. J. Resp. Cell Mol. Biol., 33:9-13 (2005).
Elbashir et al., "Duplexes of 21-nucleotide RNAs mediate RNA interference in cultured mammalian cells," Nature 411:494 (2001).
Epperly et al., "Bone Marrow Origin of Myofibroblasts in Irradiation Pulmonary Fibrosis," Am. J. Respir. Cell Mol. Biol. 29:213-224 (2003).
Fathke et al., "Contribution of Bone Marrow-Derived Cells to Skin: Collagen Deposition and Wound Repair," Stem Cells 22:812-822 (2004).
Forster et al.,"Intracellular and Surface Expression of the HIV-1 Coreceptor CXCR4/Fusion on Various Leukocyte Subsets: Rapid Internalization and Recycling Upon Activation," J. Immunol. 160:1522-1531 (1998).
Gauldie, "Inflammatory Mechanisms are a Minor Component of the Pathogenesis of Idiopathic Pulmonary Fibrosis," Am. J. Resp. Crit. Care Med., 165:1205-1206 (2002).
Genbank Accession No. AB002409.
Genbank Accession No. NM_001032855.
Genbank Accession No. NM_006274.
Gonzalo et al., "Critical Involvement of the Chemotactic Axis CXCR4/Stromal Cell-Derived Factor-1∞ in the Inflammatory Component of Allergic Airway Disease," J. Immunol., 165-499-508 (2000).
Green, "Overview of Pulmonary Fibrosis," Chest 122(6):334S-9S (2002).
Gunn et al., "A chemokine expressed in lymphoid high endothelial venules promotes the adhesion and chemotaxis of naive T lymphocytes," Proc. Natl. Acad. Sci. USA 95:258-263 (1998).
Hammad et al., "Monocyte-Derived Dendritic Cells Induce a House Dust Mite-Specific Th2 Allergic Inflammation in the Lung of Humanized SCID Mice: Involvement of CCR7," J. Immunol. 169:1524-1534 (2002).
Hartlaap et al., "Fibrocytes induce an angiogenic phenotype in cultured endothelial cells and promote angiogenesis in vivo," FASEB J., 15:2215-2224 (2001).
Hashimoto et al., "Bone marrow-derived progenitor cells in pulmonary fibrosis," J. Clin. Invest., 113:243-252 (2004).
Jakubzick et al., "Augmented pulmonary IL-4 and IL-13 receptor subunit expression in idiopathic interstitial pneumonia," J. Clin. Pathol., 57:477-486 (2004).
Jakubzick et al., "Human Pulmonary Fibroblasts Exhibit Altered Interleukin-4 and Interleukin-13 Receptor Subunit Expression in Idiopathic Interstitial Pneumonia," Am. J. Pathol., 164:1989-2001 (2004).
Jakubzick et al., "Impact of Interleukin-13 Responsiveness on the Synthetic and Proliferative Properties of Th1- and Th2-Type Pulmonary Granuloma Fibroblasts," Am. J. Pathol. 162:1475-1486 (2003).
Jakubzick et al., "Role of CCR4 Ligands, CCL17 and CCL22, During Schistosoma mansoni Egg-Induced Pulmonary Granuloma Formation in Mice," Am. J. Pathol., 165:1211-1221 (2004).
Jakubzick et al., "Therapeutic Attenuation of Pulmonary Fibrosis Via Targeting of IL-4- and IL-13-Responsive Cells," J. Immunol. 2003, 171:2684-2693.
Jenh et al., "Cutting Edge: Species Specificity of the CC Chemokine 6Ckine Signaling Through the CXC Chemokine Receptor CXCR3: Human 6Ckine is not a Ligand for the Human or Mouse CXCR3 Receptors," J. Immunol., 1999 162:3765-3769.
Kalluri et al., "Epithelial-mesenchymal transition and its implications for fibrosis," J. Clin. Invest. 112:1776-1784 (2003).
Kaminski et al., "Global analysis of gene expression in pulmonary fibrosis reveals distinct programs regulating lung inflammation and fibrosis," Proc. Natl Acad. Sci. USA, 97:1778-1783 (2000).
Kim et al., "Rules of chemokine receptor association with T cell polarization in vivo," J. Clin. Invest. 108:1331-1339 (2001).
Kim et al., "SLC/Exodus2/6Ckine/TCA4 induces chemotaxis of hematopoietic progenitor cells: differential activity of ligands of CCR7, CXCR3, or CXCR4 in chemotaxis vs. suppression of progenitor proliferation," J. Leukoc. Biol. 66:455-461 (1999).
Kimura et al., "The significance of cathepsins, thrombin and aminopeptidase in diffuse interstitial lung diseases," J. Med. Invest, 52:93-100 (2005).
King et al., "Idiopathic Pulmonary Fibrosis—Relationship between Histopathologic Features and Mortality," Am. J. Respir. Crit. Care Med., 164:1025-1032 (2001).
Kuhn and Mason, "Immunolocalization of SPARC, Tenascin, and Thrombospondin in Pulmonary Fibrosis," Am. J. Pathol. 147(6):1759-1769 (1995).
Lasky et al., "Interstitial Fibrosis and Growth Factors," Environ. Health Perspect., 108(4):751-762 (2000).
Lee et al., "Enhancement of intracellular signaling associated with hematopoietic progenitor cell survival in reponse to SDF-1/CXCL12 in synergy with other cytokines," Blood 99(12):4307-4317 (2002).
Moore et al., "Protection from Pulmonary Fibrosis in the Absence of CCR2 Signaling," J. Immunol., 167:4368-4377 (2001).
Muller et al., "Involvement of chemokine receptors in breast cancer metastasis," Nature 410:50-56 (2001).
Nagira et al., "Molecular Cloning of a Novel Human CC Chemokine Secondary Lymphoid-Tissue Chemokine That is a Potent Chemoattractant for Lymphocytes and Mapped to Chromosome 9p13," J. Biol. Chem. 272:19518-19524 (1997).

(56) References Cited

OTHER PUBLICATIONS

Nicholson et al., "The Prognostic Significance of the Histologic Pattern of Interstitial Pneumonia in Patients Presenting with the Clinical Entity of Cryptogenic Fibrosing Alveolitis," Am. J. Resp. Crit. Car Med 162:2213-7 (2000).

Ortiz et al., "Mesenchymal stem cell engraftment in lung is enhanced in response to bleomycin exposure and ameliorates its fibrotic effects," Proc. Natl. Acad. Sci. USA 100:8407-8411 (2003).

Pardo et al., "Matrix Metalloproteases in Aberrant Fibrotic Tissue Remodeling," Proc. Am. Thorac Soc., 3:383-388 (2006).

Phillips et al., "Circulating fibrocytes traffic to the lungs in response to CXCL12 and mediate fibrosis," J. Clin. Invest., 114:438-446 (2004).

Prasse et al., "A Vicious Circle of Alveolar Macrophages and Fibroblasts Perpetuates Pulmonary Fibrosis via CCL18," Am. J. Respir. Crit. Care Med., 173(7)781-792 (2006).

Ramos et al., "Fibroblasts from Idiopathic Pulmonary Fibrosis and Normal Lungs Differ in Growth Rate, Apoptosis, and Tissue Inhibitor of Metalloproteinases Expression," Am. J. Respir. Cell Mol. Biol., 24:591-598 (2001).

Randolph et al., "The Role of CCR7 in $T_H1$ and $T_H2$ Cell Localization and Delivery of B Cell Help in Vivo," Science, 286:2159-2162 (1999).

Schmidt et al., "Identification of Circulating Fibrocytes as Precursors of Bronchial Myofibroblasts in Asthma," J. Immunol., 171:380-389 (2003).

Selman et al., "Idiopathic pulmonary fibrosis: an epithelial/fibroblastic cross-talk disorder," Respir. Res., 3:3 (2002).

Selman, "Plunging into the Chaos of the Cytokine/Chemokine Cocktail in Pulmonary Fibrosis, How Many and How Important are They," Am. J. Respir. Crit. Care Med., 168:730-731 (2003).

Skovseth et al., "Vascular Morphogenesis and Differentiation after Adoptive Transfer of Human Endothelial Cells to Immunodeficient Mice," Am. J. Pathol., 2002, 160:1629-1637.

Sozzani et al., "Cutting Edge: Differential Regulation of Chemokine Receptors During Dendritic Cell Maturation: A Model for Their Trafficking Properties," J. Immunol., 161(3):1083-1086 (1998).

Strieter "Inflammatory Mechanisms are not a Minor Component of the Pathogenesis of Idiopathic Pulmonary Fibrosis," Am. J. Resp. Crit. Care Med., 165:1207-1208 (2002).

Svoboda et al., "Selective reduction of dormant maternal mRNAs in mouse oocytes by RNA interference," Development 127:4147 (2000).

Tavor et al., "CXCR4 Regulates Migration and Development of Human Acute Myelogenous Leukemia Stem Cells in Transplanted NOD/SCID Mice," Cancer Res. 64:2817-2824 (2004).

Timmons, "Specific interference by ingested dsRNA," Nature 395:854 (1998).

Underwood et al., "SB 239063, a p38 MAPK inhibitor, reduces neutrophilia, inflammatory cytokines, MMP-9, and fibrosis in lung," Am. J. Physiol. Lung Cell Mol Physiol 279:L895-L902 (2000).

Ward et al., "Chemokines: understanding their role in T-lymphocyte biology," Biochem. J. 333:457-470 (1998).

Waterhouse et al., "Virus resistance and gene silencing in plants can be induced by simultaneous expression of sense and antisense RNA," Proc. Natl. Acad. Sci. USA 95:13959 (1998).

White et al., "Negative Regulation of Myofibroblast Differentiation by PTEN (Phosphatase and Tensin Homolog Deleted on Chromosome 10)," Am. J. Respir. Crit. Care Med., 173(1):112-1121 (2006).

Yang et al., "Specific Double-Stranded RNA Interference in Undifferentiated Mouse Embryonic Stem Cells," Mol. Cell Biol. 21:7807 (2001).

Yoshida et al., "Molecular Cloning of a Novel Human CC Chemokine EBI1-ligand Chemokine That is a Specific Functional Ligand for EBI1, CCR7," J. Biol. Chem. 272:13803-13809 (1997).

\* cited by examiner

METHODS FOR TREATING PULMONARY FIBROSIS

This invention was made with government support under Grant No. P50 HL-56402 awarded by the National Institutes of Health. The government has certain rights in the invention.

The present application claims the benefit of priority of U.S. Provisional application No. 60/753,647, which was filed Dec. 23, 2005 and is specifically incorporated herein by reference in its entirety.

FIELD OF THE INVENTION

The present invention relates to methods and compositions for the treatment of chronic fibrosing disorders. More particularly, the invention relates to the immunotherapeutic intervention of chronic fibrosing disorders.

BACKGROUND OF THE INVENTION

Inflammation is the coordinated response to tissue injury or infection. Inflammation begins with the release of local release of chemotactic factors, platelet activation, and initiations of the coagulation and complement pathways. These events stimulate the local endothelium, promoting the extravasation of neutrophils and monocytes. The second phase of inflammation is characterized by the influx into the tissue of cells of the adaptive immune system, including lymphocytes. The subsequent resolution phase, when apoptosis of the excess leukocytes and engulfment by tissue macrophages takes place, is also characterized by repair of tissue damage by stromal cells, such as fibroblasts.

In such repair mechanisms local quiescent fibroblasts migrate into the affected area, produce extracellular matrix proteins, and promote wound contraction or fibrosis. It has also been suggested that is that circulating fibroblast precursor cells, fibrocytes, which are present within the blood migrate to the sites of injury or fibrosis, where they differentiate and mediate tissue repair and other fibrotic responses. Fibrocytes differentiate from a CD14+ peripheral blood monocyte precursor population and express markers of both hematopoietic cells (CD45, MHC class II, CD34) and stromal cells (collagen types I and III and fibronectin). Mature fibrocytes rapidly enter sites of tissue injury where they secrete inflammatory cytokines, as well as extracellular matrix proteins, other cytokines and pro-angiogenic molecules, which may result in fibrosis.

Fibrocyte differentiation is associated with a variety of fibrotic diseases including but not limited to scleroderma, keloid scarring, rheumatoid arthritis, lupus, nephrogenic fibrosing dermopathy, and idiopathic pulmonary fibrosis. They play a role in the formation of fibrotic lesions after Schistosoma japonicum infection in mice and are also implicated in fibrosis associated with autoimmune diseases. Fibrocytes have also been implicated in pathogenic fibrosis associated with radiation damage, Lyme disease and pulmonary fibrosis, as well as stromal remodeling in pancreatitis and stromal fibrosis, whereas lack of such fibrocytes is associated with pancreatic tumors and adenocarcinomas. Fibrosis additionally occurs in asthma patients and possibly other pulmonary diseases such as chronic obstructive pulmonary disease when fibrocytes undergo further differentiation into myofibroblasts.

A specific set of diseases that are known to involve unchecked fibrotic response are idiopathic interstitial pneumonias, a diverse group of chronic pulmonary diseases characterized by varying levels of pulmonary fibrosis. The major factors driving the dominant pulmonary fibrotic response associated with various histologically distinct forms of idiopathic interstitial pneumonia (IIP) remains poorly defined, thereby contributing to the lack of effective clinical treatments for these diseases. (Green, Overview of pulmonary fibrosis. Chest 2002; 122 (suppl. 6):334S-9S). Although many of these diseases exhibit a fibroproliferative response in the alveolar microenvironment leading to respiratory impairment, the degree of fibrotic change varies considerably among them. (Nicholason Am. J. Resp. Crit. Car Med/2000: 162:2213-7; Chapman J. Clin., Invest., 2004; 113:148-57). Equally perplexing is the clear demonstration that anti-inflammatory agents provide therapeutic benefit in less severe forms of IIP, such as non-specific interstitial pneumonia (NSIP) and respiratory bronchiolitis/interstitial lung disease (RBILD), but they often fail to prevent respiratory failure in patients with the most severe and deadly form of IIP—usual interstitial pneumonia (UIP). (Flaherty et al., Am. J. Med., 110:278-282 (2001); Lynch et al., Curr. Opin. Pulm. Med., 7:298-308 (2001); Flaherty et al., Thorax, 58:143-148 (2003))

The existence of distinct foci of fibroblasts, or fibroblastic foci, is an important pathological feature associated with a poor prognosis and a fatal outcome in idiopathic interstitial pneumonia. (King et al., Am. J. Respir. Crit. Care Med., 164:1025-1032 (2001)) Newer treatments may follow after the elucidation of the shared and divergent events that contribute to pulmonary fibrotic changes during the initiation and maintenance of IIP. (van den Blink et al., Arch. Immunol. Ther. Exp. (Warsz), 48:539-545 (2000)) CC chemokine receptor 7 (CCR7; which binds MIP-3b/CCL19 and 6-Ckine/CCL21 (Nagira et al., J. Biol. Chem., 272:19518-19524 (1997)) and CX chemokine receptor 4 (CXCR4; which binds SDF-1/CXCL12 (Forster et al., J. Immunol., 160:1522-1531 (1998)) are chemokine receptors that were widely recognised as being limited in their expression to cells of haemopoietic origin. (Kim et al., J. Leukoc. Biol., 66:455-461 (1999); Kim et al., J. Clin. Invest., 108:1331-1339 (2001)) During immune responses, CCR7 expression facilitates the movement of mature dendritic cells (Sallusto et al., Eur. J. Immunol., 29:1617-1625 (1999)) to lymphoid tissues, regulates the localisation of T helper type 1 and 2 cells within the spleen, (Randolph et al., Science, 286:2159-2162 (1999)) and directs T helper type 2 cells to the allergic lung. (Hammad et al., J. Immunol., 169:1524-1534 (2002)) CXCR4 expression and effects were largely limited to bone marrow derived immune cells. (Ward et al., Biochem. J., 333:457-470 (1998); Gonzalo et al., J. Immunol., 165:499-508 (2000)) Recent evidence showing that the expression of CCR7 and CXCR4 by breast tumour cells allows these cells to metastasize to the lung has modified this immunocentric paradigm. (Muller et al., Nature, 410:5-056 (2001)) Breast cells do not express these chemokine receptors or respond to the ligands that bind them. (Muller et al., Nature, 410:50-56 (2001)) This observation has been extended to several metastasizing tumour types, including melanoma (Murakami et al., J. Dermatol. Sci., 36:71-78 (2004)) and various forms of leukaemia. (Tavor et al., Cancer Res., 64:2817-2824 (2004); Ghobrial et al., Mayo Clin. Proc., 79:318-325 (2004))

Chronic pulmonary fibrosis results from scarring throughout the lungs which can be caused by many conditions including chronic inflammatory processes (sarcoidosis, Wegener's granulomatosis), infections, environmental agents (asbestos, silica, exposure to certain gases), exposure to ionizing radiation (such as radiation therapy to treat tumors of the chest), chronic conditions (lupus, rheumatoid arthritis), and even certain medications. In a condition known as hypersensitivity pneumonitis, fibrosis of the lung can develop following a heightened immune reaction to inhaled organic dusts or occupational chemicals. This condition most often results from inhaling dust contaminated with bacterial, fungal, or animal products. In some types of pulmonary fibrosis, such as non-specific interstitial pneumonitis (NSIP), the subject may respond to immune suppressive therapy. Where, as often happens, chronic pulmonary inflammation and fibrosis develop without an identifiable cause, the subject suffering from the disease often will not respond to medical therapy. This is particularly true of subjects suffering from idiopathic pulmonary fibrosis (IPF). The treatment options for idiopathic pulmonary fibrosis are very limited. There is no evidence that any medications can help this condition, since scarring is permanent once it has developed. Lung transplantation is the only therapeutic option available. Research trials using different drugs that may reduce fibrous scarring are ongoing. Since some types of lung fibrosis can respond to corticosteroids (such as Prednisone) and/or other medications that suppress the body's immune system, these types of drugs are sometimes prescribed in an attempt to decrease the processes that lead to fibrosis. Nevertheless, it is well-recognized that at present there are no treatments for fibrosing diseases. It is standard clinical practice to give patients prednisone and azathioprine but there is no data showing that these drugs provide any therapeutic benefit. In fact, the side-effects of these drugs may contribute to mortality in UIP patients.

While chemokines may be involved with the formation of fibroblastic foci and the amplification of the fibrotic response in pulmonary fibrosis, the particular role of the profibrotic mediator milieu present during chronic pulmonary fibrosis remains unclear. The present invention identifies the role of specific chemokines and their receptors and provides for new methods and compositions for therapy, especially for the idiopathic disorders that are refractory to medical therapy.

SUMMARY OF THE INVENTION

The present invention is directed to methods and compositions for the treatment of fibrosing diseases are described. More specifically, the invention demonstrates that inhibiting or otherwise decreasing the activity of CCL21 either alone or in combination with CCL19 will be effective in reducing the presence of fibrotic lesions and ameliorating the symptoms of fibrosing disorders.

Thus in specific embodiments the invention is directed to methods of treating a chronic fibrosing disorder in a mammal comprising decreasing the presence or activity of CCL21 in the fibrocytes and/or fibroblasts present at a fibrotic lesion in said fibrosing disorder. The method, in certain embodiments, may further comprise decreasing the presence or activity of CCL19 in the fibroblasts associated with said fibrosing disorder. For example, decreasing the presence or activity of CCL21 may comprise contacting said mammal with an agent that removes CCL21 from said fibroblasts, in an amount effective to alleviate one or more of the symptoms of said chronic fibrosing disorder. An exemplary such agent may be an antibody that is specifically immunoreactive with CCL21, such as, for example an antibody that preferentially recognizes epitopes on CCL21 as compared to other chemokines. In some embodiments, the decreasing the presence or activity of CCL21 and CCL19 in the fibrocytes and/or fibroblasts comprises contacting the mammal with an agent that removes CCL21 and CCL19 from the fibrocytes and/or fibroblasts, in an amount effective to alleviate one or more of the symptoms of said chronic fibrosing disorder.

In other embodiments, the decreasing the presence or activity of CCL21 comprises contacting said mammal with an agent that decreases the expression of CCL21 in said fibroblasts, in an amount effective to alleviate one or more of the symptoms of said chronic fibrosing disorder. An exemplary agent for such embodiments may be an siRNA molecule directed against CCL21.

The fibrosing disorder treatable by the invention may be any fibrosing disorder, including, but not limited to one that is selected from the group consisting of pulmonary fibrosis, chronic obstructive pulmonary disease, hepatic fibrosis, rheumatoid arthritis, congestive heart failure, chronic renal disease, hypersensitivity pneumonitis, respiratory bronchiolitis/interstitial lung disease, schistosoma mansoni infection, primary pulmonary hypertension (prevention of the formation of the plexiform lesion) herpes virus associated-diseases, which include lung and dermatological manifestations; keloid scarring, lupus, nephrogenic fibrosing dermopathy, fibrosing lesions associated with Schistosoma japonicum infection, autoimmune diseases, pathogenic fibrosis, Lyme disease, stromal remodeling in pancreatitis and stromal fibrosis, uterine fibroids, ovarian fibrosis, corneal fibrosis congestive heart failure and other post-ischemic conditions, post-surgical scarring including abdominal adhesions, wide angle glaucoma trabeculotomy, and any combinations thereof.

Typical pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease. In preferred embodiments, the fibrosing disorder is chronic pulmonary fibrosis.

In the treatment methods, the compound may be administered locally to the site of a fibrosing lesion. In more specific embodiments, the fibrosing lesion is in a lung and the composition is contacted locally with said lesion. In certain embodiments, it is contemplated that the agent comprises a targeting moiety to specifically locate said agent to the site of a fibrosing lesion.

In specific embodiments, the antibody or the anti-CCL21 or anti CCL19 composition is administered using a mode of administration selected from the group consisting of topical administration, injection, inhalation, continuous release by depot or pump, or any combinations thereof.

Another aspect of the invention is a method A method of inhibiting fibroblast and/or fibrocyte proliferation comprising contacting said fibroblast and/or fibrocyte with a composition that comprises an anti-CCL21 antibody or an siRNA molecule designed against CCL21. In some embodiments, the method further comprises contacting said fibroblast with a composition that comprises an anti-CCL19 antibody or an siRNA molecule designed against CCL19. In still other embodiments, the method further comprises contacting said fibroblast with a composition that comprises an anti-CCR7 antibody or an siRNA molecule designed against the CCR7 receptor. The fibrocytes and/or fibroblasts being treated may be located in vitro, or in vivo. Preferably, they are located in vivo. More preferably, they are located in vivo in lung tissue.

Also included are methods of inhibiting the migration of fibrocytes and/or activation of fibroblasts comprising contacting said fibrocytes and/or fibroblasts with a composition that inhibits that activity of CCL21. In such methods that fibrocytes are located in vivo in a mammal and said method inhibits migration of fibrocytes to lung tissue in said mammal, thereby preventing the excessive production of extracellular matrix. In these methods the fibroblasts preferably are resident pulmonary fibroblasts located in lung tissue in a mammal and said method inhibits activation of said fibroblasts in the lung tissue in said mammal, thereby preventing the excessive production of extracellular matrix.

Also taught herein is a method of treating pulmonary fibrosis comprising inhibiting the migration of fibrocytes and/or the activation of resident pulmonary fibroblasts located in lung tissue in a mammal suffering from fibrotic pulmonary disease by inhibiting the activity or expression of CCL21 in said fibrocytes and/or said fibroblasts thereby preventing the excessive production of extracellular matrix and ameliorating the symptoms of pulmonary fibrosis.

Also contemplated are methods of treating, inhibiting the development of, ameliorating one or more symptoms of, reversing the condition of or otherwise achieving a therapeutic outcome in radiation-induced pulmonary laminitis and/or radiation induced pulmonary fibrosis in a subject comprising administering to said subject an agent that decreases the presence or activity of CCL21 in the fibrocytes and/or fibroblasts in the pulmonary tissue of said subject, wherein said agent is administered prior to, and/or during, and/or after the administration of radiation therapy. Such a therapeutic method may further comprise administering an agent that decreases the presence or activity of CCL19 in the pulmonary tissue of said subject.

A further aspect of the present invention contemplates methods of treating, inhibiting the development of, ameliorating one or more symptoms of, reversing the condition of or otherwise achieving a therapeutic outcome in drug-induced pulmonary fibrosis in a subject comprising administering to said subject an agent that decreases the presence or activity of CCL21 in the fibrocytes and/or fibroblasts in the pulmonary tissue of said subject, wherein said agent is administered prior to, and/or during, and/or after the administration of the drug. Again, it may be desirable in such a method to further administer an agent that decreases the presence or activity of CCL19 in the in the pulmonary tissue of said subject. There are numerous drugs that cause fibrosis, such agents include, but are not limited to cytotoxic agents, antibiotics, antiarrhythmic agents, anti-inflammatory agents, and illicit drugs. Exemplary agents that cause pulmonary fibrosis include but are not limited to Amphotericin B, bleomycin, bromocriptine, busulfan, carbamazepin, chlorambucil, cocaine, cyclophosphamide, diphenylhydantoin, ergotamine, flecainide, heroin, melphalan, methadone, methotrexate, methylphenidate, methylsergide, mineral oil, nitrofurantoin, nitrosureas, procarbazine, silicone, sulfasalazine tocainide, and the vinca alkaloid class of agents. In the treatment methods described herein it may be desirable to present as an adjunct therapy a regimen in which the therapeutic agent that affects the CCL21 and/or CCL19 is combined with a corticosteroid and/or immunosuppressive agent. In additional methods, the combination therapy may comprise administering anticoagulants, diuretics, cardiac glycosides, calcium channel blockers, vasodilators, prostacyclin analogues, endothelin antagonists, phosphodiesterase inhibitors, beta-2 agonists, antimuscarinics, endopeptidase inhibitors, lipid lowering agents and thromboxane inhibitors, or combinations thereof.

In addition, the invention further contemplates the use of an agent that decreases the presence or activity of CCL21 and/or CCL19 in the fibrocytes and/or fibroblasts present at a fibrotic lesion for the preparation of a medicament for the treatment of a chronic fibrosing disorder.

In exemplary embodiments, the invention provides for a use of an agent for decreasing the presence or activity of CCL21, and optionally an agent that decreases the presence or activity of CCL19, in the fibrocytes and/or fibroblasts present at a fibrotic lesion for the preparation of a medicament for the treatment of a chronic fibrosing disorder in a mammal. In certain embodiments, the agent is an antibody that is specifically immunoreactive with CCL21, preferably the antibody is one that preferentially recognizes epitopes on CCL21 as compared to other chemokines. In other embodiments, the agent is an siRNA molecule directed against CCL21. The medicament is manufactured for treating a fibrosing disorder is selected from the group consisting of pulmonary fibrosis, chronic obstructive pulmonary disease, hepatic fibrosis, rheumatoid arthritis, congestive heart failure, chronic renal disease, hypersensitivity pneumonitis, respiratory bronchiolitis/interstitial lung disease, schistosoma mansoni infection, primary pulmonary hypertension caused by plexiform lesions, lung manifestation of herpes virus associated-diseases, dermatological manifestations of herpes virus associated diseases; keloid scarring, lupus, nephrogenic fibrosing dermopathy, fibrosing lesions associated with Schistosoma japonicum infection, autoimmune diseases, pathogenic fibrosis, Lyme disease, stromal remodeling in pancreatitis and stromal fibrosis, uterine fibroids, ovarian fibrosis, comeal fibrosis congestive heart failure and other post-ischemic conditions, post-surgical scarring of the abdomen, post-surgical scarring of wide angle glaucoma trabeculotomy, and any combinations thereof. Preferably, the fibrosing disorder is chronic pulmonary fibrosis.

The medicaments are preferably formulated for a mode of administration selected from the group consisting of topical administration, injection, inhalation, continuous release by depot or pump, or any combinations thereof.

Also contemplated is a use of a composition that comprises an anti-CCL21 antibody or an siRNA molecule designed against CCL21 and optionally an anti-CCL19 or siRNA molecule designed against CCL19, for the preparation of a medicament for inhibiting fibroblast and/or fibrocyte proliferation. The use may further comprise use of a composition that comprises an anti-CCR7 antibody or an siRNA molecule designed against the CCR7 receptor for the manufacture of a medicament for f inhibiting fibroblast and/or fibrocyte proliferation.

Another aspect contemplates use of a composition that inhibits that activity of CCL21 for the manufacture of a medicament for inhibiting the migration of fibrocytes and/or activation of fibroblasts. Also contemplated is use of a composition that inhibits the activity or expression of CCL21 in fibrocytes and/or the activation of resident pulmonary fibroblasts for the manufacture of a medicament for the treatment of pulmonary fibrosis by prevention of the excessive production of extracellular matrix and ameliorating the symptoms of pulmonary fibrosis.

In addition contemplated herein is a use of an agent that that decreases the presence or activity of CCL21, and optionally an agent that decreases the presence or activity of CCL19 in the fibrocytes and/or fibroblasts in the pulmonary tissue for the manufacture of a medicament for the treatment of radiation-induced pulmonary laminitis and/or radiation induced pulmonary fibrosis.

The use of an agent that decreases the presence or activity of CCL21, and optionally an agent that decreases the presence or activity of CCL19 in the fibrocytes and/or fibroblasts in the pulmonary tissue for the manufacture of a medicament for the treatment of drug-induced pulmonary fibrosis also is contemplated. In such a use the medicament is manufactured for the treatment of non-idiopathic pulmonary fibrosis induced by a drug selected from the group consisting of a cytotoxic agent, an antibiotic, an antiarrhythmic agent, an anti-inflammatory agent, and an illicit drug, for example the drug may be selected from the group consisting of Amphotericin B, bleomycin, bromocriptine, busulfan, carbamazepin, chlorambucil, cocaine, cyclophosphamide, diphenylhydantoin, ergotamine, flecainide, heroin, melphalan, methadone, methotrexate, methylphenidate, methylsergide, mineral oil, nitrofurantoin, nitrosureas, procarbazine, silicone, sulfasalazine tocainide, and the vinca alkaloid class of agents. In some embodiments, the combined use of agents is contemplated for the preparation of a medicament wherein the CCL19 or CCL21-based medicament is combined with a corticosteroid, an immunosuppressive agent, an anticoagulant, a diuretic, a cardiac glycoside, a calcium channel blocker, a vasodilator, a prostacyclin analogue, an endothelin antagonist, a phosphodiesterase inhibitors, a beta-2 agonist, an antimuscarinic agent, an endopeptidase inhibitor, a lipid lowering agent and thromboxane inhibitors, or combinations thereof.

RBILD, respiratory bronchiolitis/interstitial lung disease; SLB, surgical lung biopsy; UIP, usual interstitial pneumonia.

FIG. 10 Representative immunohistochemical analysis of (B, E) collagen 1 and (C, F) CCR7 in SLBs from (A-C) UIP and (D-F) RBILD patient groups. Panels (A) and (D) show control staining. Collagen 1 immunoreactivity (red staining) was present in (B) UIP and (E) RBILD patient groups. However, in serial histological sections, areas that were immunoreactive for collagen 1 lacked CCR7 expression (C, UIP; F, RBILD). Original magnification, 6200. CCR7, CC chemokine receptor 7; RBILD, respiratory bronchiolitis/interstitial lung disease; SLB, surgical lung biopsy; UIP, usual interstitial pneumonia.

FIG. 11 Representative immunohistochemical analysis of a smooth muscle actin (aSMA) in SLBs from (A-C) UIP, (D-F) NSIP, and (G-I) RBILD patient groups. Panels (A), (D), and (G) show control staining. CCR7 immunoreactivity (red staining) was seen in focal areas of SLBs from patients with (B) UIP, (E) NSIP, and (H) RBILD. In serial histological tissue sections, aSMA expression (red staining) was also seen in (C) UIP, (F) NSIP, and (I) RBILD patient groups. However, no overlap between CCR7 and aSMA expression was seen. Original magnification, was 6200. CCR7, CC chemokine receptor 7; NSIP, non-specific interstitial pneumonia; RBILD, respiratory bronchiolitis/interstitial lung disease; SLB, surgical lung biopsy; aSMA, a smooth muscle actin; UIP, usual interstitial pneumonia.

Figure 12:
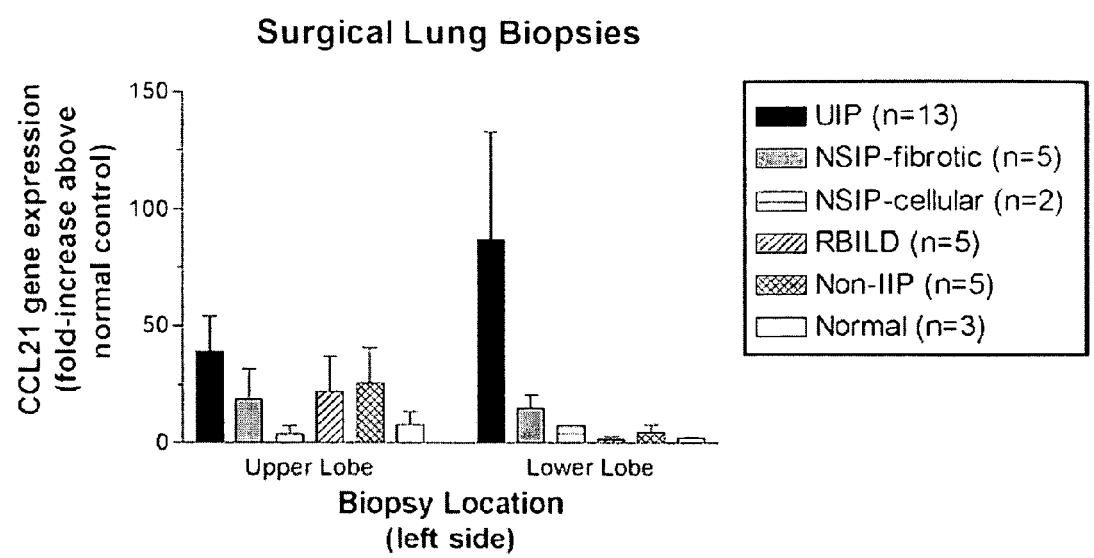

FIG. 12: transcript expression for CCL21 in surgical lung biopsies from patients with various forms of chronic pulmonary fibrosis compared with those who have other types of non-fibrosing diseases. CCL21 gene expression (examined by TAQMAN PCR) was variable between patient groups. The greatest expression of CCL21 was observed in upper and lower usual interstitial pneumonia (UIP) SLBs, but the discrepancy between UIP SLBs and all other groups was most pronounced in the lower SLBs examined. Together, these data suggested that the expression of CCR7 and CCL21 was markedly enhanced during UIP. NSIP=Non-specific interstitial pneumonia; RBILD=respiratory bronchiolitis/interstitial lung disease.

Figure 13:
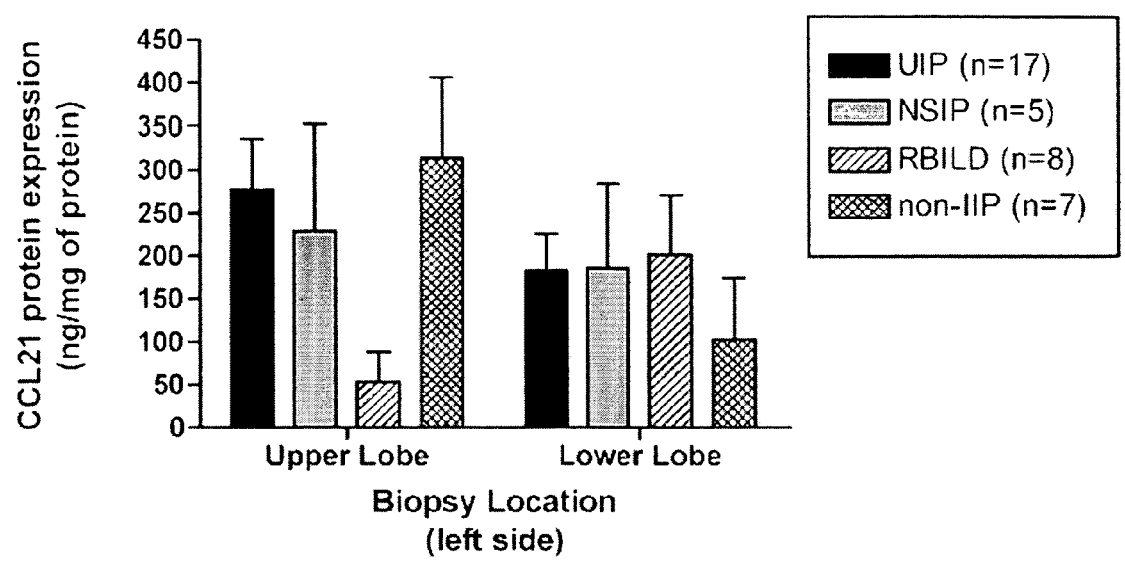

FIG. 13: protein expression for CCL21 in surgical lung biopsies from patients with various forms of chronic pulmonary fibrosis compared with those who have other types of non-fibrosing diseases. ELISA analysis of IIP and non-IIP biopsy samples is shown here. In upper lobe biopsies, protein levels of CCL21 were similar among the UIP, NSIP, and non-IIIP groups. However, in the lower lobe samples (where pulmonary fibrosis is more aggressive in IIP patients), levels of CCL21 were greater in the IIP groups (i.e. UIP, NSEP, and RBILD groups compared with the non-IIP group).

Figure 14:
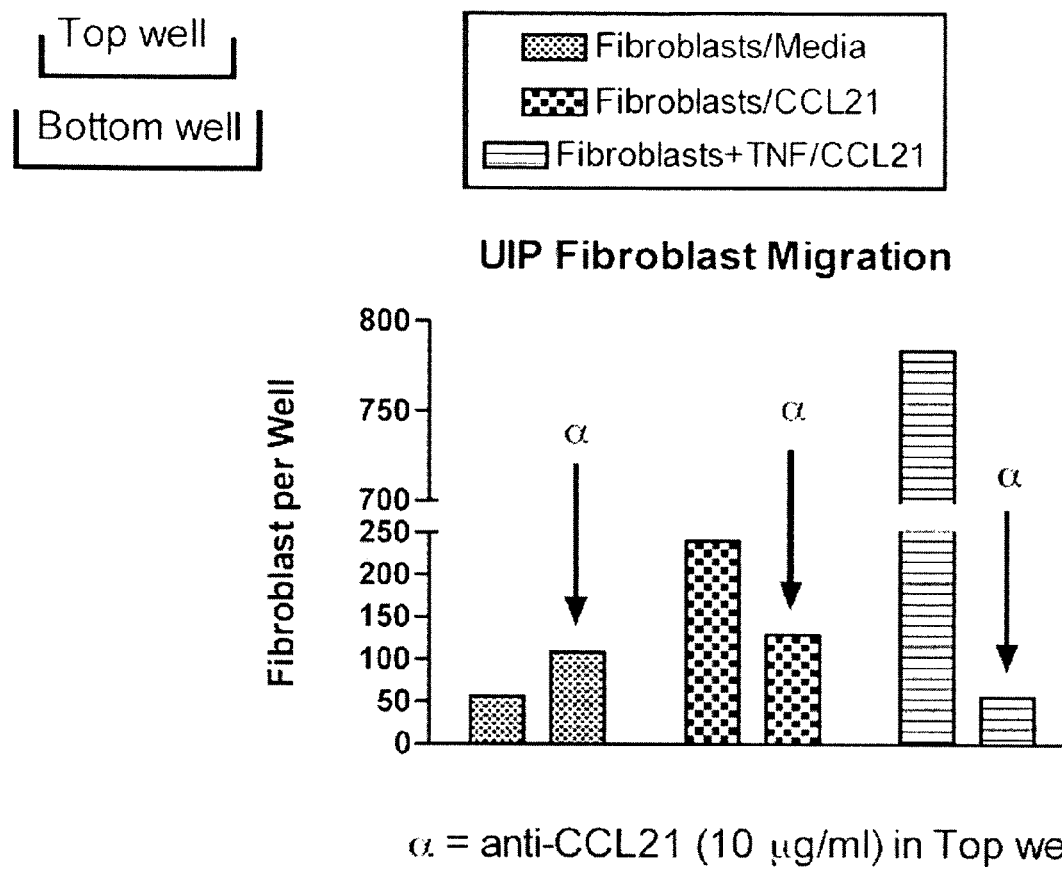

FIG. 14: The migration of UIP fibroblasts but not non-IIP fibroblasts was markedly augmented by the presence of CCL21. These experiments involved the addition of human fibroblasts to a porous transwell culture plate system and the counting of fibroblasts that migrated through during an 24 h incubation. UIP fibroblasts migrated through the transwell to the bottom well, and this response was markedly augmented if CCL21 was added to the bottom well, or the fibroblasts were treated with TNF and CCL21 was added to the bottom well. The presence of an anti-CCL21 antibody markedly attenuated fibroblast migration in the latter two groups but had no effect on the first group.

Figures 15A, 15B, 15C, 15D:
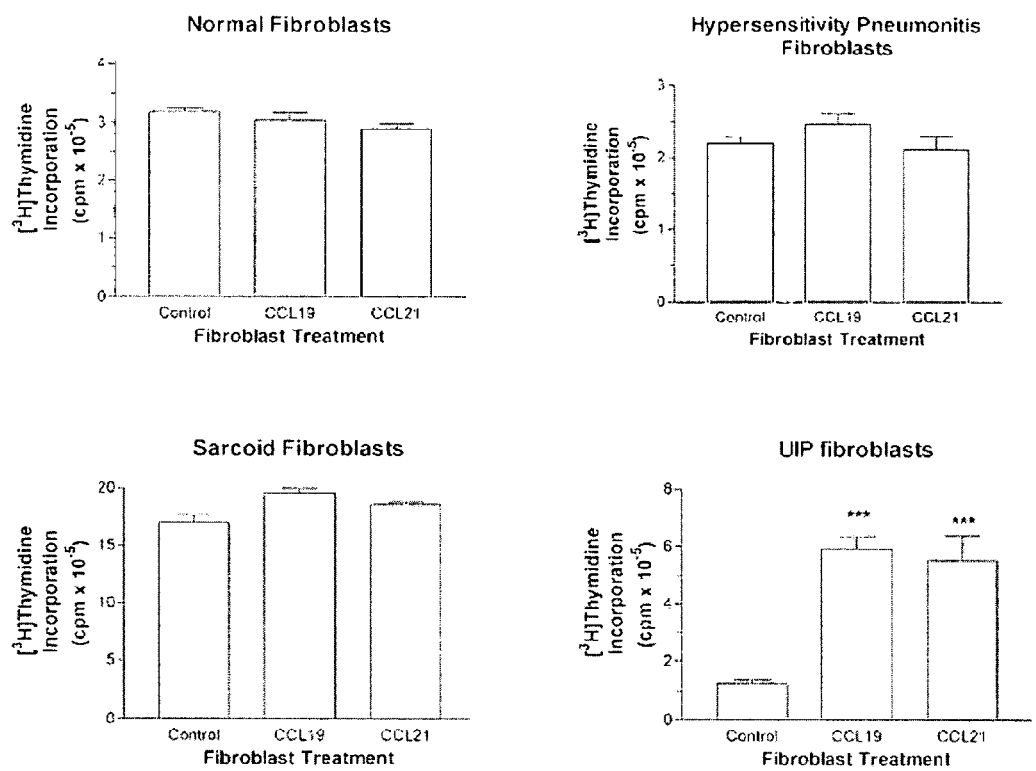

FIG. 15: Shown here is the examination of the effect of exogenous CCL19 and CCL21 (both at 10 ng/ml) on the proliferative responses of primary fibroblast lines grown up from normal, hypersensitivity pneumonitis, sarcoid and UIP SLBs. It was apparent that UIP fibroblasts exhibited a proliferative response to the presence of CCL19 and CCL21 ligands.

Figures 16A, 16B:
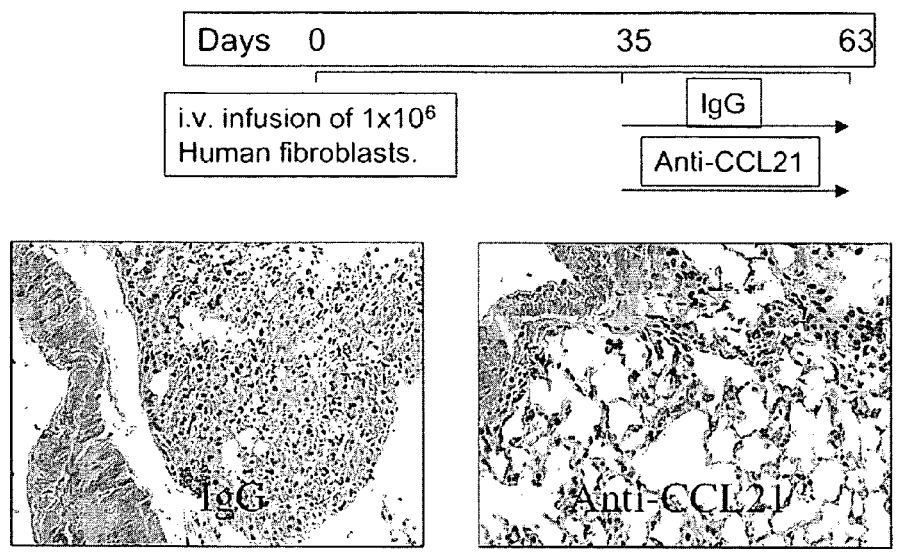

FIG. 16: Having observed that the introduction of IIP fibroblasts into SCID mice promoted the development of interstitial fibrosis, the next studies were designed to assess the anti-fibrotic effect of anti-CCL21 in this model. Groups of five mice received purified IgG or anti-CCL21 antibody by i.p. injection beginning at day 35 and every other day subsequently to day 63. At day 63, lung tissues were removed and representative sections follow. The IgG treated mice exhibited marked evidence of interstitial fibrosis and remodeling. Conversely, the anti-CCL21 antibody treatment groups showed little evidence of pulmonary fibrosis based on histological analysis.

DETAILED DESCRIPTION OF THE PREFERRED EMBODIMENTS OF THE INVENTION

Fibrosis involves the unchecked proliferation and differentiation of fibrocytes. Fibrocytes are a distinct population of fibroblast-like cells derived from peripheral blood monocytes that normally enter sites of tissue injury to promote angiogenesis and wound healing. In the present invention it is shown that decreasing the presence or activity of CCL21 in the fibrocytes and/or fibroblasts present at a fibrotic lesion in fibrosis will result in a beneficial outcome of treating the fibrosis by either decreasing the presence of fibrotic foci, and/or inhibiting the formation of fibrotic foci, and/or ameliorating one or more of the symptoms of fibrosis.

Chronic pulmonary fibrosis of known and idiopathic origin presents extraordinary clinical challenges for which treatment options show limited effectiveness or toxicity (Flaherty et al., Am. J. Med., 110:278-282 (2001); (Hampton et al., Am. J. Respir. Crit. Care Med., 149:A878 (1994)), and the median survival rate following diagnosis has changed little (Ryu et al., Mayo Clin. Proc., 73:1085-1101 (1998); Lasky et al., Environ. Health Perspect., 108 Suppl 4:751-762 (2000)). Known profibrotic stimuli include radiation, inhaled mineral and organic particles, gaseous oxidants, pharmaceutics and infectious organisms, whereas debate persists regarding the identity of etiological factors that initiate the clinicopathologic entities of idiopathic interstitial pneumonias (IIP). IIP are a diverse group of disorders involving the distal pulmonary parenchyma, which share numerous features, but are felt to be sufficiently different to justify designation as separate disorders (Travis et al., Am. J. Surg. Path., 24:19-33 (2000)). Their pathogenesis remains unclear but is thought to center around an injury (or multiple injuries) to the lung followed by attempts to heal this injury. Fibroblastic foci, small aggregates of actively proliferating fibroblasts, are believed to represent the organization of prior foci of injury and indicate that fibrosis is active and ongoing.

Initially, using IIP as examples of chronic fibrosing disorders, presented herein are data that show that CCR7 and/or CXCR4 expression would be high in the fibrotic disorder (in this case IIP surgical lung biopsies (SLBs)) and is not high in normal margin SLBs. Detailed gene transcript and protein analysis of SLBs from IIP and normal margin tumour patient groups was performed. Chemokine and chemokine receptor transcript analysis revealed that CCR7, but not CXCR4, was highly expressed in focal interstitial areas within IIP, particularly all UIP biopsies analyzed, but not in normal margin biopsies. CCR7 positive areas in IIP biopsies contained fibrocytes, however, given that the cells present in CCR7 positive areas did not coexpress fibrocyte markers, such as CD34 and collagen, the CCR7 positive cells are not necessarily bone marrow derived cells. Finally, it is demonstrated that the CCR7 positive cells in IIP biopsies were activated resident tissue fibroblasts. Thus, the examples presented herein demonstrate increased expression of CCR7 in severe IIP, and this expression was localised to focal fibrotic areas devoid of fibrocytes and myofibroblasts.

In further investigations it was shown that targeting of the CCL21 and/or CCL19 ligands of the CCR7 receptor is a good intervention for the treatment of chronic fibrosing diseases. More particularly, clinical and animal modeling data showed that expression of CCR7 and CCL21 was markedly enhanced during UIP. It is further demonstrated that the migration of UIP fibroblasts was augmented by the presence of CCL21. On the other hand, anti-CCL21 antibody preparations greatly attenuated the fibroblast migration in UIP. Furthermore, in the presence of CCL21 or CCL19 ligands it is apparent that UIP fibroblasts exhibit a proliferative response.

When IIP fibroblasts are introduced into SCID mice, the mice develop induced to develop interstitial fibrosis. This model serves as a humanized SCID model of IIP. When these model mice are treated with anti-CCL21 antibody, the mice showed little or no histological evidence of pulmonary fibrosis as compared to similar groups of humanized SCID mice models of IIP that had not been treated with anti-CCL21 antibodies.

In view of the data shown herein it is contemplated that methods and compositions that are directed to decreasing and/or inhibiting the action of CCL21 and/or CCL19 will be particularly useful for the treatment of fibrosing disorders in the lung as well as in other tissues. The responsiveness of human fibroblasts to CCL19 and CCL21 (due their upregulation of CCR7) leads to the inappropriate activation of these cells thereby leading to the exuberant fibrotic responses observed in IIP. Interestingly, the cytokine environment in the lung of fibrotic patients may favor the aberrant response to CCL19 and CCL21 since other investigators have documented increased protein levels of TNF-α (Sallusto et al., Eur. J. Immunol., 29:1617-1625 (1999); Randolph et al., Science, 286:2159-2162 (1999)) and decreased IL-10 (Hammad et al., J. Immunol., 169:1524-1534 (2002)), both cytokines that modulate the receptor that these ligand bind to. Human fibroblasts from patients with severe forms of pulmonary fibrosis clearly respond to CCL19 and CCL21, thereby making these ligands attractive targets in the treatment of fibrosing diseases in the lung and possibly in other tissues.

In view of the above discussion it should be understood that in certain embodiments, it is contemplated that the compositions that target the CCL21 and/or CCL19 specifically inhibit the interaction of the chemokine with the CCR7 receptor. Such compositions may be directed against the CCL21 and/or CCL19 itself (e.g., antibodies against these chemokines, antisense molecules designed against these chemokines or siRNA molecules designed against these molecules). Alternatively, the compositions may be directed against the CCR7 receptor (e.g., antibodies against the receptor, antisense molecules designed against the receptor or siRNA molecules designed against the receptor). In still other alternatives, the composition may be one which comprises a small molecule inhibitor of the interaction of the chemokines with the CCR7 receptor. These compositions and methods of use the same to treat and/or ameliorate the symptoms of diseases in a subject are discussed in further detail below.

Any fibrosing disorder may be treated. For example, the disorder may include pulmonary fibrosis, chronic obstructive pulmonary disease, hepatic fibrosis, rheumatoid arthritis, congestive heart failure, chronic renal disease, hypersensitivity pneumonitis, respiratory bronchiolitis/interstitial lung disease, schistosoma mansoni infection, primary pulmonary hypertension (prevention of the formation of the plexiform lesion) herpes virus associated-diseases, which include lung and dermatological manifestations; keloid scarring, lupus, nephrogenic fibrosing dermopathy, fibrosing lesions associated with Schistosoma japonicum infection, autoimmune diseases, pathogenic fibrosis, Lyme disease, stromal remodeling in pancreatitis and stromal fibrosis, uterine fibroids, ovarian fibrosis, corneal fibrosis congestive heart failure and other post-ischemic conditions, post-surgical scarring including abdominal adhesions, wide angle glaucoma trabeculotomy, and any combinations thereof. Another area in which the methods will be useful is in the inhibition of epithelial to mesenchymal cell transition (EMT). This is a phenomenon whereby epithelial cells in various organs (particularly the kidney) 'regress' to a more 'primitive' cellular phenotype (like that of fibroblasts). This process helps organize the formation of the body plan, and while EMT is well studied in the context of embryonic development, it also plays a role in the genesis of fibroblasts during organ fibrosis in adult tissues. Emerging evidence from studies of renal fibrosis suggests that more than a third of all disease-related fibroblasts originate from tubular epithelia at the site of injury. This process may be inhibited by the compositions of the invention Kalluri and Nielsen, J. Clin. Invest. 112:1776-1784 (2003).

Pulmonary fibrosis can appear in patients with congestive heart failure, atypical pneumonia (including Pneumocystis species) and lymphangitic spread of cancer. Environmental or occupational exposures, including inhalational exposures to inorganic dusts, e.g., silicone, asbestos, beryllios, black lung also has been recognized as causing these lung diseases. Fibrosis also may develop from exposure to protein antigens (e.g., farmer's lung, pigeon-breeder's lung, hot-tub lung) and exposure to toxic gases, fumes, aerosols, and vapors (e.g., silo-filler's disease). Exposure to radiation (ionizing radiation, frequently used in medical therapeutics also is a well-recognized cause of pulmonary fibrosis, which is also seen in causes associated with rheumatologic/connective-tissue diseases, such as: scleroderma; rheumatoid arthritis; mixed connective-tissue disease; systemic lupus erythematosus. Fibrosis also may be seen in the pulmonary-renal syndromes (i.e., Wegner or Goodpasture disease), sarcoidosis and other granulomatous diseases (e.g., berylliosis), systemic illnesses such as Hepatitis C, Inflammatory bowel disease, Acquired immunodeficiency syndrome, Idiopathic or rare DPLDs, such as the following: COP (idiopathic), Pulmonary Langerhans cell histiocytosis (rare), Eosinophilic pneumonia. In addition fibrosis may be observed in Familial IPF or sarcoidosis, tuberous sclerosis, neurofibromatosis, Niemann-Pick disease, Gaucher disease, and Hermansky-Pudlak syndrome.

Yet another area in which the therapeutic interventions of the present invention may be used is the area of fibrosis that is caused in response to various cancer treatments. For example, the therapeutic methods of the present invention will form an adjunct to radiation oncology treatment regimens. Radiation-induced pulmonary laminitis and subsequent pulmonary fibrosis are side effects of radiation therapy that phenomenon that hampers the efficacy of the radiation therapy. Typically, for example, in the treatment of cancer radiation therapy is administered at a dose of 20-85 gray. However, patient studies have shown an almost linear relationship of lung toxicity in the form of pulmonary laminitis as the radiation dose increases. Subsequently, fibrotic lesions also are seen. It is contemplated that administration of an agent that decreases the presence or activity of CCL21 and/or administration of an agent that decreases the presence or activity of CCL19 will ameliorate the development or progression of radiation-induced pulmonary laminitis and/or radiation-induced pulmonary fibrosis. In certain embodiments, it is contemplated that the therapies of the invention which decrease the presence or activity of CCL19 and/or CCL21 may be administered before and/or, after and/or concurrently with the radiation therapy. In some instances, it may be preferably to administer such agents within 1, 2, 3, 4, or 5 days after the administration of the radiotherapy.

Another cancer therapy that has been shown to lead to significant pulmonary fibrosis, is drug-induced fibrosis that occurs upon administration of bleomycin sulphate. Bleomycin is depositing in the skin and lungs and it leads to fibrosis. While cessation of drug administration and administration of corticosteroids is recommended, there is no demonstrated treatment for bleomycin-induced lung injury. It is contemplated that the therapies of the invention which decrease the presence or activity of CCL19 and/or CCL21 are administered before and/or, after and/or concurrently with bleomycin sulphate and the administration of the agents that decrease the presence or activity of CCL19 and/or CCL21 will be effective at decreasing the presence or development of pulmonary fibrosis in patients receiving bleomycin sulphate.

While bleomycin sulphate is described as an exemplary agent that causes pulmonary fibrosis, other drugs also induce pulmonary disease, an area that has been coming into sharper focus in recent years. In 1972 only 19 agents were recognized as causing pulmonary disease. A review of the literature in 2001 recognized an ever-increasing list of at least 150 agents that have been shown to cause pulmonary disease. Of these, it is known, that fibrosis can be caused by cytotoxic agents, e.g., bleomycin, busulfan, methotrexate, antibiotics, e.g., nitrofurantoin, sulfasalazine, antiarrhythmics, e.g., amiodarone, tocainide, anti-inflammatory medications, such as e.g., gold, penicillamine, illicit drugs such as e.g., crack cocaine, heroin. In specific embodiments, the methods and compositions of the invention will be useful in the treatment of fibrosis induced by Amphotericin B, bleomycin, bromocriptine, busulfan, carbamazepin, chlorambucil, cocaine, cyclophosphamide, diphenylhydantoin, ergotamine, flecainide, heroin, melphalan, methadone, methotrexate, methylphenidate, methylsergide, mineral oil, nitrofurantoin, nitrosureas, procarbazine, silicone, sulfasalazine tocainide, and the vinca alkaloid class of agents, including mitomycin and antimicrobial agents. It has been noted that with the use of nitrosureas, e.g., carmustine, lomustine, and semustine, and particularly, carmustine, up to 25% of patients that receive carmustine develop early-onset (within 36 months of initiation of carmustine therapy) develop pulmonary fibrosis.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. "Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations Compositions containing one or more agents that suppress the activity, expression or amount of CCL21 and/or CCL19 may be used to suppress fibrosis in inappropriate locations and in fibrosing disorders and chronic inflammatory conditions, inter alia. Such compositions may be applied locally to the site of the fibrotic lesion or alternatively may be administered systemically. Moreover, the compositions directed to reducing inhibiting, suppressing or otherwise abrogating the activity/effects of the CCL21 and/or CCL19 may be administered alone or in combination with other agents that may be useful in the treatment of fibrosing disorders. Such other compositions may include, e.g., corticosteroids, and other anti-inflammatory agents. Prednisone, azathioprine, and cytokine therapy with IFN gamma also may be beneficial. Combinations of these compositions with the anti-CCL21/anti-CCL19 compositions are particularly contemplated. While it has previously been suggested that the use of an immunosuppressant and a corticosteroid alone is sufficient to treat pulmonary fibrosis, it is now recognized that immunosuppressive therapy combined with corticosteroids is ineffective at treating this disease in that not only is such intervention ineffective at altering the progression of the disease, it does not lead to any increase in survival outcome. The prognosis for a subject presenting with pulmonary fibrosis is that in the absence of surgical intervention the disease is fatal. As such, the only option open to such patients is lung transplantation. The compositions and methods of the first invention therefore provide a significant advance in the therapies currently available in that they provide for a therapeutic regimen that will halt or decrease the development and/or progression of the disease.

In specific embodiments, compositions containing antibodies against CCL21 may be operable to decrease the CCL21 concentration in target locations. The doses needed to reduce CCL21 and CCL19 in people will presumably be in the low microgram range. For example antibodies in the range of approximate dosages of 5-40 micrograms/kg may be used. Ideally, these antibodies will work in the lower dosage range of 5 to 10 micrograms/kg.

IL-12, laminin-1, cross-linked IgG and IgG aggregates have been shown to suppress the differentiation of monocytes into fibrocytes (U.S. patent application No. 20050238620). Such compositions may be useful in the combinations discussed herein.

In the treatment methods the compositions may be supplied to a target location from an exogenous source, or they may be made in vivo by cells in the target location or cells in the same organism as the target location. These compositions may be isolated from donated human tissues, including biological fluids. They may be also be made as a recombinant protein in bacteria, tissue culture cells, or any other type of cells or tissues known to the art, or in whole animals. They may also be made synthetically or by any other methodology known to the art. If these compositions are made in vivo, they may be the expression product of a transgene or they may result from enhancement of production in an existing in vivo source. Levels of these compositions, if they are normally present in a target location, may also be raised by reducing their normal rates of degradation. Additionally, it may be possible to increase the fibrocyte differentiation suppression ability of these compositions, for instance by supplying cofactors.

Although the methods of the present invention are demonstrated with IIP as an exemplary fibrosing disorder. It should be understood that this disease is used as a paradigm for other fibrosing disorders. Given the teachings provided herein, those skilled in the art will appreciated that other diseases that may be treated include any diseases in which it is desirable to suppress fibrosis. As such, the methods of the invention are directed to treatment of fibrosis resulting from conditions including but not limited to: scleroderma, keloid scarring, rheumatoid arthritis, lupus, nephrogenic fibrosing dermopathy, fibrotic lesions such as those formed after Schistosoma japonicum infection, autoimmune diseases, pathogenic fibrosis, Lyme disease, stromal remodeling in pancreatitis and stromal fibrosis, asthma, idiopathic pulmonary fibrosis, chronic obstructive pulmonary disease, pulmonary fibrosis, uterine fibroids, ovarian fibrosis, other fibrocystic formations, corneal fibrosis or other eye fibrosis, such as that resulting from corneal refraction surgery, and fibrosis resulting from congestive heart failure and other post-ischemic conditions, post-surgical scarring including abdominal adhesions, wide angle glaucoma trabeculotomy. In some such fibrosing diseases fibrocytes may not represent an end-stage of fibrosis. For example, in asthma, fibrocytes further differentiate into myofibroblasts, which persist in thickened airway walls. By treatment, it should be understood that any amelioration of the symptoms of the fibrosing disease is a beneficial effect and should be considered as evidence of treatment. Thus, "treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. Treatment, prevention and ameliorating a condition, as used herein, can include, for example decreasing or eradicating a deleterious or harmful condition associated with fibrosing disease. Examples of such treatment include: decreasing bacterial infection, increasing pulmonary function, down regulation of pro-inflammatory cytokines and upregulating mononuclear cell accumulation.

In a particular embodiment, pulmonary fibrosis or other pulmonary fibrosing diseases may be treated by administration of agents that inhibit or otherwise reduce the action of CCL21 and/or CCL19. Treatment may reduce cellular growth associated with fibrosis and also collagen deposition. Treatment may prevent further fibrosis or reduce the effects of current fibrosis. The agent may be administered in any dosage amount and dosage formulation that is able to reduce at least one symptom of the disease in the patient. Administration may be intravenous and may take place every other day for a selected duration. This dose, method of administration and administration schedule may also be useful in treating other fibrosing diseases. The dosages, formulations and modes of administration may be optimized using animal models of the disease.

An exemplary model for pulmonary fibrosis is given in the examples provided below. However, those of skill are aware of other models of this fibrosing disorder. For examples, in (U.S. patent application No. 20050238620), pulmonary fibrosis was induced in rats (Sprague Dawley, containing surgically implanted jugular cathethers, Charles River Laboratories, Wilmington, Mass.) by injection of bleomycin into their lungs. Bleomycin is an antineoplastic agent that, when injected into the airway, causes fibrosis in the lungs of an animal. It is a standard way to study lung fibrosis. (Crouch, E. 1990. Pathobiology of pulmonary fibrosis. Am J Physiol Lung Cell Mol Physiol 259:L159-L184.) In such methods, to induce fibrosis, rats are anesthetized and monitored to ensure an appropriate surgical plane of anesthesia was achieved and maintained. The ventral side of the neck is prepared for incision by shaving the hair and disinfecting the area. A vertical midline incision is made in the ventral side of the neck, the neck muscles are retracted, and the trachea is exposed. 300 microliters of a 3.3 U/ml solution (1 unit) of bleomycin (Cal-biochem/EMD Biosciences, San Diego, Calif.) in sterile 0.9% saline was injected with a syringe and a 26-gauge needle into the lumen of the trachea. Control rats had saline injected. The incision is closed with two or three sutures. This procedure follows that published by Underwood et al. (2000. SB 239063, a p38 MAPK inhibitor, reduces neutrophilia, inflammatory cytokines, MMP-9, and fibrosis in lung. Am J Physiol Lung Cell Mol Physiol 279:L895-L902.) During the procedure and postoperatively the animal was maintained under a heating lamp, and then placed back in its cage once it had fully recovered. During the procedure the animal was checked to ensure it was: i) was breathing regularly, ii) had pink ears and mucous membranes, iii) did not withdraw its foot when its toes were pinched, and iv) did not blink when the eye or eyelid was touched.

In order to test the effects on an anti-CCL21 composition, the fibrosis models are injected with the anti-CCL21 composition intravenously via a jugular catheter implanted by the vendor. The composition may advantageously be formulated in physiological saline (0.9% NaCl) and passed through a 0.2 micron filter before administration.

Particularly preferred anti CCL21 compositions for use in the methods of the present invention are antibodies that are immunoreactive to CCL21. Preferably, such antibodies are monoclonal antibodies that are immunoreactive only with CCL21 and its variants and not with other chemokines. Preferably the anti-CCL21 antibody is a humanized antibody that is formulated for administration to a human subject. Anti-CCL21 antibodies for research purposes are well known to those of skill in the art. For example, R&D Systems (Minneapolis, Minn.) has a commercially available preparation, BAF457, which is a mouse recombinant anti-CC21 antibody generated in E. coli that may be used in the invention. PeproTech. (Rocky Hill, N.J.) also has anti CCL21 monoclonal antibodies. Abcam (Cambridge, U.K., and Cambridge Mass., USA), has polyclonal antibodies immunoreactive with CCL21 (e.g., Goat polyclonal to CCL21 products ab10350 and ab10364), which can readily be used reproduce tests to show that inhibition of CCL21 action in model animals ameliorates fibrosis.

As murine and goat monoclonal antibodies against CCL21 are readily available in the art, it is contemplated that such antibodies can readily be used as "templates" for generating human versions of the same for use in human therapy, For example, it is contemplated that phage display may be used to device full length or fragments of antibodies that could be used for the therapeutic methods of the invention. In other embodiments, it may be possible to generate a full length humanized mouse or goat heavy or light chain immunoglobulin that contains a human constant region, mouse or goat CDRs, and a substantially mouse or goat framework that has a number of "humanizing" amino acid alterations, which will reduce the likelihood of an adverse reaction for administration of such an antibody to a human subject. In many embodiments, a "humanized antibody" is an antibody comprising a humanized variable light chain and/or a humanized variable heavy chain. A modified antibody that has been "humanized" by the process of "humanization" binds to the same antigen as the parent antibody that provides the CDRs and is usually less immunogenic in humans, as compared to the parent antibody. Of course the above description for antibodies against CCL21 are also applicable for CCL19, for which antibodies also are available in the art.

It should be understood that as used herein, antibodies can either contain an Fc domain or not contain an Fc domain. In some embodiments, multivalent antibodies may be used as therapeutic compositions. By "multivalent antibodies" is meant recombinant antibody-like molecules that contain binding domains for more than one epitope. For example a multivalent antibody that binds both CCL21 and CCL19 may be considered to be particularly useful treatment of fibrosis. In other therapeutic compositions, the antibody-derived proteins include molecules in which an antibody Fab chain has been fused to binding domains e.g., (Fab-scFv bibodies or tribodies). These molecules are useful intermediate weight recombinant bispecific antibodies that do not containing an Fc portion. Producing antibodies that lack the Fc domain is advantageous because the presence of such a domain on an antibody-related therapeutic molecule tends to increase the serum persistence time of the molecule by protecting it from metabolism in the liver and can also crosslink other cells via its interaction with the Fc receptor, thereby giving rise to toxic side effects due to systemic triggering of immune effector cells. Thus, certain antibody related therapeutic molecules lack the Fc domain. Those of skill in the art are aware of methods of engineering such antibody-related molecules. For example, recombinant antibodies may be produced from a combination of antibody derived building blocks (such as Fc, (Fab')2, Fab, scFv, diabody) with heterodimerizing motifs in order to efficiently create multispecific antibodies.

In addition to antibodies, it is contemplated that siRNA molecules designed against CCL21 and/or CCL19 also will be useful compositions for the treatment of fibrosing disorders. Those of skill in the art are well aware that double-stranded RNA (dsRNA) can induce sequence-specific post-transcriptional gene silencing in many organisms by a process known as RNA interference (RNAi). Recent work suggests that RNA fragments are the sequence-specific mediators of RNAi (Elbashir et al., Nature, 411, 494, 2001). Interference of gene expression by these small interfering RNA (siRNA) is now recognized as a naturally occurring strategy for silencing genes in *C. elegans*, *Drosophila*, plants, and in mouse embryonic stem cells, oocytes and early embryos (Cogoni et al., Antonie Van Leeuwenhoek, 65, 205, 1994; Baulcombe, Plant Mol. Biol., 32, 79, 1996; Kennerdell, Cell, 95, 1017 1998; Timmons, Nature, 395, 854, 1998; Waterhouse et al., Proc. Natl. Acad. Sci. U.S.A. 95, 13959, 1998; Wianny and Zernicka-Goetz, Nat. Cell Biol., 2, 70, 2000; Yang et al., Mol. Cell Biol., 21, 7807, 2001; Svoboda et al., Development, 127, 4147 2000). In mammalian cell culture, a siRNA-mediated reduction in gene expression has been accomplished by transfecting cells with synthetic RNA oligonucleotides (Caplan et al., Proc. Natl. Acad. Sci. U.S.A., 98, 9742, 2001; Elbashir et al., Nature, 411, 494, 2001).

Typically, to accomplish intracellular expression of the therapeutic siRNA, an RNA molecule is constructed containing a hairpin sequence (such as a 21-bp hairpin) representing sequences directed against the gene of interest, in this case the CCL21 gene, and or the CCL19 gene. The siRNA, or a DNA sequence encoding the siRNA, is introduced to the target cell, such as a cell that is producing CCL21 at the site of a fibrotic lesion. The siRNA reduces target mRNA and gene protein expression of that agent. Use of a tissue specific promoter will achieve a beneficial tissue specific targeting of the therapeutic siRNA molecule. The construct encoding the therapeutic siRNA is configured such that the promoter and the hairpin are immediately contiguous. The promoter used in a particular construct is selected from readily available promoters known in the art, depending on whether inducible, tissue or cell-specific expression of the siRNA is desired. The construct is introduced into the target cell, such as by injection, allowing for diminished target-gene expression in the cell.

Thus, in exemplary embodiments, the present invention provides a vector (i.e., a viral vector typically used in recombinant gene expression and/or delivery, e.g., adenoviral, lentiviral, adeno-associated viral (AAV), retroviral, poliovirus, herpes simplex virus (HSV) or murine Maloney-based viral vector and the like) comprising an expression cassette, wherein the expression cassette comprises an isolated nucleic acid sequence encoding a small interfering RNA molecule (siRNA) targeted against CCL21. The nucleic acid structure of CCL21 is well known to those of skill in the art, as is the structure of CCL19, see e.g., Genbank Accession No. AB002409, which describes the mRNA sequence of human CCL21; Genbank Accession No. NM_006274, which describes the mRNA sequence of human CCL21; the Genbank accession No. for CCL21 from rhesus monkeys is given in NM_001032855; the sequences for pig, mouse, and dogs also are available in Genbank as of the filing of this application. These sequences can all be prepared and siRNA can be designed against those regions of the molecule determined to be important for the functional expression of the CCL21 (note that the related protein sequence disclosures may be used to prepare recombinant antibodies of the same and generated antibodies against the same). The siRNA may be targeted to any 10-30 contiguous stretch of nucleic acids along such a nucleic acid sequence, and especially useful will be that sequence that is important for the functional expression of the chemokine. The siRNA may form hairpin structure comprising a duplex structure and a loop structure. The loop structure may contain from 4 to 10 nucleotides, such as 4, 5 or 6 nucleotides. The duplex is preferably less than 30 nucleotides in length, such as from 19 to 25 nucleotides. The siRNA may further comprises an overhang region. Such an overhang may be a 3' overhang region, a 5' overhang region, or both 3' and 5' overhang regions. The overhang region may be, for example, from 1 to 6 nucleotides in length. The expression cassette may further comprise a promoter. Examples of promoters include regulatable promoters and constitutive promoters. For example, the promoter may be a CMV, RSV, or polIII promoter. The expression cassette may further comprise a polyadenylation signal, such as a synthetic minimal polyadenylation signal. The nucleic acid sequence may further comprise a marker gene.

Of course in addition to compositions directed against CCL21 and/or CCL19, the compositions also may be directed against CCR7, the receptor for such chemokines. Further, combination therapies are particularly contemplated, in which the treatment modes directed against reducing the effects/activity of CCL21 are combined with treatment modes directed against reducing the effects/activity of the receptor. Other specific combination therapies particularly contemplated are those in which the treatment methods based on reducing the activity of the CCL21 in the fibrosing disease are combined with preexisting treatments for fibrosis. For example, at present, cyclophosphamide, either alone or in combination with mycophenolate mofetil (MMF) or prednisolone, or other corticosteroids has proven effective at ameliorating pulmonary fibrosis. Clinical programs also hasv shown promising results with the safety and efficacy of bosentan (Tracleer®) in the idiopathic and scleroderma-related form of pulmonary fibrosis. Azathioprine may also have a role in stabilizing lung function and improving symptoms in fibrotic disorders. Cytokine (IFN-gamma) therapy also may be a useful treatment method for the treatment of fibrosing disorders. Any such compositions may be used in combination with anti-CCL21-based therapies and/or anti-CCL19-based therapies (note that by "anti-CCL21-based" or "anti-CCL19" therapies is meant both antibody therapies as well as therapies that employ siRNA molecules) in order to reduce, eliminate or otherwise abrogate the symptoms of the fibrosis.

Regardless of whether the antibodies are generated against a specific antigen in an animal or are chimeric antibodies prepared through phage display and antibody engineering techniques, such antibodies will ultimately be formulated into pharmaceutical formulations for the treatment of fibrotic disorders. Likewise, the siRNA compositions also will ultimately be formulated into compositions for the treatment of these disorders. Local deliver of the compositions will be preferred, but it is contemplated that systemic delivery also is possible.

Pharmaceutical compositions for administration according to the present invention can comprise any of the anti-CCL21 and/or anti-CCL19 based compositions discussed above. The pharmaceutical compositions also include another agent that is used for the treatment of a disorders of surfactant metabolism, e.g., bronchodilators, particularly if the patient manifests evidence of airway reactivity is present as well as, mucolytic agents such as acetylcysteine, trypsin, and ambroxol, and/or GM-CSF, corticosteroids and other anti-inflammatory agents. Each of these preparations is in some aspects provided in a pharmaceutically acceptable form optionally combined with a pharmaceutically acceptable carrier. These compositions are administered by any methods that achieve their intended purposes. Individualized amounts and regimens for the administration of the compositions for the inhibition, abrogation, or other in the effects of CCL21 or CCL19 at the fibrotic lesion using the methods of the present invention are determined readily by those with ordinary skill in the art using assays that are used for the diagnosis of the disorder and determining the level of effect a given therapeutic intervention produces.

In the treatment of IIP, any of the protocols, formulations, routes of administration and the like that have previously been used in the treatment of lung disorders may readily be modified for use in the present invention. In some cases, mechanical ventilation may be appropriate, where shortness of breath is particularly extreme. Such ventilation may include high-frequency oscillatory ventilation (HFOV) or other unconventional forms of mechanical ventilation.

Compositions within the scope of this invention include all compositions comprising at least one agent for decreasing the effects or activity of CCL21 in an amount effective to achieve its intended purpose of reducing, inhibiting, preventing or diminishing the activity of the CCL21 as exemplified by a decrease or reduction in the amount of fibroblasts at a fibrotic disease lesion site. In some aspects, such treatment will result in an alleviation of one or more symptoms of IIP.

In other aspects, the compositions used in the present invention are administered using an inhalant or orally.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of the dose if the patient has a low body weight.

The total dose of therapeutic agent is administered in multiple doses or in a single dose. In certain embodiments, the compositions are administered alone, in other embodiments the compositions are administered in conjunction with other therapeutics directed to the disease or directed to other symptoms thereof.

In some aspects, the compositions of the invention are formulated into suitable pharmaceutical compositions, i.e., in a form appropriate for in vivo applications in the therapeutic intervention of fibrosing disease. Generally, this will entail preparing compositions that are essentially free of pyrogens, as well as other impurities that could be harmful to humans or animals. In some aspects, the compositions are prepared for administration directly to the lung. These formulations are for oral administration via an inhalant, however, other routes of administration are contemplated (e.g. injection and the like). The finding that CCL21 is highly expressed in IIP fibroblasts but not in normal fibroblasts or other tissues leads to a conclusion that a main site of this chemokine is integrally involved in the formation of the fibrotic lesions, this appears to be particularly true in IIP. As such, it is contemplated that formulations and routes of administration that facilitate the compositions to readily be administered to lung tissue will be particularly useful.

One will generally desire to employ appropriate salts and buffers to render the compositions stable and allow for uptake of the compositions at the target site. Generally the protein compositions of the invention are provided in lyophilized form to be reconstituted prior to administration. Alternatively, the compositions may be likely formulated into tablet or other oral delivery form. Buffers and solutions for the reconstitution of the therapeutic agents may be provided along with the pharmaceutical formulation to produce aqueous compositions of the present invention for administration. Such aqueous compositions will comprise an effective amount of each of the therapeutic agents being used, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also are incorporated into the compositions.

Methods of formulating proteins and nucleic acid for therapeutic administration also are known to those of skill in the art. Administration of these compositions according to the present invention will be via any common route so long as the target tissue is available via that route. Most commonly, these compositions are formulated for oral administration, such as by an inhalant. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also is used particularly when oral administration is problematic. The treatment may consist of a single dose or a plurality of doses over a period of time.

In certain embodiments, the active compounds are prepared for administration as solutions of free base or pharmacologically acceptable salts in water suitably mixed with a surfactant, such as hydroxypropylcellulose. Dispersions also are prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also are incorporated into the compositions.

In some aspects, the compositions of the present invention are formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also are derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. In certain embodiment, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions. Any such dosages can readily be optimized using models of the disease such as those rodent models described herein.

It will be appreciated that the pharmaceutical compositions and treatment methods of the invention are useful in fields of human medicine and veterinary medicine. Thus the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The present invention also contemplated kits for use in the treatment of fibrosing disorders. Such kits include at least a first composition comprising the anti-CCL21 and/or anti-CCL19 based therapies described above in a pharmaceutically acceptable carrier. Another component is a second therapeutic agent for the treatment of the disorder along with suitable container and vehicles for administrations of the therapeutic compositions. The kits may additionally comprise solutions or buffers for effecting the delivery of the first and second compositions. The kits may further comprise catheters, syringes or other delivering devices for the delivery of one or more of the compositions used in the methods of the invention. The kits may further comprise instructions containing administration protocols for the therapeutic regimens.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials Used to Show Role of CCR7 in Interstitial Idiopathic Pneumonia Patients suspected of having IIP, as determined from a compilation of clinical, physiological, radiographical, and pathological findings (Flaherty et al., Am. J. Med., 110:278-282 (2001); Flaherty et al., Curr. Opin. Pulm. Med., 6:404-410 (2000); Kazerooni et al., AJR Am. J. Roentgenol., 169: 977-983 (1997); American Thoracic Society, European Respiratory Society (ATS/ERS), Am. J. Respir. Crit. Care Med., 165:277-304 (2002)). None of the patients enrolled in the present study had undergone previous biopsy surgery or received treatment for IIP. SLBs were performed as part of the evaluation for the University of Michigan Specialized Center of Research in the pathobiology of fibrotic lung disease between May 2000 and August 2004. Histologically normal lung biopsies with no pathological evidence of disease were obtained from the distant margins of resected specimens in patients undergoing thoracic resection for lung cancer. Each SLB was processed separately using sterile technique in a laminar flow hood and processed for molecular, protein, and immunohistochemical analysis (see below).

Preparation of RNA and cDNA from SLBs.

The portion of each SLB used for molecular analysis was snap frozen in liquid nitrogen and stored at 280° C. For RNA isolation, these samples were thawed on ice, and mechanically homogenised in TRIzolH reagent (Invitrogen Life Technologies, Carlsbad, Calif., USA) and total RNA was then prepared according to the manufacturer's instructions. Purified RNA from SLBs was subsequently reverse transcribed into cDNA using a BRL reverse transcription kit and oligo (dT) 12-18 primers. The amplification buffer contained 50 mM KCl, 10 mM Tris/HCl (pH 8.3), and 2.5 mM $MgCl_2$.

Gene Array Analysis.

Non-Rad GEArray gene array membranes from SuperArray Inc (Bethesda, Md., USA) were used to analyse changes in gene profiles for human chemokines and chemokine receptors, as described previously. (Choi et al., Am. J. Respir. Crit. Care Med., 170:508-515 (2004)) Glyceraldehyde 3-phosphate dehydrogenase (GAPDH) was used as the internal positive control because it was consistently expressed in all SuperArrays analyzed in the present study.

Real time Taqman PCR analysis. Human CCR7, CXCR4, CCL19, CCL21, and CXCL12 gene expression in IIP and normal margin SLBs was analyzed by a real time quantitative reverse transcription polymerase chain reaction (PCR) procedure using an ABI PRISM 7700 sequence detection system (Applied Biosystems, Foster City, Calif., USA), as described previously. (Jakubzick et al., Am. J. Pathol., 162:1475-1486 (2003)) The cDNAs from upper and lower lobe SLBs were analyzed for chemokine receptor, chemokine, and GAPDH (an internal control) expression. All primers and probes used were purchased from Applied Biosystems. Chemokine gene expression was normalised to GAPDH before the fold change in chemokine expression was calculated. The fold increases in cytokine gene expression were calculated by comparing gene expression in all patients with that detected in the upper or lower lobes of the normal margin tumour patient group.

ELISA Analysis. Human CCL19, CCL21, and CXCL12 concentrations were measured in 50 ml cell free supernatant samples from homogenised IIP and normal margin SLBs using a standardized sandwich enzyme linked immunosorbent assay (ELISA) technique (R&D Systems, Minneapolis, Minn., USA). Recombinant human cytokines were used to generate standard curves from which the concentrations present in the samples were derived. The limit of detection for CCL19, Immunohistochemistry Routine immunochemistry techniques were used to detect CCR7, CXCR4, CD45, CD34, and aSMA) in SLBs, as described previously. (Jakubzick et al., J. Clin. Pathol., 57:477-486 (2004)) The following target antibodies and their appropriate isotype controls were used: mouse antihuman CCR7 antibody and mouse IgMk purchased from BD Biosciences PharMingen (San Diego, Calif., USA); mouse antihuman CXCR4 and mouse IgG2B purchased from R&D Systems; mouse antihuman CD45, CD34, and collagen 1 antibodies purchased from Abcam (Cambridge, Mass., USA) and mouse IgG1 purchased from R&D Systems. Upper and lower lobe SLBs from 10 patients with UIP, six with NSIP, and five with RBILD were analyzed using these immunohistochemical techniques. The normal margins from resected tumours were analyzed in five patients. Serial sections (5 mm thick) were analyzed from each SLB and colocalisation of CCR7 with other antigens was performed on immediately adjacent serial sections.

Example 2

Results Showing Role of CCR7 in Interstitial Idiopathic Pneumonia

Figures 1A, 1B:
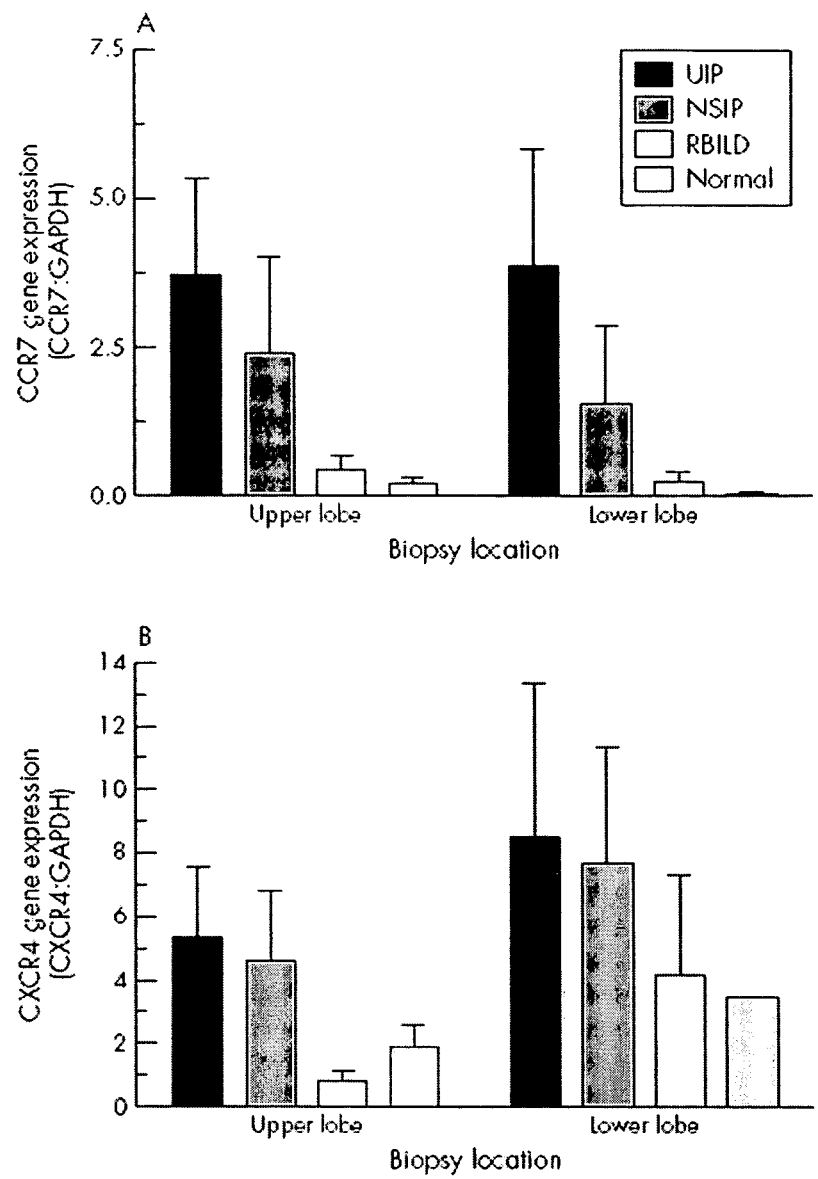
FIG. 1 SuperArray gene analysis of (A) CCR7 and (B) CXCR4 gene expression in upper and lower lobe surgical lung biopsies from UIP (n=7), NSIP (n=6), RBILD (n=6), and normal margin (n=5) tumour patient groups. The data shown are mean (SEM). No significant differences were detected. CCR7, CC chemokine receptor 7; CXCR4, CX chemokine receptor 4; GAPDH, glyceraldehyde 3-phosphate dehydrogenase; NSIP, non-specific interstitial pneumonia; RBILD, respiratory bronchiolitis/interstitial lung disease; UIP, usual interstitial pneumonia.
Figures 2A, 2B, 2C:
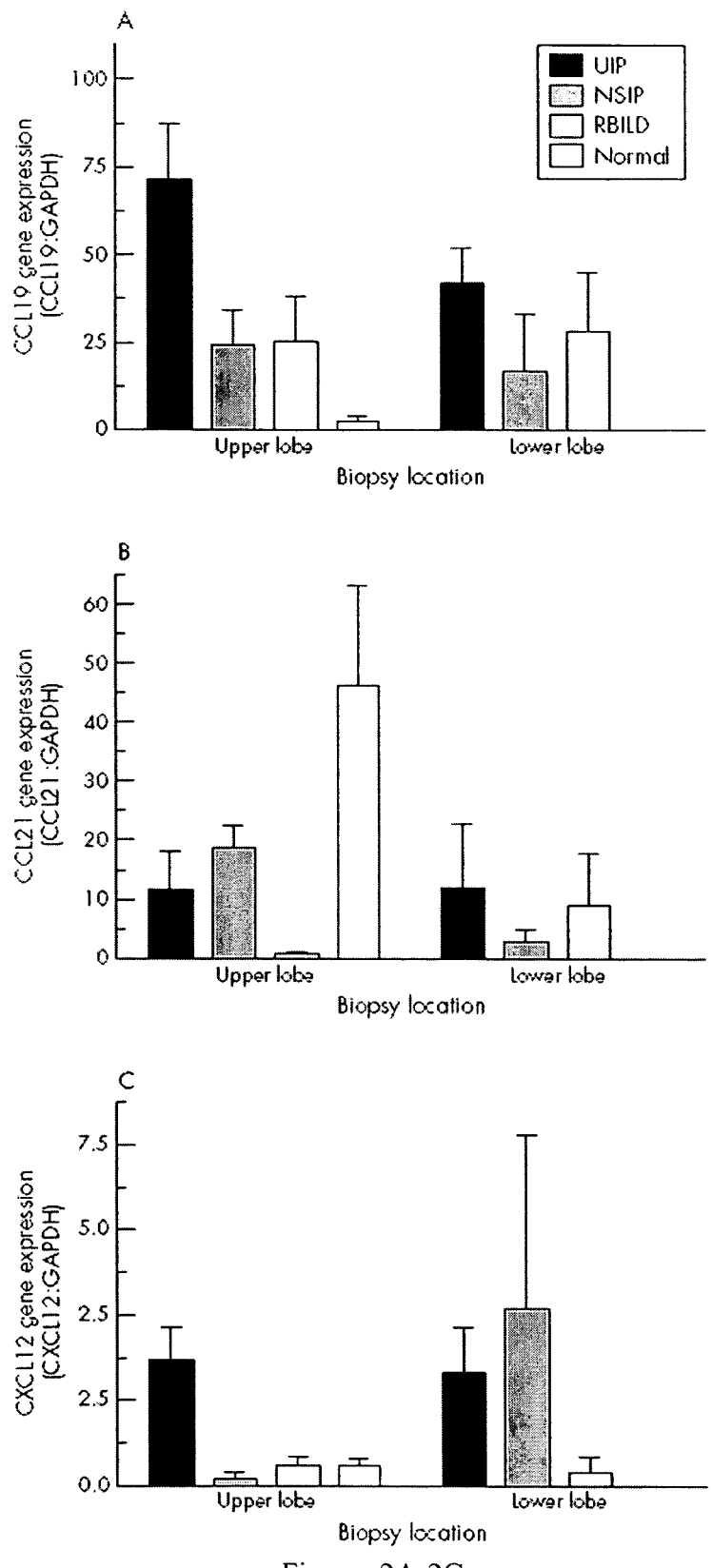
FIG. 2 SuperArray gene analysis of (A) CCL19, (B) CCL21, and (C) CXCL12 gene expression in upper and lower lobe surgical lung biopsies from UIP (n=7), NSIP (n=6), RBILD (n=6), and normal margin (n=5) tumour patient groups. The data shown are mean (SEM). No significant differences were detected. CCL, CC chemokine receptor ligand; CXCL, CX chemokine receptor ligand; GAPDH, glyceraldehydes 3-phosphate dehydrogenase; NSIP, non-specific interstitial pneumonia; RBILD, respiratory bronchiolitis/interstitial lung disease; UIP, usual interstitial pneumonia.

SuperArray analysis of CCR7, CXCR4, CCL19, CCL21, and CXCL12 transcripts in IIP and normal margin SLBs The presence of CCR7 and CXCR4 in IIP and normal margin SLBs was analyzed using a specific SuperArray GEArray. Although this is a qualitative and not a quantitative technique, the expression of CCR7 (FIG. 1A) and CXCR4 (FIG. 1B) was normalised to that of GAPDH, and the values are shown for both receptors. The highest relative expression of CCR7 and CXCR4 was seen in upper and lower lobe biopsies from the UIP patient group (n=7). Lower and upper lobe biopsies from the NSIP (n=6), RBILD (n=6), and normal margin (n=5) tumour patient groups were similarly analyzed. Although significant differences were not detected, overall, the relative expression of both chemokine receptors appeared to follow a disease severity pattern as follows: UIP . NSIP . RBILD . normal margin. The two CCR7 ligands identified to date are CCL19 (Yoshida et al., J. Biol. Chem., 272:13803-13809 (1997)) and CCL21. (Campbell et al., J. Cell Biol., 141:1053-1059 (1998)) CCL19 (or ELC, exodus-3, and CKb-1134) is constitutively expressed in afferent lymph endothelium and the T cell area of lymph nodes, thereby accounting for its major role in the movement of dendritic cells and T cells to these immune sites. (Sallusto et al., Eur. J. Immunol., 29:1617-1625 (1999)) Concurrent studies showed that CCL21 (or SLC, exodus-2, TCA-4, and CKb-99) had similar functions and a similar pattern of expression.33 However, both chemokines have been detected in the lung (Gunn et al., Proc. Natl. Acad. Sci. USA, 95:258-263 (1998)) and kidney, (Banas et al., J. Immunol., 168:4301-4307 (2002)) suggesting that they may have roles outside immune surveillance. The analysis of the relative transcript expression of CCL19 revealed higher amounts of this CCR7 ligand in UIP upper and lower lobe biopsies (FIG. 2A). Similar amounts of CCL19 transcript were detected in NSIP and RBILD biopsies, and the lowest amounts were seen in normal margin biopsies. However, no clear patterns of CCL21 (FIG. 2B) and CXCL12 (FIG. 2C) transcript expression were seen among the IIP and normal margin biopsies.

Figures 3A, 3B:
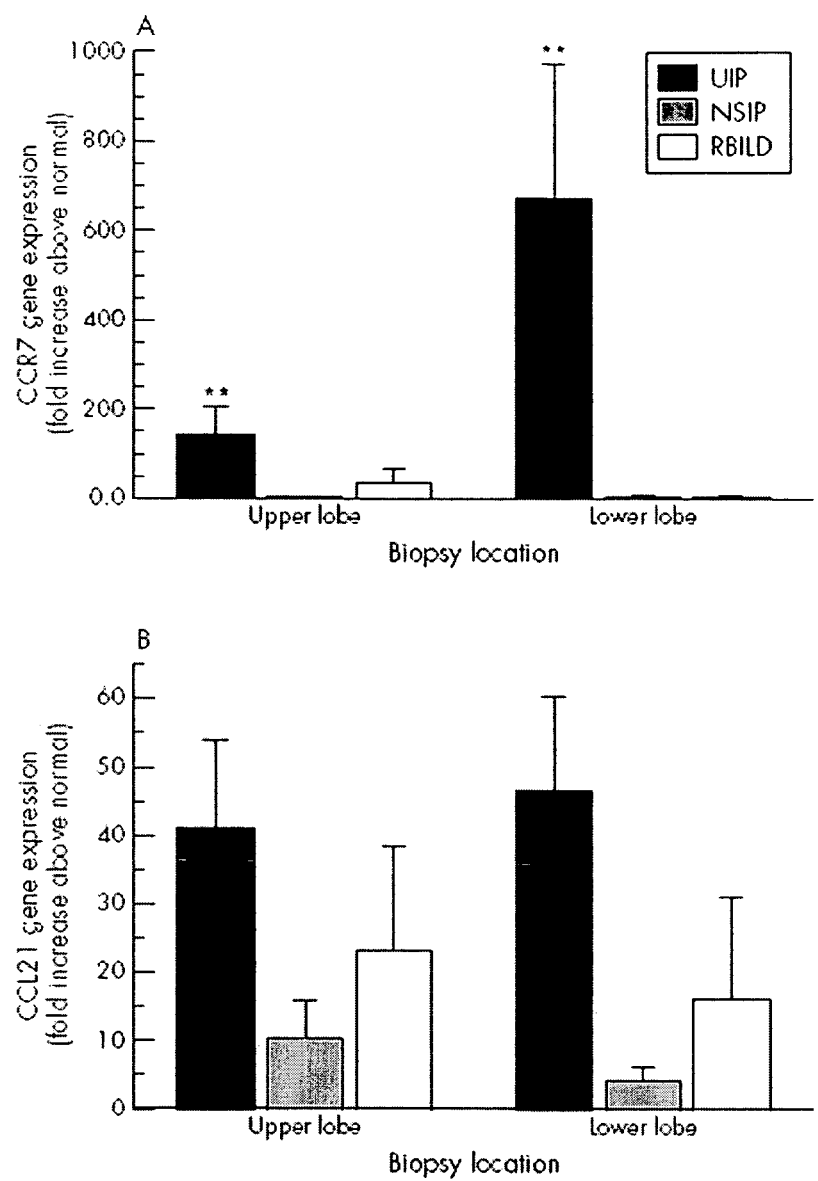
FIG. 3 Quantitative Taqman polymerase chain reaction analysis of CCR7 and CCL21 gene expression in upper and lower lobe surgical lung biopsies from patients with UIP (n=18), NSIP (n=8), RBILD (n=6), and normal margins (n=6). The data shown are mean (SEM). **p (0.01 compared with the appropriate lobe from the normal margin tumour patient group. CCR7, CC chemokine receptor 7; CCL21, CC chemokine receptor 4 ligand; NSIP, non-specific interstitial pneumonia; RBILD, respiratory bronchiolitis/interstitial lung disease; UIP, usual interstitial pneumonia.

Quantitative real time PCR analysis of CCR7, CXCR4, CCL19, CCL21, and CXCL12 transcript expression in IIP and normal margin SLBs Taqman real time PCR analysis of upper and lower lobe biopsies from the four patient groups revealed a significant increase in CCR7 transcript expression in both upper and lower SLBs from patients with UIP (n=18) compared with the appropriate biopsy from the normal margin tumour patient group (n=5) (FIG. 3A). Mean CCR7 transcript values were approximately 146 (SEM, 58) and 675 (SEM, 300) fold higher in upper and lower lobe UIP SLBs, respectively, compared with the appropriate lobe from the normal margin patient group. Approximately fivefold greater CCR7 transcript expression was detected in the lower lobe UIP biopsies compared with upper lobe UIP biopsies. Mean CCR7 transcript values were increased fourfold (SEM, 1) in both upper and lower lobe NSIP SLBs compared with normal margin SLBs. Mean CCR7 transcript values were also increased in RBILD SLBs relative to normal margin SLBs: 36 (SEM, 28) fold in upper SLBs and 4.4 (SEM, 3.2) fold in lower lobe biopsies. Increases in CCR7 transcript expression in NSIP and RBILD SLBs relative to normal margin SLBs were not significant.

These findings were unique to CCR7 because Taqman PCR analysis of CXCR4 found no significant increase in CXCR4 transcript expression in IIP SLBs relative to normal margin SLBs (data not shown). Finally, no clear patterns or significant differences in CCL19 (data not shown), CCL21 (FIG. 3B), and CXCL12 (data not shown) transcript expression were apparent or detected among the IIP and normal margin tumour patient groups examined. However, the greatest increase in CCL21 transcript expression relative to the normal margin tumour patient group was seen in the upper and lower lobe biopsies from the UIP patient group (more than 40 times higher than normal margin SLB values). Greater increases in CCL21 transcript expression were seen in upper and lower RBWLD SLBs compared with NSIP SLBs. Together, these data suggested that CCR7 transcript expression was very much increased in UIP, and that increases in CCR7 transcript expression were also present in less severe forms of IIP.

Figures 4A, 4B, 4C:
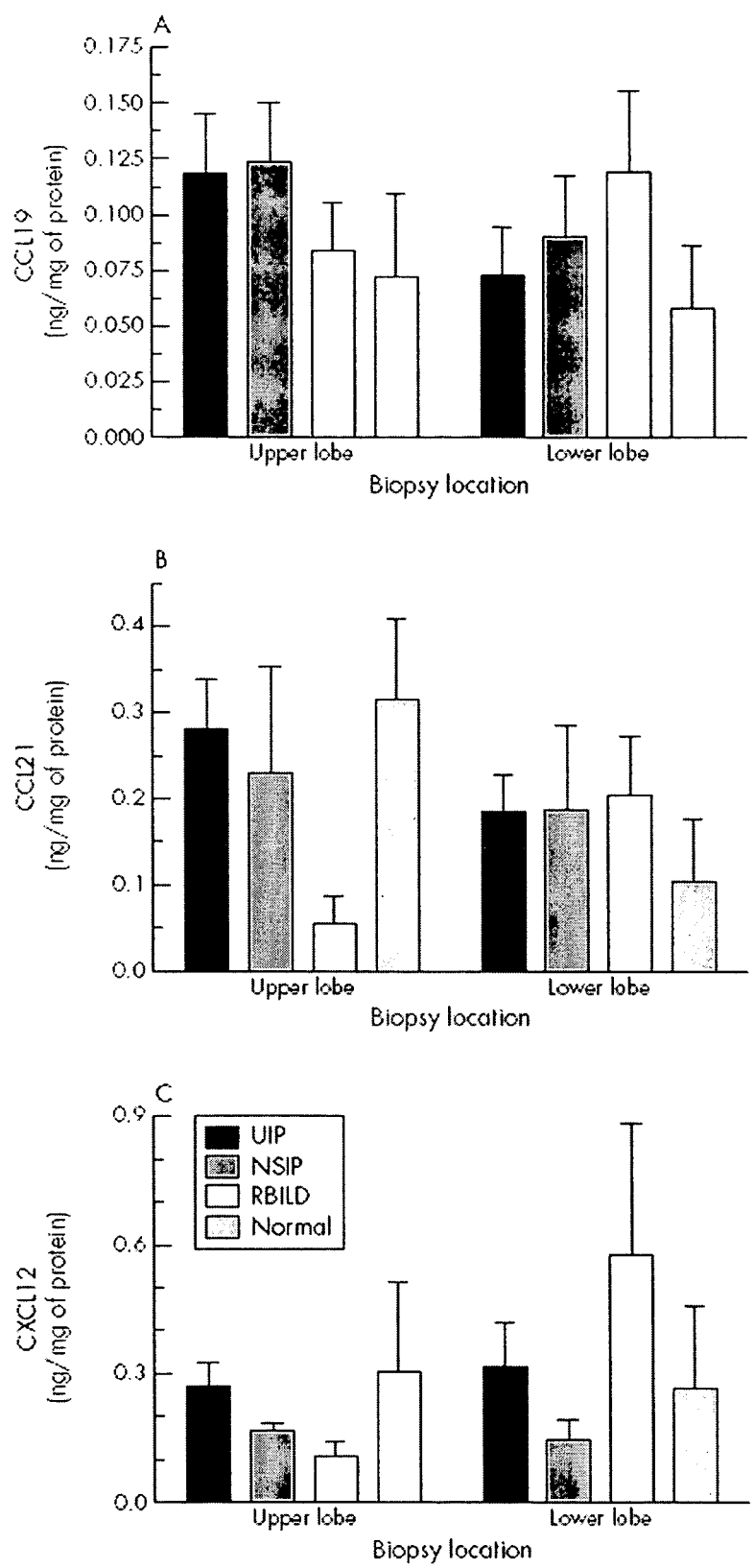
FIG. 4 Enzyme linked immunosorbent assay analysis of CCL19, CCL21, and CXCL12 in upper and lower lobe surgical lung biopsies from patients with UIP (n=18), NSIP (n=6), RBILD (n=6), and normal margins (n=5). The data shown are mean (SEM). CCL, CC chemokine receptor ligand; CXCL, CX chemokine receptor ligand; NSIP, non-specific interstitial pneumonia; RBILD, respiratory bronchiolitis/interstitial lung disease; UIP, usual interstitial pneumonia.

ELISA analysis of CCL19, CCL21, and CXCL12 protein in IIP and normal margin SLBs FIG. 4 shows the concentrations of CCL19 (FIG. 4A), CCL21 (FIG. 4B), and CXCL12 (FIG. 4C) proteins in cell free supernatants from homogenised SLBs. No clear patterns of CCL expression were noted, and no significant differences were detected among the patient groups analyzed. Thus, these data suggested that the fibrotic events in IIP were not associated with the increased generation of CCR7 and CXCR4 ligands within the lung.

Figures 5A, 5B, 5C, 5D, 5E, 5F, 5G, 5H:
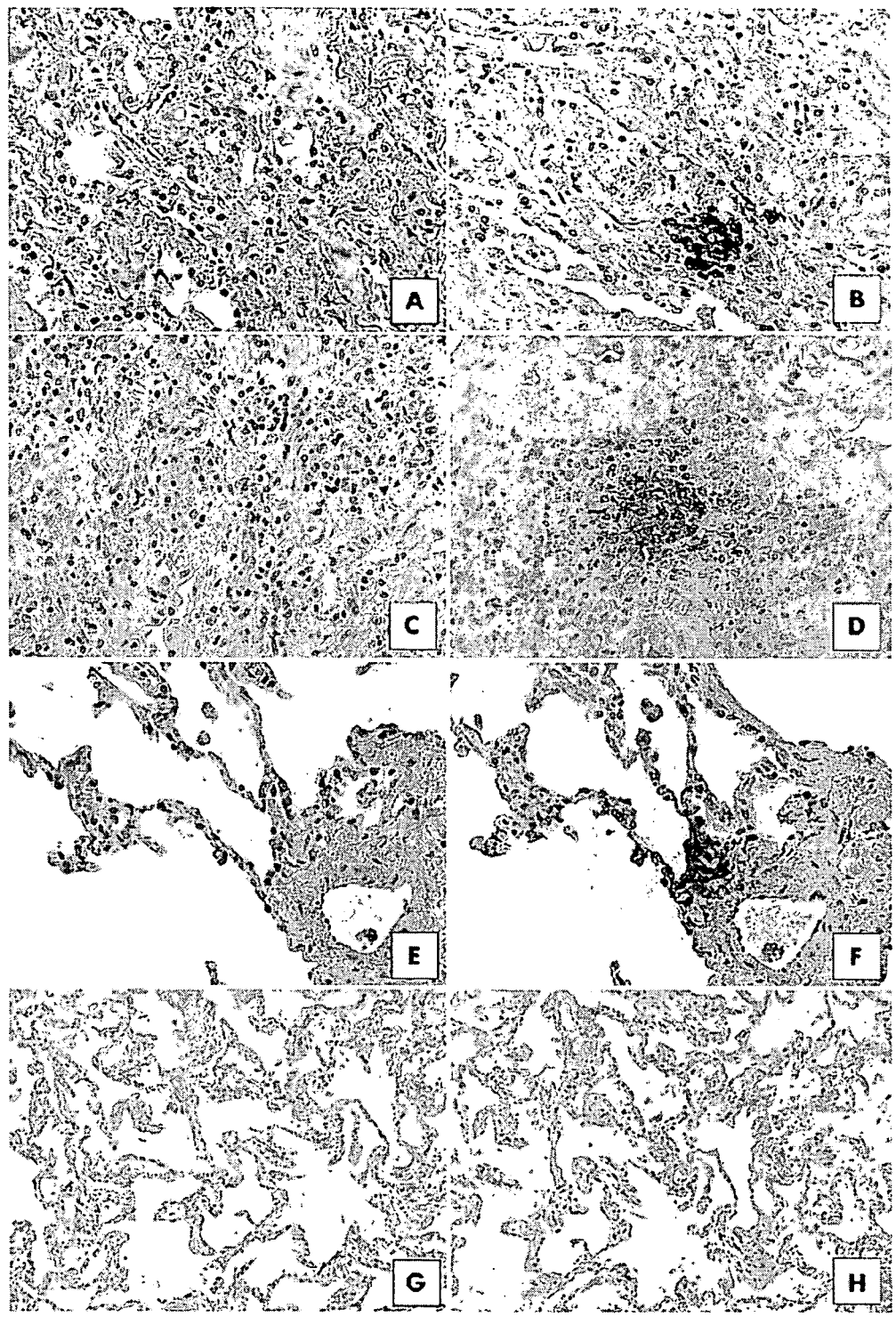
FIG. 5 Representative immunohistochemical analysis of CCR7 in SLBs from (A, B) UIP, (C, D) NSIP, (E, F) RBILD, and (G, H) normal margin tumour patient groups. Panels (A), (C), (E), and (G) show control staining. CCR7 immunoreactivity (red staining) was seen in focal areas in SLBs from (B) UIP, (D) NSIP, and (F) RBILD, but not (H) normal margins. Original magnification, 6200. CCR7, CC chemokine receptor 7; NSIP, nonspecific interstitial pneumonia; RBILD, respiratory bronchiolitis/interstitial lung disease; SLB, surgical lung biopsy; UIP, usual interstitial pneumonia.

Focal interstitial CCR7 protein expression in IIP SLBs The SuperArray and real time PCR transcript analysis suggested that CCR7 expression was much higher in IIP SLBs than in normal margin SLBs; therefore, immunohistochemical analysis of whole lung sections from IIP and normal margin SLBs were undertaken to confirm these observations. As shown in FIG. 5, focal interstitial CCR7 expression was seen in SLBs from the UIP, NSIP, and RBILD patient groups. Although CCR7 expression was seen in macrophages in the patients with RBILD (FIG. 5F), the focal interstitial pattern of CCR7 expression was not exclusively associated with immune cells in UIP (FIG. 5B) and NSIP biopsies (FIG. 5D). Multiple areas of focal CCR7 protein expression were present in interstitial areas of all upper and lower lobe SLBs from the UIP patient group (n=10). It is of note that the foci of CCR7 expression did not exclusively comprise fibroblasts—other cells, including mononuclear and epithelial cells, also appeared to express this chemokine receptor. Both NSIP and RBILD subtypes expressed less CCR7 than the more severe subtype UIP. Although 50% of these biopsies showed CCR7 staining, far fewer focal areas of CCR7 expression were seen in upper and lower lobe SLBs in the NSIP patient group (n=6). CCR7 was frequently restricted to blood vessels and mononuclear cells in three quarters of the RBILD (n=5) SLBs, but CCR7 staining was infrequently detected in interstitial areas of the biopsy samples from this IIP group. In contrast to the prominent staining seen in UIP SLBs, no CCR7 expression was detected by immunohistochemical analysis in upper and lower SLBs from patients with normal margins (n=5) (FIG. 5H).

Figures 6A, 6B, 6C, 6D, 6E, 6F, 6G, 6H:
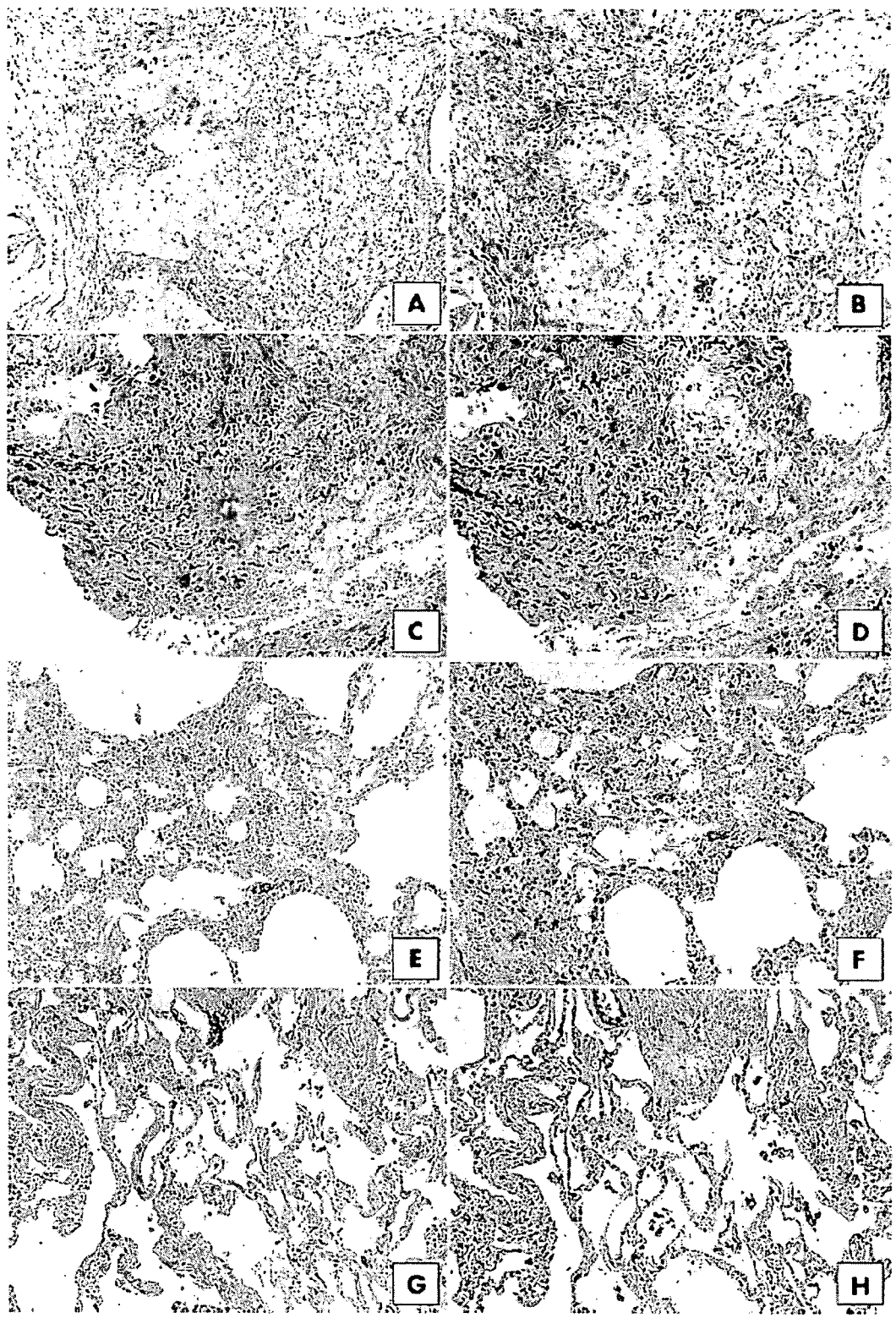
FIG. 6 Representative immunohistochemical analysis of CXCR4 in SLBs from (A, B) UIP, (C, D) NSIP, (E, F) RBILD, and (G,H) normal margin tumour patient groups. Panels (A), (C), (E), and (G) show control staining. CXCR4 immunoreactivity (red staining) was seen in mononuclear cells present in IIP and normal margin SLBs. Original magnification, 6200. CXCR4, CX chemokine receptor 4; NSIP, nonspecific interstitial pneumonia; RBILD, respiratory bronchiolitis/interstitial lung disease; SLB, surgical lung biopsy; UIP, usual interstitial pneumonia.

In the same IIP and normal margin SLBs analyzed for CCR7, CXCR4 staining appeared to be limited to immune cells, and more importantly, the expression of this chemokine receptor was not focal and did not differ among the four patient groups analyzed. All IIP and normal margin biopsies analyzed showed strong mononuclear cell associated CXCR4 expression. This is highlighted in FIG. 6, which shows representative CXCR4 staining in UIP (FIG. 6B), NSIP (FIG. 6D), RBILD, (FIG. 6F), and normal margin (FIG. 5D) SLBs. Thus, an immunohistochemical survey revealed that CCR7, unlike CXCR4, was prominently expressed in IIP SLBs but not in normal margin SLBs, and that CCR7 expression appeared to be localised to focal interstitial areas in IIP.

Figures 7A, 7B, 7C, 7D, 7E, 7F:
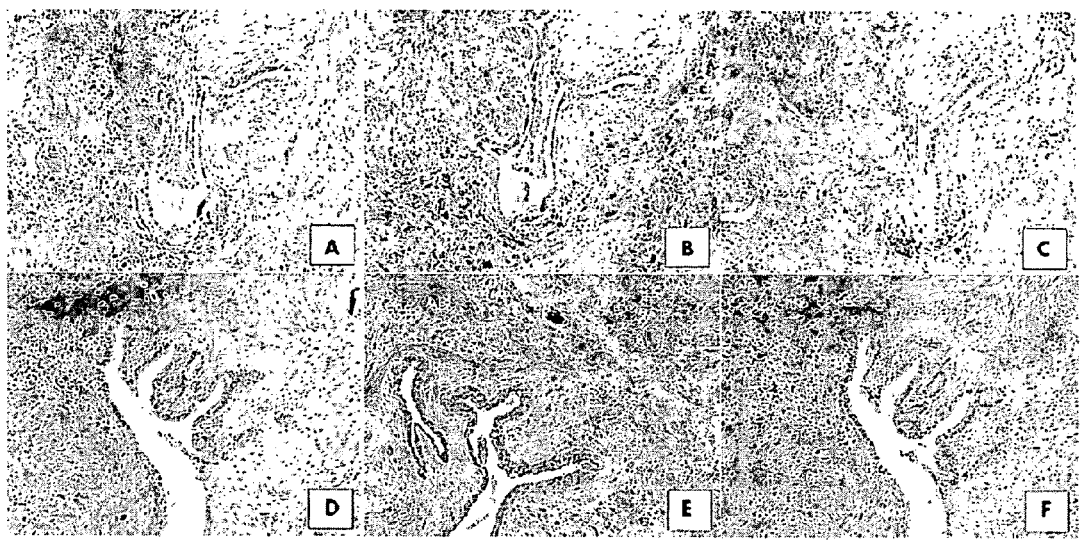
FIG. 7 Representative immunohistochemical analysis of (B, E) CCR7 and (C, F) CD45 in serial histological sections from (A-C) UIP and (D-F) NSIP patient groups. Panel (A) and (D) show control staining. In UIP SLBs, CCR7 immunoreactivity (red staining in B) partially overlapped with CD45 immunoreactivity (C), with most of the dual staining associated with mononuclear cells (C). (A, F) In serial histological sections, CCR7 and CD45 did not appear to colocalise in NSIP SLBs. Original magnification, 6200. CCR7, CC chemokine receptor 7; NSIP, non-specific interstitial pneumonia; SLB, surgical lung biopsy; UIP, usual interstitial pneumonia.
Figures 8A, 8B, 8C, 8D, 8E, 8F, 8G, 8H:
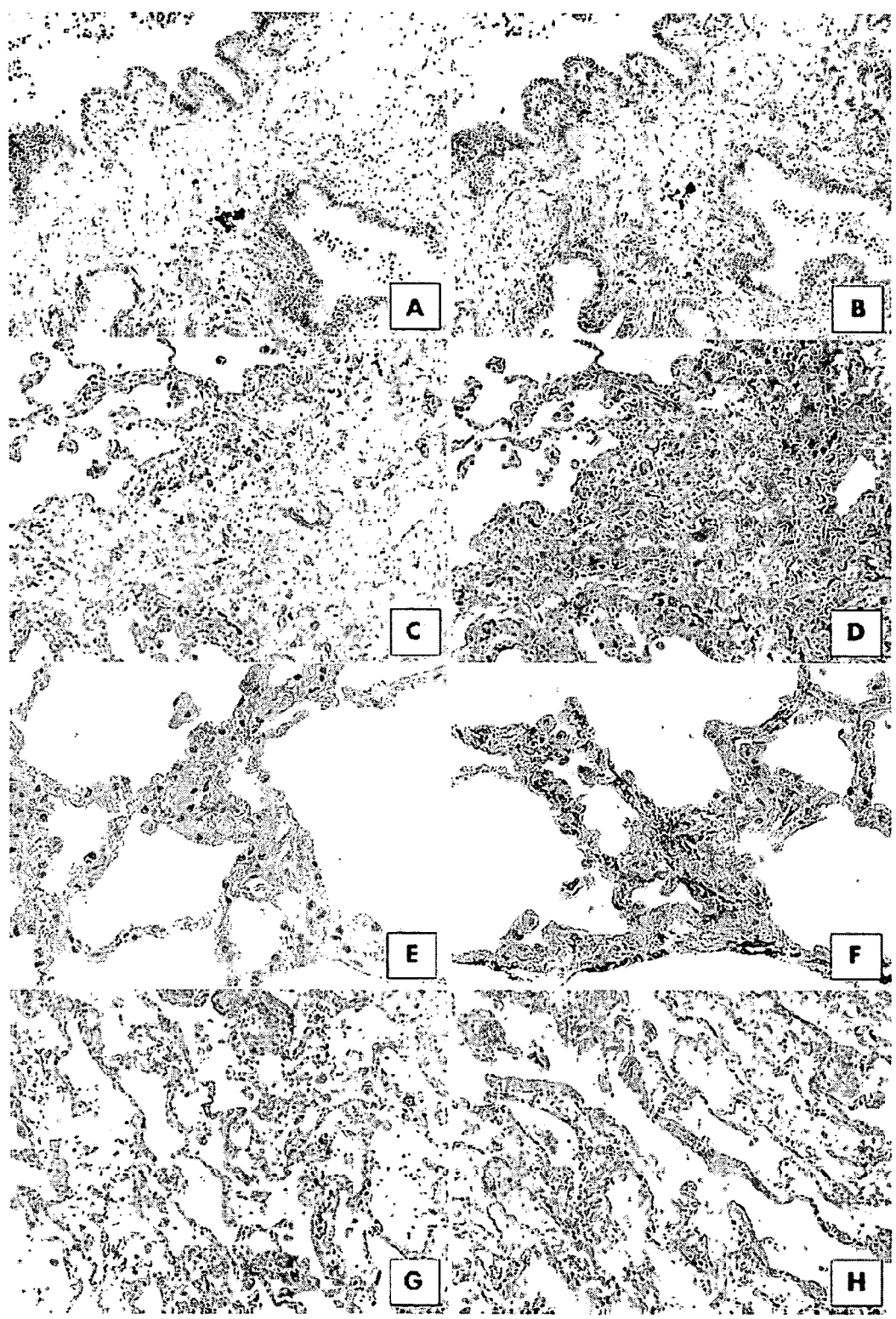
FIG. 8 Representative immunohistochemical analysis of CD34 in SLBs from (A, B) UIP, (C, D) NSIP, (E, F) RBILD, and (G, H) normal margin tumour patient groups. Panels (A), (C), (E), and (G) show control staining. CD34 immunoreactivity (red staining) was seen in interstitial areas in all patient SLBs. (D) The highest expression of CD34 was seen in SLBs from the NSIP patient group. Original magnification, 6200. NSIP, nonspecific interstitial pneumonia; RBILD, respiratory bronchiolitis/interstitial lung disease; SLB, surgical lung biopsy; UIP, usual interstitial pneumonia.

To elucidate the identity of the cells making up the CCR7 positive areas in IIP SLBs, additional staining experiments were performed on serial sections for the expression of CD45 and CCR7 (FIG. 7). Upon examination of UIP SLBs, the immunohistochemical expression of CCR7 (FIG. 7B) was found to overlap partly with that of CD45 (FIG. 7C). Cells expressing both CCR7 and CD45 appeared to be mononuclear cells. In contrast, although CCR7 was highly expressed in NSIP biopsies (FIG. 7E), the immunolocalisation of this chemokine receptor did not correspond with that of CD45. Similar immunohistochemical studies in RBILD SLBs revealed the same lack of colocalisation of CCR7 and CD45 (not shown). Therefore, dual CD45 and CCR7 expression on mononuclear cells was present in UIP but not in other forms of IIP. As described above, CD34 is a haemopoietic stem cell antigen that has been identified on peripheral blood fibrocytes. (Abe et al., J. Immunol., 166:7556-7562 (2001)) The inventors next examined whether this marker could be identified in histological sections from IIP and normal margin biopsies (FIG. 8). Interestingly, very little CD34 expression was seen in UIP biopsies (FIG. 8B), and when it was detected this antigen was predominately localised to the interstitial areas of the biopsy. The highest expression of CD34 was seen in NSIP biopsies, where this marker was highly expressed in interstitial areas and on mononuclear cells (FIG. 8D). Strong CD34 expression was also detected in interstitial areas in RBILD (FIG. 8F) and normal margin (FIG. 8H) SLBs. Further examination of the colocalisation of CD34 and CCR7 did not reveal areas in IIP or normal margin SLBs that showed dual expression of these proteins (not shown). Thus, CD34 was prominently expressed in less severe forms of IIP and in normal margin SLBs.

Figures 9A, 9B, 9C, 9D, 9E, 9F, 9G, 9H:
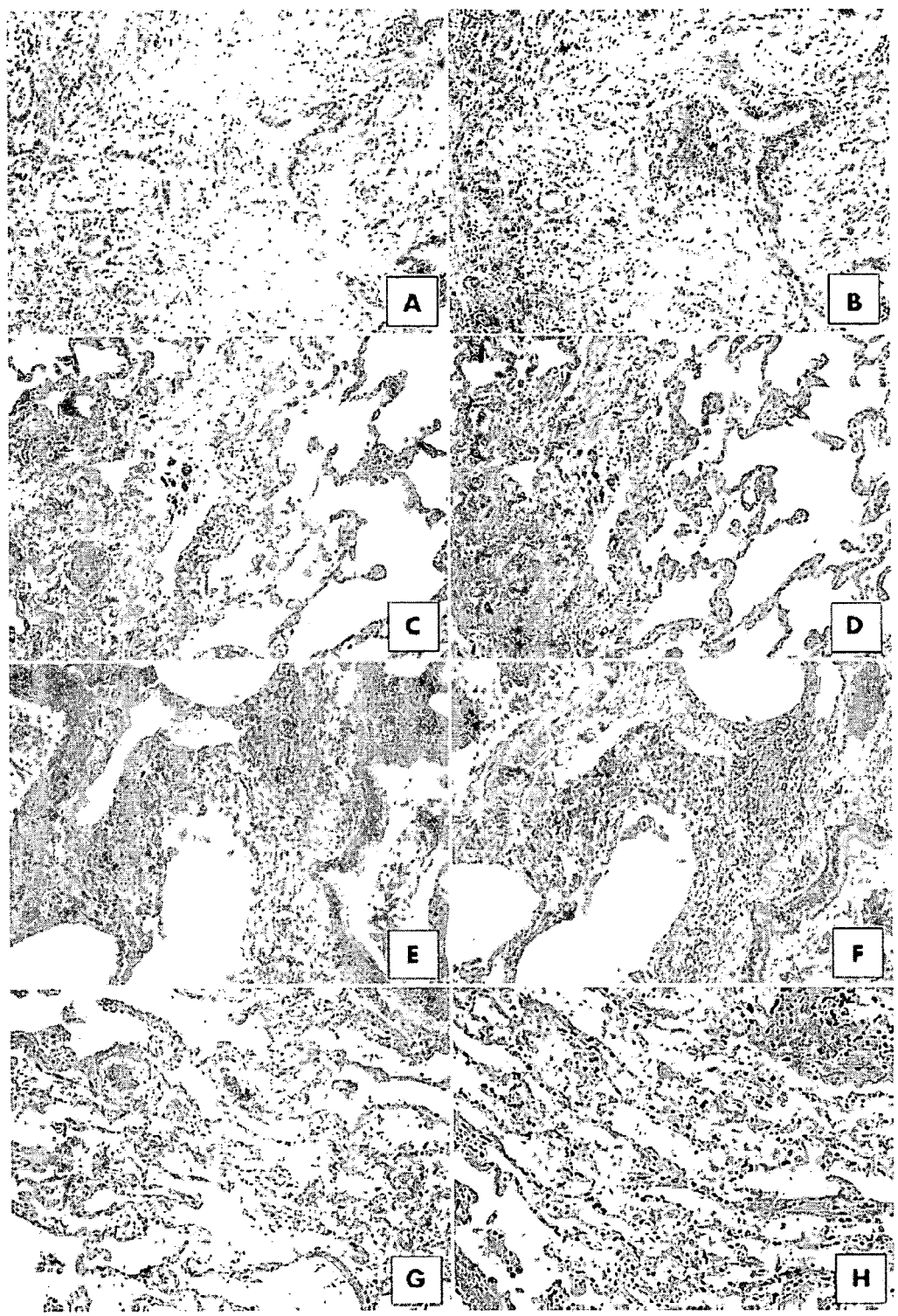
FIG. 9 Representative immunohistochemical analysis of collagen 1 in SLBs from (A, B) UIP, (C, D) NSIP, (E, F) RBILD, and (G, H) normal margin tumour patient groups. Panels (A), (C), (E), and (G) show control staining. Collagen immunoreactivity (red staining) was diffusely present throughout SLBs from (B) UIP, (D) NSIP, (F) RBILD, and (H) normal margin tumour patient groups. Original magnification, 6200. NSIP, non-specific interstitial pneumonia.
Figures 10A, 10B, 10C, 10D, 10E, 10F:
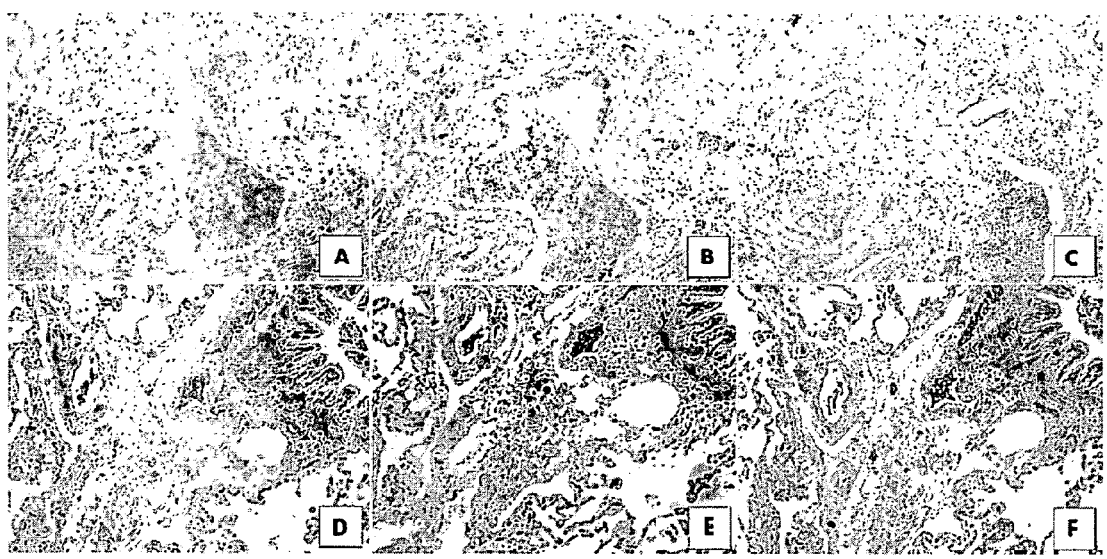

Collagen 1 is prominently expressed by fibrocytes and these cells generate collagen upon recruitment to sites of tissue injury. (Abe et al., J. Immunol., 166:7556-7562 (2001)) FIG. 9 summarises the immunohistochemical analysis of collagen 1 protein expression in IIP and normal margin SLBs. Collagen 1 was immunolocalised to interstitial areas in UIP (FIG. 9B), NSIP (FIG. 9D), RBILD (FIG. 9F), and normal margin (FIG. 9H) tumour patient biopsies. The highest expression of collagen 1 was seen in UIP SLBs, but high collagen 1 protein expression was also noted in normal margin SLBs. To determine whether collagen 1 and CCR7 colocalised in IIP biopsies, staining was also carried out on serial sections to determine the expression of both proteins (FIG. 10). Although collagen 1 was highly expressed all UIP SLBs (FIG. 10B), CCR7 was not expressed in areas with high collagen 1 expression (FIG. 10C). A similar pattern was seen in NSIP (not shown) and RBILD (FIG. 10E,F) SLBs, in which collagen 1 (FIG. 10E) did not appear to colocalise with CCR7 expression (FIG. 10F). Thus, CCR7 positive areas in IIP SLBs were not also positive for collagen 1.

Figures 11A, 11B, 11C, 11D, 11E, 11F, 11G, 11H, 11I:
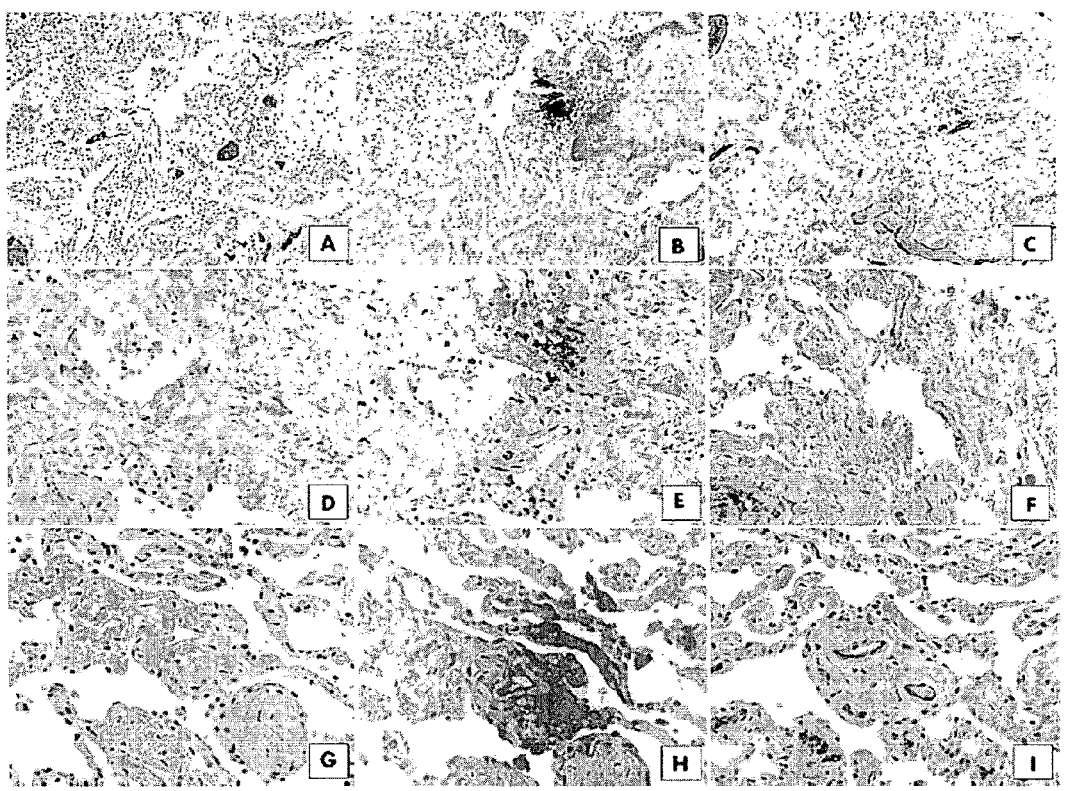

CCR7 positive areas in IIP SLBs lack aSMA expression FIG. 11 shows representative immunohistochemical staining for CCR7 and aSMA in histological lung sections from patients diagnosed with UIP (FIG. 11A-C), NSIP (FIG. 11D-F), and RBILD (FIG. 11G-I). In all three patient groups, foci of CCR7 (FIG. 11B,E,H) expression were seen in interstitial areas of the lung, as described above. However, areas that were positive for CCR7 did not overlap with those that were positive for aSMA in serial sections (FIG. 11C,F,I)).

The overall aim of the study was to examine the pattern of CCR7, CXCR4, CCL19, CCL21, and CXCL12 expression in lung biopsy samples from IIP and normal margin tumour patient groups. Quantitative transcript analysis and qualitative protein analysis revealed that CCR7, but not CXCR4, was dramatically increased in UIP relative to normal margin SLBs. UEP SLBs, and to a lesser extent NSIP SLBs, exhibited focal interstitial areas of intense CCR7 protein expression that were not concomitantly positive for CD34, collagen 1, or aSMA. Focal expression of CCR7 protein was seen in all UEP SLBs and smaller proportions of the NSIP and RBILD biopsies. In UIP SLBs, the focal interstitial expression of CCR7 protein appeared to include some CD45 positive cells, (Sallusto et al., Eur. J. Immunol., 28:2760-2769 (1998)) but most CCR7 positive cells lacked CD45 expression and there was no overlap between CCR7 and CD45 expression in biopsies from patients with NSIP and RBILD. Although it is possible that CCR7 expression in interstitial areas of UEP and NSIP biopsies may represent the recruitment of bone marrow derived fibrocytes, (Bucala et al., Mol. Med., 1:71-81 (1994)) there was no evidence that CCR7 positive areas in these biopsies were positive for fibrocyte markers, such as CD34 and collagen 1. In addition, these CCR7 positive cells lacked the myofibroblast marker aSMA. These data led to the speculation that focal CCR7 protein expression may indicate sites of idiopathic injury, and the inappropriate activation of resident fibroblasts, rather than the recruitment of fibrocytes expressing CCR7. Although their role in human disease has yet to be established, and no fibrocyte specific cell surface marker has been identified, several experimental fibrosis models point to a role for circulating cells of bone marrow origin in fibrotic events in the skin (Fathke et al., Stem Cells, 22:812-822 (2004)) and lung. (Hashimoto et al., J. Clin. Invest., 113:243-252 (2004); Phillips et al., J. Clin. Invest., 114:438-446 (2004); Epperly et al., Am. J. Respir. Cell Mol. Biol., 29:213-224 (2003); Schmidt et al., J. Immunol., 171: 380-389 (2003)) Most of these experimental studies use bone marrow chimera models constructed by the adoptive transfer of murine bone marrow transgenically expressing chimeric green fluorescent protein into irradiated mice. Green fluorescent protein positive bone marrow derived cells, which assumed macrophage-like (Epperly et al., Am. J. Respir. Cell Mol. Biol., 29:213-224 (2003)) and/or fibroblast-like (Hashimoto et al., J. Clin. Invest., 113:243-252 (2004); Phillips et al., J. Clin. Invest., 114:438-1446 (2004)) morphology, were shown to be major contributors to tissue fibrosis. In addition, these bone marrow derived cells were manganese superoxide dismutase sensitive, (Epperly et al., Am. J. Respir. Cell Mol. Biol., 29:213-224 (2003)) and expressed collagen 1, (Hashimoto et al., J. Clin. Invest., 113:243-252 (2004); Phillips et al., J. Clin. Invest., 114:438-446 (2004); Schmidt et al., J. Immunol., 171:380-389 (2003)) CD34, (Schmidt et al., J. Immunol., 171:380-389 (2003)) CD45, (Phillips et al., J. Clin. Invest., 114:438-446 (2004)) telomerase reverse transcriptase, (Hashimoto et al., J. Clin. Invest., 113:243-252 (2004)) CCR7, (Hashimoto et al., J. Clin. Invest., 113:243-252 (2004)) and CXCR4. (Hashimoto et al., J. Clin. Invest., 113:243-252 (2004); Phillips et al., J. Clin. Invest., 114:438-446 (2004)).

Nevertheless, controversy persists as to whether fibrocytes ultimately differentiate into myofibroblasts once they localize in the lung. It is presently assumed that fibrocytes recruited into the bronchial tissue after allergen exposure (Schmidt et al., J. Immunol., 171:380-389 (2003)) or into damaged cutaneous sites (Abe et al., J. Immunol., 166:7556-7562 (2001)) differentiate into myofibroblasts, whereas fibrocytes attracted to the lung during interstitial fibrosis caused by bleomycin do not express aSMA and cannot be induced to express this myofibroblast marker. (Hashimoto et al., J. Clin. Invest., 113:243-252 (2004)) Added controversy regarding these cells is the observation that not all bone marrow derived cells appear to be deleterious during tissue repair. Accordingly, Ortiz and colleagues (Ortiz et al., Proc. Natl. Acad. Sci. USA, 100:8407-8411 (2003)) have shown that murine mesenchymal stem cells migrate to the injured lung, assume an epithelium-like phenotype, and reduce inflammation and collagen deposition in bleomycin challenged mice. Clearly, further investigation is required to delineate the role of bone marrow derived cells in the clinical fibrotic response.

Impetus to examine CCR7 and CXCR4 in SLBs from patients with IIP stemmed from previous studies showing that CCL21, a ligand of the CCR7 chemokine receptor, was a potent stimulus for fibrocyte chemotaxis in vitro and in vivo, (Abe et al., J. Immunol., 166:7556-7562 (2001)) and that CXCR4 positive bone marrow derived cells contribute to experimentally induced fibrosis. (Hashimoto et al., J. Clin. Invest., 113:243-252 (2004); Phillips et al., J. Clin. Invest., 114:438-446 (2004)) It is postulated that fibrocytes can rapidly enter sites of tissue injury through CCR7, CXCR4, or possibly other chemokine receptor dependent chemotactic events and contribute to the pathogenesis of pulmonary fibrosis. (Phillips et al., J. Clin. Invest., 114:438-446 (2004)) In the present study, focal areas of CCR7 expression were examined for the presence of putative fibrocyte markers, including CD45, CD34, and collagen 1. (Abe et al., J. Immunol., 166: 7556-7562 (2001); Hartlapp et al., FASEB J., 15:2215-2224 (2001)) CD45 was the only marker that was present in the focal areas of CCR7 expression, and colocalisation of CD45 and CCR7 was only seen in mononuclear cells present within UIP, and not other IIP biopsies. In addition, all of these markers were detected in normal margin SLBs although the immunohistochemical techniques failed to detect CCR7 in these biopsies. Although the findings do not rule out the possibility that the CCR7 positive cells seen in patient biopsies are fibrocytes, it is possible that the expression of these markers is quickly downregulated upon the migration of fibrocytes from the circulation into the lung.

The observation that CXCR4 was not present in focal areas of IIP SLBs also does not rule out the importance of this chemokine receptor in the recruitment of fibrocytes and/or collagen producing bone marrow derived cells to the lung. A diffuse pattern of CXCR4 expression was seen in all SLBs analyzed and most of the cells expressing this chemokine receptor appeared to be mononuclear cells.

Given the abnormal synthetic and proliferative characteristics of UIP fibroblasts (highlighted by histologically distinct fibroblastic foci (King et al., Am. J. Respir. Crit. Care Med., 164:1025-1032 (2001)), the inventors hypothesised that these cells may also be inappropriately responding to chemokine ligands that usually regulate the function of immune cells. Tissue resident fibroblasts comprise a major component of the lung architecture, and many investigators have proposed that the inappropriate activation of these cells underlies the pathological fibrotic response seen in UEP and possibly other forms of IIP. (Suganuma et al., Thorax, 50:984-989 (1995); Hogaboam et al., Proc. Assoc. Am. Physicians, 110:313-320 (1998); Ramos et al., Am. J. Respir. Cell Mol. Biol., 24:591-598 (2001); Selman et al., Respir. Res., 3:3 (2002)) The factors that contribute to this inappropriate activation have yet to be elucidated, but data from several laboratories indicate that chemokines may play a role in this process. (van den Blink et al., Arch. Immunol. Ther. Exp. (Warsz), 48:539-545 (2000); Selman, Am. J. Respir. Crit. Care Med., 168:730-731 (2003)) For example, it is now widely recognised that UIP fibroblasts from fibrotic lungs migrate faster than those from control lungs, (Suganuma et al., Thorax, 50:984-989 (1995)) and there is some suggestion from mouse studies that chemokines have a major role in this respect. (Moore et al., J. Immunol., 167:4368-4377 (2001)) Further impetus to examine the possibility that CCR7 and CXCR4 may play a role in the aberrant migratory activity of cells in IIP was derived from recent discoveries in the field of cancer biology, which have documented the expression of a unique repertoire of chemokine receptors on breast cancer cells that explain, in part, the metastatic properties of breast tumours. (Muller et al., Nature, 410:50-56 (2001))

Thus, the present study demonstrated the focal interstitial expression of CCR7 in IIP. The identity of the cells expressing this receptor has yet to be fully elucidated, but areas containing focal CCR7 expression were not positive for CD34 and collagen 1. CCR7 expressing cells in the interstitial areas of IIP biopsies also did not express aSMA, thereby ruling out the possibility that these cells were myofibroblasts.

In Example 3 presented below, data are provided that show that the synthetic and proliferative properties of IIP fibroblasts, but not normal margin fibroblasts, are differentially influenced by exogenous CCL19 and CCL21. These studies are of potential therapeutic importance, given that it may be possible to inhibit the migration of fibrocytes and/or the activation of resident pulmonary fibroblasts in response to CCR7 specific chemokines, thereby preventing the excessive production of extracellular matrix in favour of appropriate lung repair.

Example 3

Targeting CCL19 or CCL21 for Treatment of Chronic Fibrosing Disorders

This Example details the novel potential in targeting CCL19 and/or CCL21 during chronic fibrosis in the lung. Chronic pulmonary fibrosis of known and idiopathic origin presents extraordinary clinical challenges for which treatment options show limited effectiveness or toxicity (Flaherty et al., Am. J. Med., 110:278-282 (2001); Hampton et al., Am. J. Respir. Crit. Care Med., 149:A878 (1994)), and the median survival rate following diagnosis has changed little (Ryu et al., Mayo Clin. Proc., 73:1085-1101 (1998); Lasky et al., Environ. Health Perspect., 108 Suppl 4:751-762 (2000)). Known profibrotic stimuli include radiation, inhaled mineral and organic particles, gaseous oxidants, pharmaceutics and infectious organisms, whereas debate persists regarding the identity of etiological factors that initiate the clinicopathologic entities of idiopathic interstitial pneumonias (IIP). IIP are a diverse group of disorders involving the distal pulmonary parenchyma, which share numerous features, but are felt to be sufficiently different to justify designation as separate disorders (Travis et al., Am. J. Surg. Path., 24:19-33 (2000)). Their pathogenesis remains unclear but is thought to center around an injury (or multiple injuries) to the lung followed by attempts to heal this injury. Fibroblastic foci, small aggregates of actively proliferating fibroblasts, are believed to represent the organization of prior foci of injury and indicate that fibrosis is active and ongoing. At present, the hypothesis is that the responsiveness of human fibroblasts to CCL19 and CCL21 (due their upregulation of CCR7) leads to the inappropriate activation of these cells thereby leading to the exuberant fibrotic responses observed in IIP.

Interestingly, the cytokine environment in the lung of fibrotic patients may favor the aberrant response to CCL19 and CCL21 since other investigators have documented increased protein levels of TNF-α (Ziegenhagen et al., J. Investig. Med., 46:223-231 (1998); Kapanci et al., Am. J. Respir. Crit. Care Med., 152:2163-2169 (1995)) and decreased IL-10 (Martinez et al., Am. J. Physiol., 273:L676-683 (1997)), both cytokines that modulate the receptor that these ligand bind to. Human fibroblasts from patients with severe forms of pulmonary fibrosis clearly respond to CCL19 and CCL21, thereby making these ligands attractive targets in the treatment of fibrosing diseases in the lung and possibly in other tissues.

The inventors have addressed whether it is possible to induce pulmonary fibrosis after the intravenous introduction of human fibroblasts lines into immunodeficient mice. With this model, the inventors examined whether the intravenously injected human fibroblasts can initiate a fibrotic response in an in vivo system that lacks the ability to mount an inflammatory response.

The data also show that this model is amenable to testing the efficacy of targeting either CCR7 or its ligands during the initiation of or after the development of pulmonary fibrosis. It appears that the C.B-17-bg SCID mouse is ideal for adoptive transfer studies with human fibroblasts because C.B-17-bg mice lack T and B cells (similar to the C.B-17 and ICR SCIDs) and also carry the beige mutation, which leads to the impairment of cytotoxic T cell, macrophage and NK cell functions.

The intravenous. introduction of fibroblasts grown from fibrotic human biopsies into C.B-17-bg resulted in histologically evident and prominent pulmonary fibrosis based on Masson trichrome staining.

In other studies, SCID mouse lung tissues were examined at day 35 after fibroblast injection using the hydroxyproline assay and found that the levels of hydroxyproline are markedly elevated in lung samples from the mice that received fibroblasts grown from fibrotic human biopsies compared with mice that received normal human fibroblasts. Thus, the data from the humanized SCID model suggests that it is possible to 'transfer' a fibrotic disease with human IIP fibroblasts. This humanized SCID model should allow examination of the factor(s) that contribute to the maintenance of pulmonary fibrogenesis.

In human studies, it was shown that the transcript (FIG. 12) and protein (FIG. 13) expression for CCL21 is markedly increased in surgical lung biopsies from patients with various forms of chronic pulmonary fibrosis compare with those who have other types of non-fibrosing diseases. Data showed that pulmonary fibroblasts obtained from patients with evidence of pulmonary fibrosis but not fibroblasts from patients without evidence of abnormal fibrosis, exhibit migratory (FIG. 14) and proliferative responses (FIG. 15) in response to exogenous CCL19 or CCL21. The observation that CCL19 and CCL21 drive the migration of pulmonary fibroblasts (FIG. 14) is exciting because this response may contribute to the development of foci of proliferating fibroblasts, a major histopathological feature in UIP.

Finally, the therapeutic efficacy of targeting CCL21 during the initiation and maintenance of pulmonary fibrosis was demonstrated using the murine SCID model of fibrosis that is characterized by interstitial fibrosis and fibroblastic foci (FIG. 16).

Example 4

Targeting CCL21 or CCR7 is Effective to Abrogate Pulmonary Fibrosis Induced by Adoptive Transfer of Human Pulmonary Fibroblasts in Immunodeficient Mice As discussed above, CC chemokine receptor 7 (CCR7) is expressed in IIP biopsies and primary fibroblast lines. In the present example, there are provided details of a study of the in vivo role of CCR7 in a model of pulmonary fibrosis. Briefly, $1.0 \times 10^6$ primary fibroblasts grown from idiopathic pulmonary fibrosis/usual interstitial pneumonia (EPF/UIP), non-specific interstitial pneumonia (NSIP), or histologically normal biopsies were injected intravenously into C.B.-17SCID/beige (bg) mice. At days 35 and 63 after IPF/UIP fibroblast injection, patchy interstitial fibrosis, and increased hydroxyproline were present in the lungs of immunodeficient mice. Adoptively transferred NSIP fibroblasts caused a more diffuse interstitial fibrosis and increased hydroxyproline levels at both times but injected normal human fibroblasts did not induce interstitial remodeling changes in C.B-17SCID/bg mice. Systemic therapeutic immunoneutralization of either human CCR7 or CCL21, its ligand, significantly attenuated the pulmonary fibrosis in groups of C.B-17SCID/bg mice that received either type of IIP fibroblasts. Thus, the present study demonstrates that pulmonary fibrosis is initiated by the intravenous introduction of primary human fibroblast lines into immunodeficient mice, and this fibrotic response is dependent on the interaction between CCL21 and CCR7.

Mouse models of pulmonary fibrosis have provided experimental paradigms with which to address abnormal tissue remodeling and scarring in the respiratory system (Gharee-Kermani et al., Meths. Mol. Med., 2005, 117:251-259). A number of approaches have been employed to induce pulmonary fibrosis and these include transgenic and gene transfer, radiation, inorganic irritants such as silica, and drugs promoting oxidant-induced inflammatory injury such as bleomycin (Chua et al., Am. J. Resp. Cell Mol. Biol., 2005, 33:9-13). Of these models, the bleomycin model remains the most widely employed due to its reproducibility and pathologic similarity to human pulmonary fibrosis ((Chua et al., Am. J. Resp. Cell Mol. Biol., 2005, 33:9-13). Accordingly, the bleomycin model has been used to assess a number of targets of interest in IPF/UIP (Kaminski et al., Proc. Natl Acad. Sci. USA 200, 97:1778-1783; Pardo et al., PLoS Med 2005, 2e251).

Unfortunately, no animal model exists that fully recapitulates the clinicopathologic features of IPF/UIP, and debate still exists pertaining to the relative importance of ongoing inflammatory injury (the primary mode for inducing experimental fibrosis) to end stage UIP (Gauldie, Am. J. Resp. Crit. Care Med. 2002, 165:1205-1206; Stierter Am. J. Resp. Crit. Care Med. 2002, 165:1207-1208).

The present example circumvents the problem in the art by using an alternative strategy for inducing experimental pulmonary fibrosis. Genetically immunodeficient mice, due to severe combined immunodeficiency gene mutation (scid) or recombinase activating gene 1 (rag-1) knockout, have been extensively used as in vivo hosts of adoptively transferred normal or diseased human cells. In the present example it is shown that the adoptive intravenous (i.v.) transfer of either IPF/UIP or nonspecific interstitial pneumonia (NSIP; another less severe form of IIP) but not normal fibroblasts into C.B-17 mice with the scid-beige (C.B-17SCID/bg) mutation initiated and maintained pulmonary fibrosis. Histological and biochemical evidence of fibrosis was first evident in both IIP fibroblast groups of C.B-17SCID/bg mice at day 35 and was prominent at day 63 after fibroblast injection. Cytokines and chemokines both appear to have major roles in the pathogenesis of IIP, and ELISA analysis of whole lung samples from C.B-17SCID/bg mice that received either IPF/UIP or NSIP fibroblasts revealed significant elevations in murine IL-13, CCL6 and CCL21 at day 63 compared with whole lung levels measured at the earlier time point or in lung tissue from mice that did not receive fibroblasts.

IL-13 and CCL6 are mediators of pulmonary fibrosis but the role of CCL21 in pulmonary remodeling events was unknown. Impetus to examine the role of CCL21 and CCR7 in the pulmonary remodeling events precipitated by human IIP fibroblasts stemmed from the above-reported findings that CCR7 expression is increased in IIP biopsies, and the migratory, synthetic, and proliferative properties of IIP fibroblasts are significantly enhanced by CCL21 (EMP and CMH, unpublished findings). In separate immunoneutralization studies, the targeting of either human CCL21 or CCR7 (the receptor for CCL21) from days 35 to 63 after IIP fibroblast injection into C.B-17SCID/bg mice significantly reduced all parameters of pulmonary fibrosis compared with groups of C.B-17SCID/bg mice receiving IIP fibroblasts and IgG. Together, these data highlight the creation of new murine model of pulmonary fibrosis initiated and maintained by the i.v. introduction of IIP fibroblasts into C.B-17SCID/bg mice, and demonstrate a novel role for CCL21 and CCR7 in the maintenance of fibrosis in this model.

Mice:

Female, ICR-scid (ICRSCID), C.B-17-scid (C.B-17SCID), and C.B-17-scid-beige (C.B-17SCID/bg) mice (6-8 wks old) were purchased from Taconic Farms (Germantown, N.Y.) and all SCID mice were housed in a gnotobiotic barrier facility at the University of Michigan Medial School. The first two groups of mice have the severe combined immunodeficiency (scid) mutation leading to a lack of both T and B lymphocytes due to a V(D)J recombination defect whereas C.B-17SCID/bg mice have two mutations: the first is the scid mutation, and the second is a beige mutation leading to a major defect in cytotoxic T cell and macrophage function and a selective impairment in NK cell function. All mice had access to autoclaved water and pelleted mouse diet ad libitum. All procedures described below were performed in a sterile, laminar environment and were approved by an animal care and use committee at the University of Michigan Medical School.

Human Fibroblast Cell Culture:

A mixed cell population was obtained from mechanically dissociated IPF/UIP and NSIP surgical lung biopsies, and pure human fibroblast cultures were derived as previously described in detail elsewhere (Jakubzick et al., Am. J. Pathol., 2004 164:1989-2001). Normal lung fibroblasts were purified in the same manner from cell suspensions of normal margins associated with resected lung tumor tissue. In the present study, a total of 10 IPF/UIP, 6 NSIP, and 4 normal fibroblast lines were used after the fourth passage in the initial, model characterization, and therapeutic intervention studies described herein.

Intravenous Introduction of Human Pulmonaryfibroblasts into SCID Mice:

Single cell preparations of IPF/UIP, NSIP, and normal fibroblasts were obtained following trypsinization of 150 cm2 tissue culture flasks and labeled with PKH26 dye according to the manufacturer's (Sigma Co., St. Louis, Mo.) directions. Each labeled fibroblast line was diluted to $1 \times 10^6$ cells/ml of PBS, and 1 ml of this suspension was injected via a tail vain into groups of five SCID mice. Other groups of five SCID mice were injected intravenously with PKH26 and PBS labeling solution alone (i.e. control group). Mice were euthanized by anesthesia overdose at days 7, 21, 35, 49, and 63 after the i.v. human pulmonary fibroblast transfer. Whole lung tissue was dissected at these times for molecular, histological, biochemical, and/or proteomic analysis (see below).

Assessing the Role of CCL21 and CCR7 in C.B-17SCID/bg Mice after the Adoptive Transfer of Human Pulmonary Fibroblasts:

To address the role of CCL21 and CCR7, its receptor, in the pulmonary remodeling response after the i.v. adoptive transfer of human fibroblasts, groups of C.B-17SCID/bg mice received IPF/UIP (n=35 mice), NSIP (n=20 mice), normal fibroblasts (n=15 mice), or vehicle (i.e. PBS) alone (n=15 mice). Thirty-five days later all groups of five C.B-17SCID/bg mice received one of mouse IgG, mouse anti-human CCL21 monoclonal antibody, or mouse anti-human CCR7 monoclonal antibody (all at 10 µg/ml; R&D Systems, Minneapolis, Minn.) every other day from days 35 through to day 63. At day 63, all mice were euthanized by anesthesia overdose and whole lung tissue was dissected for molecular, histological, biochemical, and proteomic analysis (see below).

Molecular Analysis:

Total RNA was isolated and cDNA generated from whole lung samples as previously described in detail (Jakubzick et al., J. Immunol. 2003, 171:2684-2693). Changes in gene profiles for human and murine chemokine and chemokine receptors were analyzed in pooled samples (n=5) using non-radioactive GEArray gene array membranes according to the manufacturer's instructions (SuperArray, Inc., Bethesda, Md.) and signal intensities were determined as previously described in detail (Jakubzick et al., Am. J. Pathol., 162:1475-1486 (2003). Individual whole lung cDNA samples (n≥5) were analyzed for human CCR7, Collagen I, cathepsin E, matrix metalloproteinase (MMP)-2, MMP-9, MMP-19, fibronectin, tissue inhibitors of metalloproteinases (TIMP)-1 and GAPDH expression by realtime quantitative RT-PCR procedure using an 7500 Real Time PCR System (Applied Biosystems, Foster City, Calif.) as previously described (Jakubzick et al., J. Immunol. 2003, 171:2684-2693).

Histological Analysis:

After anesthesia-induced euthanasia, the right lobes from each mouse were dissected, fully inflated with 10% formalin solution, and placed in fresh formalin for 24 hours. Standard histological techniques were used to paraffin-embed each lobe and 5-µm sections were stained with H&E and Mason trichrome for histological analysis. Additional unstained whole lung tissue sections were analyzed via fluorescent microscopy.

Biochemical Analysis:

Whole left lung samples were homogenized in 1×PBS and pelleted by centrifugation. The cell-free supernatants were removed for ELISA analysis and the pellets were vacuum-dried and resuspended in 0.5 M Glacial acetic acid. The tissue was then processed for hydroxyproline concentration as previously described (Zhang et al., J. Immunol. 1994, 153:4733-4741).

Proteomics:

Murine IL-13, CCL6, CCL21, IFN-γ, IL-12, IL-4, CCL2, CCL7, CCL17, CCL3, CXCL13, TNF-α, CXCL10, CXCL9, and CXCL2 proteins were analyzed in 50 µl cell-free supernatants from homogenized whole lung samples using a standardized sandwich enzyme linked immunosorbent assay (ELISA) technique (R&D Systems, Minneapolis, Minn.) as previously described in detail (Jakubzick et al., J. Immunol. 2003, 171:2684-2693).

Statistical Analysis:

All results are expressed as mean±SEM. One-way ANOVA analysis and Tukey-Kramer or Dunnett's multiple comparisons tests were used to detect statistical differences between UIP, NSIP, normal and control SCID mouse groups. Significance was set at $p<0.05$.

The Adoptive Intravenous Transfer of Either IPF/UIP or NSIP, but not Normal, Pulmonary Fibroblasts Promoted Lung Histopathology and Remodeling in C.B-17SCID/bg Mice.

Initial studies were undertaken to assess the impact of adoptively transferred normal and IIP fibroblasts on the lung architecture in various strains of SCID mice including ICR-SCID, C.B-17SCID, and C.B-17SCID/bg (n=5 per time point). These initial studies were undertaken using 3 IPF/UIP and 2 normal human fibroblast lines. All human fibroblast lines were labeled with PKH26 prior to injection into the SCID mouse groups thereby allowing for the detection of labeled cells in histological sections. At days 7 and 21 after injection, collections of human fibroblasts were detected in pulmonary blood vessels in each SCID group. However, the intensity of this marker diminishes after 21 days (information from the provided Sigma data sheet), and, hence, we failed to detect PKH26 fluorescence in histological sections from each at day 35 after fibroblast injection (not shown). Other organs (i.e. liver, spleen, and kidney) presumably contained human pulmonary fibroblasts, but we observed no evidence of gross macroscopic alterations to these organs. Because IIP is a lung-specific disease, which does not exhibit fibrogenesis in any other organ, a detailed histological analysis of other organs was not undertaken in the present study.

Examination of whole lung sections in groups of SCID mice at later time points revealed that marked lung remodeling was only present in C.B-17SCID/bg mice. Specifically, no fibroproliferation was observed at day 49 after the introduction of IPF/UIP fibroblasts into ICRSCID mice (n=5 mice; not shown). Likewise, the i.v. adoptive transfer of IPF/UIP fibroblasts into C.B-17SCID mice failed to elicit histologically evident pulmonary remodeling at days 7 (n=5 mice), 21 (n=10 mice), 35 (n=5 mice), or 49 (n=5 mice) after the i.v. injection of IPF/UIP fibroblasts.

Given the presence of marked pulmonary histopathology in the C.B-17SCID/bg group, all subsequent studies described below involved the adoptive transfer of normal and IIP fibroblasts into C.B-17SCID/bg mice. In the model characterization study, four IPF/UIP, four NSIP, and one normal fibroblast line(s) were adoptively transferred into separate groups of C.B17-SCID/bg mice and pulmonary histopathological, genomic and proteomic alterations were analyzed at days 35 and 63 after fibroblast transfer.

Little or no pulmonary histopathology was observed in C.B-17SCID/bg mice that received normal pulmonary fibroblasts. However, C.B-17SCID/bg mice exhibited significant pulmonary histopathology, which was evident at day 35 after the i.v. injection of either NSIP or IPF/UIP fibroblast lines. The pulmonary histopathology in C.B-17SCID/bg mice following NSIP or IPF/UIP pulmonary fibroblasts was characterized by disruption of the alveolar space, apparent fibroproliferation and the presence of eosinophilic granulocytes. Mason trichrome staining of histological tissue sections from the lungs of C.B-17SCID/bg mice at day 35 after the adoptive transfer of normal, NSIP, or IPF/UIP human pulmonary fibroblasts revealed the presence of extracellular matrix (stained light blue) in remodeled areas in C.B-17SCID/bg groups that received the IIP but not normal fibroblasts.

Later analysis of histological sections from C.B-17SCID/bg groups revealed major differences in the extent and appearance of the pulmonary remodeling precipitated by the introduction of IPF/UIP or NSIP fibroblasts. The lungs of C.B-17SCID/bg mice that received IPF/UIP fibroblasts 63 days previously exhibited a heterogeneous appearance with areas of relatively normal appearing lung tissue adjacent to areas of severe interstitial disruption and remodeling. Also, foci of human fibroblasts were apparent in the lungs of C.B-17SCID/bg mice that received IPF/UIP fibroblasts but these foci were detected in blood vessels and not in interstitial areas as in clinical UIP (Am. J. Resp. Crit. Care Med 2002, 165: 277-304). The histological pattern in whole lung tissue sections from C.B-17SCID/bg mice that received NSIP fibroblasts 63 days previously was characterized by interstitial thickening and overtly fibrotic areas, and the remodeling in these mice appeared to involve most of the lung. Together, these data showed that the introduction of human IIP fibroblasts into C.B-17SCID/bg mice caused fibrotic lesions in these mice.

Hydroxyproline Levels were Significantly Altered in a Temporally Dependent Manner after the Introduction of IIP Fibroblasts into C.B-17SCID/bg Mice:

Hydroxyproline is a commonly used marker of de novo collagen synthesis in experimental models involving pulmonary remodeling (Jakubzick et al., Am. J. Pathol., 2004, 165: 1222-1221). In the present study, hydroxyproline levels were measured in whole lung samples from C.B-17SCID/bg mice that had received no fibroblasts or normal, NSIP, or IPF/UIP human pulmonary fibroblasts either 35 or 63 days previously. Hydroxyproline levels were unchanged at these time points after the introduction of normal fibroblasts. The levels of hydroxyproline in these C.B-17SCID/bg groups were 4.7±0.3 and 5.6±0.5 µg/mg of protein at days 35 and 63, respectively, and these hydroxyproline levels were similar to those detected in C.B-17SCID/bg mouse groups that did not receive human fibroblasts (4.5±1.3 µg/mg of protein). However, the lungs of mice contained greater amounts of hydroxyproline at day 35 after intravenously transferred NSIP (11.4±3.7 µg/mg of protein) or IPF/UIP (8.2±2 µg/mg of protein) fibroblasts compared with the normal fibroblast group. Also, hydroxyproline levels were further increased 3- and 2.5-fold in the NSIP (31±11 µg/mg of protein) and IPF/UIP (22±4 µg/mg of protein) fibroblast groups, respectively, at day 63 after i.v. adoptive transfer. At the day 63 time point, the increase in hydroxyproline levels in the C.B-17SCID/bg groups that received either NSIP or IPF/UIP human fibroblasts reached statistical significance compared with the C.B-17SCID/bg group that received normal fibroblasts. Thus, the intravenous injection of human IIP fibroblasts enhanced hydroxyproline levels at day 35, and most demonstrably, at day 63 after adoptive transfer.

Whole Lung Cytokine Analysis Showed that Murine IL-13, CCL6, and CCL21 Were Significantly Elevated in the Lungs of C.B-17SCID/bg Mice that Received IIP Fibroblasts:

Whole lung ELISA analysis of several cytokines, CC ligand, and CXC ligand chemokines at days 35 and 63 after the i.v. adoptive transfer of human normal or IIP fibroblasts revealed a number of statistically significant changes in murine IL-13, CCL6, and CCL21. Although the whole lung levels of IL-13 in the C.B-17SCID/bg group that received normal fibroblasts were below the level of ELISA detection, whole lung IL-13 levels were significantly greater in the C.B-17SCID/bg group that received either NSIP or IPF/UIP fibroblasts compared with the C.B-17SCID/bg group that received normal fibroblasts 35 and/or 63 days previously. Also, significantly greater IL-13 was detected in the lungs of C.B-17SCID/bg mice that received IPF/UIP fibroblasts at day 63 versus day 35 after fibroblasts adoptive transfer. At days 63 after fibroblast injection, whole lung CCL6 levels were significantly greater in the C.B-17SCID/bg groups that received either IPF/UIP or NSIP fibroblasts compared with the C.B-17SCID/bg group that received normal fibroblasts. Significantly greater CCL6 was detected in the lungs of C.B-17SCID/bg mice that received IPF/UIP or NSIP fibroblasts at day 63 versus day 35 after fibroblasts adoptive transfer. The only other murine CC ligand that was altered by the introduction of human fibroblasts into C.B-17SCID/bg mice was CCL21. This chemokine was significantly greater in the NSIP and IPF/UIP fibroblast C.B-17SCID/bg groups at day 63 compared with the normal fibroblast C.B-17SCID/bg groups at day 63. In addition, whole lung murine CCL21 levels were significantly elevated in IPF/UIP fibroblast groups at day 63 after fibroblast transfer compared with the NSIP fibroblast group at the same time. Finally, significantly higher levels of CCL21 were present in whole lung samples from the IIP fibroblasts C.B-17SCID/bg group at day 63 after adoptive transfer compared with the IIP fibroblasts C.B-17SCID/bg groups at day 35 after adoptive transfer. Thus, taken together these data suggested that the presence of IIP fibroblasts, but not normal fibroblasts, in C.B-17SCID/bg mice significantly altered the whole lung levels of murine cytokines and chemokines with established (i.e. IL-13 and CCL6) and putative (i.e. CCL21) profibrotic roles in the lung.

Human CCR7 and CCL21 Gene Transcripts were Present in the Lungs of C.B-17SCID/Bg Mice that Received Human Pulmonary Fibroblasts 35 Days Previously:

The changes in whole lung levels of murine CCL21 in C.B-17SCID/bg mice that received either NSIP or IPF/UIP fibroblasts were intriguing in light of previous studies demonstrating the important remodeling role of this CC ligand in the kidney (Banas et al., J. Immunol., 2002 168:4301-4307) and liver (Bonaccgi et al. Gastroenterology, 2003, 125:1060-1076). This prompted further analysis of this CC ligand and its receptor, CCR7, during the pulmonary remodeling responses elicited by human IIP fibroblasts. Human transcripts for CCR7 and CCL21 were detected by SuperArray gene analysis, and among the three C.B-17SCID/bg groups the greatest transcript expression for CCR7 and CCL21 was present in lung samples from the IPF/UIP fibroblast group. Further, the presence of CCR7 was confirmed by TAQMAN analysis, and again the IPF/UIP group exhibited the highest CCR7 transcript expression among the C.B-17SCID/bg groups. SuperArray and TAQMAN analysis of murine CCR7 and CCL21 also confirmed the presence of these transcript products in all three C.B-17SCID/bg groups that received human fibroblasts, and the highest levels of both transcripts were present in the C.B-17SCID/bg groups that received IPF/UIP fibroblasts. Thus, the i.v. adoptive transfer of normal and IIP fibroblasts resulted in the presence of human gene transcripts for CCR7 and CCL21.

Quantitative TAQMAN PCR Analysis of Murine Extracellular Matrixassociated Genes Following the Adoptive Transfer of Human Fibroblasts into C.B-17SCID/Bg Mice:

Lung alterations in murine extracellular matrix associated genes were analyzed using quantitative PCR analysis. The expression of collagen 1, cathepsin E, MMP-19, and TIMP-1 was present in C.B-17SCID/bg mice that received normal, NSIP, and IPF/UIP human fibroblasts 63 days previously. Most importantly, when transcript levels for these genes in fibroblast-challenged mice were compared to transcript levels in control C.B-17SCID/bg mice, the increases in collagen 1 and cathepsin transcript expression in C.B-17SCID/bg mice that received either type of IIP fibroblast and MMP-19 and TIMP-1 transcript expression in mice that received IPF/UIP fibroblasts reached statistical significance when compared to the transcript increases for these genes in C.B-17SCID/bg mice that received normal human fibroblasts. Other extracellular matrix genes were analyzed by TAQMAN and their presence was confirmed: MMP-2, MMP-9, and fibronectin. No significant differences in levels of these transcripts were observed among the groups of C.B-17SCID/bg mice, but the greatest increase in MMP-2 and fibronectin was observed in the IPF/UIP C.B-17SCID/bg group while the smallest increase in MMP-9 was observed in this same C.B-17SCID/bg group. Thus, these data showed that transcript levels for murine extracellular matrix associated genes were altered by the presence of human fibroblasts in C.B-17SCID/bg mice.

Immunoneutralization of Human CCR7 or Human CCL21 Abrogated Pulmonary Remodeling in C.B-17SCID/Bg Mice that Received Human IIP Fibroblasts:

In the next series of experiments, the roles of human CCR7 and CCL21 were assessed in C.B-17SCID/bg mice that received human normal (n=1 line) or IIP fibroblasts (n=3 IPF/UIP and n=2 NSIP lines). Although attempts to measure human CCL21 in whole lung samples were unsuccessful presumably due the presence of this CC ligand at levels below the level of ELISA detection, previous studies have shown that both mouse and human CCL21 can promote cellular calcium flux via human CCR7 (Jenh et al., J. Immunol., 1999 162:3765-3769). In addition, the immunoneutralization of mouse CCL21 using a polyclonal antibody has been shown to abrogate the migration of human dendritic cells and the priming of human T cells in a humanized model of house dust mite-induced allergic airway disease (Hammad et al. J. Immunol. 2002, 169:1524-1534). Given the reported cross-reactivity of mouse and human CCL21, a therapeutic protocol was implemented in which either human CCL21 or human CCR7 were targeted by monoclonal antibody administration from days 35 to 63 after the adoptive transfer of fibroblasts. A histological survey of whole lung tissues at day 63 in the three C.B-17SCID/bg groups with the three treatment modalities tested showed that in the normal fibroblast C.B-17SCID/bg group, no evidence of interstitial pulmonary remodeling was evident in any of the treatment groups (IgG treatment; anti-CCL21 antibody treatment; anti-CCR7 antibody treatment). However, the vascular accumulation of normal fibroblasts was histologically apparent in these C.B-17SCID/bg groups. None of the treatments altered this feature in C.B-17SCID/bg mice that received normal fibroblasts. Interstitial remodeling was apparent in the NSIP fibroblast C.B-17SCID/bg group that received IgG but this remodeling response was abrogated by either anti-CCL21 antibody or anti-CCR7 antibody administration from days 35 to 63 after adoptive transfer. Likewise, the interstitial remodeling apparent in the IgG C.B-17SCID/bg group that received IPF/UIP fibroblasts was absent in groups of C.B-17SCID/bg mice that received anti-CCL21 antibody or anti-CCR7 antibody administration from days 35 to 63 after adoptive transfer IPF/UIP fibroblasts. Thus, therapeutic targeting of either CCL21 or CCR7 abrogated histological evidence of interstitial remodeling in C.B-17SCID/bg mice that received IIP fibroblasts.

Quantitative TAQMAN PCR Analysis of Murine Extracellular Matrix-Associated Genes Following the Therapeutic Targeting of Either Human CCL21 or CCR7 in C.B-17SCID/bg Mice that Received Human Normal and IIP Fibroblasts:

Quantitative TAQMAN analysis of the antibody treatment groups also confirmed that the anti-CCL21 and anti-CCR7 treatments also significantly altered the transcript levels of MMP-2 and MMP-19. Transcript levels for these MMPs in antibody-treated, control C.B-17SCID/bg mice were compared to the levels of these transcripts in antibody-treated, fibroblast challenged C.B-17SCID/bg mice. Anti-CCL21 antibody treatment significantly reduced the fold increase in MMP-2 transcript levels in C.B-17SCID/bg groups that received normal fibroblasts upon comparison to the fold increase in the transcript levels in C.B-17SCID/bg groups that received IgG. The anti-CCR7 antibody treatment significantly reduced the fold increase in MMP-2 transcript levels compared with the appropriate IgG group. Quantitative TAQMAN analysis of MMP-19 revealed that anti-CCR7 significantly increased the fold change in the C.B-17SCID/bg group that received normal fibroblasts, whereas both antibody treatments significantly increased the fold change in this transcript compared with the appropriate IgG group. Thus, the antibody treatments employed in C.B-17SCID/bg mice challenged with human fibroblasts markedly altered transcript expression for murine extracellular matrix associated genes.

Immunoneutralization of Human CCR7 or Human CCL21 Significantly Reduced Whole Lung Hydroxyproline Levels in C.B-17SCID/bg Mice that Received Human IIP Fibroblasts:

Hydroxyproline levels in whole lung samples from IgG-, anti-CCL21-, or anti-CCR7-treated control C.B-17SCID/bg mice (i.e. mice that did not receive human fibroblasts) and groups of treated mice that received normal, NSIP, or IPF/UIP fibroblasts were measured. Hydroxyproline levels were increased in whole lung samples from C.B-17SCID/bg mice that received normal fibroblasts and IgG but neither antibody treatment altered these levels. In the NSIP fibroblast C.B-17SCDI/bg groups, hydroxyproline levels were significantly increased above those levels measured in the control C.B-17SCID/bg group, and the anti-CCL21 antibody and anti-CCR7 antibody therapies significantly reduced hydroxyproline levels by 52±6.7 and 51±5.6%, respectively, compared to the IgG treatment group. In the IPF/UIP fibroblast C.B-17SCID/bg group that received IgG, hydroxyproline levels were again significantly increased above those levels measured in the control C.B-17SCID/bg group. In addition, hydroxyproline levels in IPF/UIP fibroblast challenged mice were reduced by 66±7.2 and 59±7.1% in the anti-CCL21 and anti-CCR7 antibody treatment groups, respectively, compared to the IgG treated C.B-17SCID/bg IPF/UIP fibroblast group. Thus, these data confirmed that the targeting of either CCL21 or CCR7 markedly and significantly reduced pulmonary remodeling precipitated by the adoptive transfer of NSIP or IPF/UIP fibroblasts in C.B-17SCID/bg mice.

Whole Lung Cytokine Analysis Showed that Murine CCL21 Levels were Significantly Reduced in the Lungs of C.B-17SCID/bg Mice that Received IPF/UIP Fibroblasts and Anti-CCR7 Antibody Therapy:

Because whole lung levels of murine IL-13, CCL6, and CCL21 were altered and/or increased by the presence of NSIP and IPF/UIP fibroblasts in C.B-17SCID/bg mice, the effects of the IgG and monoclonal antibody treatments on these mediators at day 63 were assessed. The anti-CCR7 and anti-CCL21 antibody therapies did not affect whole lung levels of IL-13 or CCL6 in any of the C.B-17SCID/bg fibroblast groups. However, the anti-CCR7 antibody therapy significantly reduced whole lung levels of murine CCL21 in the C.B-17SCID/bg group that received IPF/UIP fibroblasts compared to the C.B-17SCID/bg group that received IPF/UIP fibroblasts+IgG. Thus, the therapeutic targeting of CCR7 reduced murine CCL21 levels but did not affect the levels of the other two mouse mediators found to be elevated in the IIP fibroblast models.

Discussion.

The present study addressed the following two questions: 1) do adoptively transferred human pulmonary fibroblasts remodel the lung architecture in SCID mice? 2) what role do CCL21 and CCR7 exert in the remodeling response precipitated by the adoptive transfer of human fibroblasts? The response to the first question was affirmative since the i.v. adoptive transfer of either $1 \times 10^6$ IPF/UIP or NSIP fibroblasts into mice C.B-17SCID/bg mice lacking both adaptive and innate immune features caused fibrosis, which was confirmed using histological, molecular, and biochemical analyses. This fibrosis was abrogated by the therapeutic administration of either monoclonal antibodies directed against human CCL21 or CCR7 thereby demonstrating a major role for this ligand and its receptor in pulmonary fibrosis, similar to their roles in renal (Banas et al., J. Immunol., 2002, 168:4301-4307 and liver (Bonacchi et al., Gastroenterology 2003, 125:1060-1076) fibrosis.

Although murine equivalents of known and putative profibrotic mediators were increased in C.B-17SCID/bg mice that had received either IPF/UIP or NSIP fibroblasts, the role of these mediators in the fibrotic process is questionable because their levels were unchanged in many groups of C.B-17SCID/bg mice which showed a significant decrease in lung remodeling. Thus, the present study provides evidence that the adoptive transfer of IIP fibroblasts promotes fibrosis in C.B-17SCID/bg mice and identifies a novel therapeutic target in IIP.

The modeling of clinical pulmonary fibrosis remains a major challenge in the laboratory (Chua et al., Am J. Resp. Cell Mol. Biol., 2005 33:9-13). Although bleomycin sulfate is the agent of choice in the induction of experimental fibrosis, bleomycin-induced pulmonary fibrosis has been criticized as a less than ideal model of IPF/UIP (Chua et al., Am J. Resp. Cell Mol. Biol., 2005 33:9-13). Recognizing that newer models of pulmonary fibrosis should incorporate as many of the features of clinical IIP as possible, the present study capitalized on the observation that the fibroblast is primarily responsible for the profound and often lethal remodeling in these diseases (Zisman et al., Meth. Mol. Med. 2005, 117:3-44). The adoptive transfer of either IPF/UIP or NSIP fibroblasts initiated interstitial remodeling and histologically evident fibrosis was observed at day 35, but no earlier, after the i.v. adoptive transfer of these lines. The delay in appearance of fibrosis is not readily explainable but these findings are consistent with previous studies in which the adoptive transfer of human endothelial cells into C.B-17SCID/bg mice required approximately 30 to 40 days before distinct blood vessels were apparent (Skovseth et al., Am. J. Pathol., 2002, 160: 1629-1637). Thus, the present study highlights that a clinically relevant model of pulmonary fibrosis can be initiated in immunodeficient mice with the adoptive transfer of human pulmonary fibroblasts.

The obvious benefit of the IPF/UIP and NSIP fibroblast C.B-17SCID/bg models described herein is their utility in the testing of novel therapeutics for these diseases. The present study addressed the roles of human CCL21 and CCR7 since we have observed that both are prominently expressed in IIP biopsies (Choi et al., J. Clin. Pathol. 2006, 59:28-39) and cultured IIP fibroblasts. Our present hypothesis is that the therapeutic effect of antihuman CCL21 and anti-human CCR7 antibody treatments relates to their negations of the pro-proliferative effect of CCL21 on IPF/UIP and NSIP fibroblasts. While it is unlikely that the monoclonal antibodies employed herein affected the migration of i.v. injected fibroblasts since the antibody treatments were delayed until a time point when fibrosis was histologically apparent in C.B-17SCID/bg mice, it is conceivable that this therapeutic approach, if employed in other models of pulmonary fibrosis, may have an effect on the recruitment of fibrocytes into the lung. CCR7 is prominently expressed on fibrocytes (Abe et al., J. Immunol., 2001, 166:7556-7563; Hashimoto et al., J. Clin. Invest., 2004 113:243-252) and CCL21 promotes their recruitment into various tissue sites (Abe et al., J. Immunol., 2001, 166:7556-7563). Studies are presently underway to address the role of CCR7-positive fibrocytes in bleomycin-induced pulmonary fibrosis using CCR7 wild type and gene deficient mice.

The precise contribution of the adoptively transferred human IIP fibroblasts and the mouse-associated fibrotic components (i.e. cells and mediators) to the overall pulmonary remodeling response observed in C.B-17SCID/bg mice remains to be determined. In the present study, it would appear that there was an interaction between the transferred human fibroblasts and mouse components as evidenced by the dynamic changes in murine extracellular matrix associated transcripts and murine soluble profibrotic proteins in the lungs of C.B-17SCID/bg mice that most notably received either of the two IIP fibroblast types. While the relative importance of the soluble murine proteins detected in the C.B-17SCID/bg fibrotic response is questionable at this point, the alterations in cathepsin E, MMPs, extracellular matrix components (i.e. collagen and fibronectin), and the inhibitors of MMPs in the IIP fibroblast C.B-17SCID/bg groups relative to the normal fibroblast C.B-17SCID/bg group may indicate that the mouse-associated fibrotic components were actively involved in the remodeling response. Quantitative TAQMAN PCR confirmed that collagen 1, cathepsin E, MMP-19, and TIMP-1 transcript levels were significantly increased in the IIP fibroblast C.B-17SCID/bg groups relative to changes transcript levels for these genes in C.B-17SCID/bg mice that received normal fibroblasts. These transcript changes are relevant to clinical pulmonary fibrosis since cathepsins (Kimura et al., J. Med. Invest 2005, 52:93-100; Wattiez at al., Electrophoresis 2000, 21: 2703-2712) MMPs and TIMPs (reviewed in Pardo et al. Proc. Am. Thorac Soc., 2006, 3:383-388), and extracellular matrix (Kuhn and Mason, Am. J. Pathol. 1995; Adachi Am J. Pathol 1988, 133: 193-203) are increased in the more severe forms of IIP such as IPF/UIP and NSIP. MMP-19 was increased most notably in C.B-17SCID/bg mice that received IPF/UIP fibroblasts, and although this proteinase appears to have a major role in dermal wound healing responses (commentary by Mauch J. Invest. Dermatol. 2003, 121), its role in pulmonary fibrosis is unknown. Almost without exception, the anti-CCL21 and anti-CCR7 antibody therapies reduced all the above-mentioned murine extracellular matrix-associated gene products analyzed using quantitative TAQMAN PCR. The one exception was MMP-19 and further study of the relative importance of MMP-19 in the pulmonary fibrotic response evoked after the adoptive transfer of human IIP fibroblasts is warranted in light of this and our other findings.

In summary, this example confirms that pulmonary fibrosis can be transferred to C.B-17SCID/bg mice following the i.v. adoptive transfer of either IPF/UIP or NSIP primary fibroblast lines. The utility of this model in the testing of novel therapeutic strategies was demonstrated, and the findings further support the possibility that the CCL21-CCR7 interaction may be an important target in clinical NSIP and IPF/UIP.

Example 5

Idiopathic Pulmonary Fibrosis Fibroblasts Migrate and Proliferate to CC Chemokine Ligand-21

The purpose of this Example was to examine the functional and signaling significance of CCR7 expression of primary fibroblasts grown from IPF/UIP and normal surgical lung biopsies. Primary fibroblasts were cultured from surgical lung biopsies from IPF/UIP and normal patients. Fibroblasts treated with or without CC chemokine ligand (CCL) 21 were analyzed for functional, transcript and proteomic differences using immunocytochemical analysis, gene arrays, Taqman real-time PCR, migration, proliferation and Western Blot assays.

CCR7 was expressed by IPF-UIP, but not normal, fibroblasts. IPF/UIP, but not normal, fibroblasts showed significant migratory and proliferative responses when exposed to CCL21, which were inhibited by pertussis toxin or neutralizing antibodies to CCR7. Exposure of IPF/UIP fibroblasts to CCL21 altered the phosphorylation status of MEK 1/2, ERK 1/2, and p90RSK in these cells, which were abrogated by pertussis toxin or CCR7-specific small interfering RNA. Together, these data confirm that CCL21 modulates the functional properties of IPF/UIP, but not normal, fibroblasts.

Given the interstitial expression of CCR7 in IIP SLBs, the inventors believed that this chemokine receptor may be expressed and functionally active in SLB-derived primary fibroblasts. In the present study, migratory and proliferation activities were observed in IPF/UIP, but not normal fibroblasts, exposed to CCL21. The exposure of IPF/UIP fibroblasts to CCL21 led to altered phosphorylation of proteins associated with extracellular signal regulated kinase (ERK 1/2) signaling pathway in IPF/UIP fibroblasts, which was blocked by pertussis toxin or CCR7 siRNA. Thus, these data demonstrate that IPF/UIP fibroblasts are responsive to CCR7-dependent activation, making CCR7 an attractive target in IPF/UIP.

Patients:

All patients underwent clinical evaluation, including chest radiography, lung function measurements, and thin-section computed tomography before fiberoptic bronchoscopy. In these patients, a suspicion of IIP was determined from a compilation of symptoms, physiological symptoms, and radiographical findings. None of the patients enrolled in the present study had undergone previous biopsy surgery or received therapy for IIP. SLBs were obtained via the Clinical Core associated with the IIP Specialized Center of Research at the University of Michigan Medical School from patients suspected of having UIP or NSIP between May 2000 and May 2003. SLBs were obtained from at least two lobes (normally on the left side) in all patients undergoing diagnostic SLB for IIP as previously described in detail. Histologically normal lung was obtained from resected specimens in patients undergoing thoracic resection. Each biopsy was processed separately using sterile technique in a laminar flow hood and processed for the culture of primary fibroblast lines (see below).

Fibroblast Isolation and Culture:

Fibroblasts were mechanically dissociated and cultured from IPF/UIP or histologically normal SLBs as previously described (Hogaboam et al., Meths. Mol. Med., 2005, 117: 209-221).

Protein collection and RNA Extraction:

Primary fibroblasts were plated in 12-well tissue culture plates at $2.5 \times 10^5$ cells/ml and allowed to adhere overnight. Fibroblasts were washed once with PBS. 500 µl of Dulbeco's modified Eagle's medium with 0.5% FBS (DMEM-0.5) alone or with 10 ng/ml CCL19 or CCL21 recombinant proteins were added to quadruplicate wells for 24 hours. Cell-free supernatants were collected and stored at −80° C. until assayed for soluble protein content. After removal of supernatants, 250 µl of Trizol was added to each well and RNA was extracted according to manufacturer's directions (Invitrogen, Carlsbad, Calif.).

Antibodies:

Western antibodies include: Monoclonal Anti-human CCR7 antibody (R&D systems. Minneapolis, Minn.), Phospo-p44/42 Map Kinase (Thr202/Tyr204), Phospho-MEK1/2 (Ser217/221), Phospho-p90RSK (Thr573), Phospho-SEK1/MKK4 (Ser257/Thr261), Phospho-SAPK/JNK (Thr183/Tyr185), Phospho-c-Jun (Ser63) II, Phospho-p38 MAP Kinase (Thr180/Tyr182), Phospho-MKK3/MKK6 (ser189/207) (all Cell Signaling, Danvers, Mass.), Anti-beta Actin, Anti-GAPDH, Rabbit polyclonal to alpha smooth muscle actin (Abcam, Cambridge, Mass.). Secondary antibodies used were: Anti-rabbit, HRP conjugated, Anti-mouse, HRP conjugated, anti-biotin, HRP conjugated (Cell Signaling, Danvers, Mass.).

Gene Arrays:

Human CCR7, CCL19, and CCL21 gene expression was analyzed using a specific chemokine and chemokine receptor gene array from SuperArray. (Carlsbad, Calif.).

TAQMan Analysis:

CCR7 and GAPDH expression were analyzed in IPF/UIP and normal fibroblasts by real-time quantitative RT-PCR procedure using a 7500 Real Time PCR System (Applied Biosystems, Foster City, Calif.) as previously described (19). All antibodies and probes were purchased from Applied Biosystems (Foster City, Calif.). CCR7 expression was normalized to GAPDH before the fold change in expression was calculated.

Immunocytohistochemistry:

Human CCR7 protein expression was analyzed through immunocytochemistry using HRP-AEC Cell and Tissue staining kit according to manufacturer's instructions (R & D Systems, Minneapolis, Minn.).

Fibroblast Migration Assay.

Primary IPF/UIP and normal fibroblasts were added to 8 µm transwell inserts in 6-well cell culture plates in the presence or absence of 10 ng/ml CCL19 or CCL21 for 24 hours. Migrated fibroblasts in bottom well were fixed and stained with hemotoxylin and counted. To test for receptor or ligand specificity, 5 µg/ml anti-human CCR7, CCL19, or CCL21 antibodies were added to each well. As a control, 5 µg/ml IgG or 10 µl PBS was added.

Proliferation Assay:

Proliferative ability of the fibroblasts was assessed in 24-well tissue culture plates using [$^3$H]thymidine incorporation as previously described (9).

Sircol Collagen Assay:

Soluble collagen content was determined using a Biocolor Sircol collagen assay (Accurate Chemical & Scientific Corp, Westbury, N.Y.). For the assay, 100 µl of cell-free supernatant samples were added to 1 ml of Sircol Dye and shaken at room temperature for 30 minutes. The tubes were then centrifuged for 10 minutes at 10,000×g. The dye removed and 1 ml Alkaline solution added to each tube and mixed thoroughly. To read the assay, 200 µl of each solution was transferred to a 96-well optical flat-bottom plate along with 200 µl of standards. The plate was then read at 540 nm using a plate reader and the concentrations normalized to total protein as determined by Bradford assay.

Bioplex Protein Assay:

Cell-free supernatant samples were analyzed for human RANTES/CCL5 using an Extracellular Antibody kit (Invitrogen BioSource, Carlsbad, Calif.) and a Bio-Rad Luminex Bio-Plex 200 System (Hercules, Calif.). In short, 50 µl cell-free supernatant samples and standards were incubated with 50 µl multiplex beads for 30 minutes on a shaker. The beads were washed 3 times with 100 µl wash buffer and then incubated with 25 µl detection antibody solution for 30 min on a shaker. After washing 3 more times, streptavidin-PE was added and the beads were incubated 10 minutes on a shaker and washed 3 more times. The beads were then resuspended in assay buffer and read using the above system.

Western Blot Analysis:

Fibroblasts were plated at $5 \times 10^5$ cells/well in six well plates and allowed to adhere overnight. The fibroblasts were then starved 24 hours in serum free DMEM. The fibroblasts were treated with 0.5% fetal bovine serum in DMEM alone or with 10 ng/ml CCL19 or CCL21 recombinant proteins for 0.5, 2, 5 and 30 minutes. Some fibroblasts were exposed to 200 nM Pertussis Toxin (Sigma, St. Louis, Mo.) 2 hours prior to treatment. The fibroblasts were then washed with ice-cold phosphate-buffered saline and then lysed in 500 µl of ice-cold lysis buffer consisting of 1% Triton X-100, 50 mM NaF, 2 mM EDTA, 0.15 M NaCl, 0.01 M Sodium Phophate, 200 µM Sodium Orthovanadate, 5 µg/mL pepstatin, 5 µg/mL Leupeptin and 100 nM calyculin. After incubating 5 minutes on ice, the fibroblast lysates were scraped and transferred to tubes. The total protein content was determined by Bradford assay. Samples containing 20 µg of total protein were mixed with 4 µl of 4×LDS sample buffer (Invitrogen, Carlsbad, Calif.) and double deionized water (ddH2O), boiled at 90° C. for 5 minutes and then separated by SDS-PAGE in a 4-12% NuPage Bis-Tris gels (Invitrogen, Carlsbad, Calif.). The proteins were transferred to nitrocellulose membranes (Invitrogen, Carlsbad, Calif.). After blocking in 5% NFDM in 1×TBS/T, the membranes were blotted for primary phospho-antibodies, stripped (Restore™ Western Blot Stripping Buffer, Pierce, Rockford, Ill.), washed, and re-blotted for GAPDH, a loading control.

Transfection of siRNA:

To block the expression of CCR7, small interfering RNA (siRNA) were created using the Qiagen custom synthesis site. The effectiveness of two siRNA candidates was tested through transfection with Lipofectamine 2000 (Invitrogen, Carlsbad, Calif.) into IPF/UIP lung fibroblasts and analyzed using Taqman analysis for CCR7. The more efficient siRNA (approximately 70% knockdown, AGCGGACATCAGCTGGTCAA) was used for western blot analysis of Erk 1/2 pathway phosphorylation.

CCR7, CCL19, and CCL21 Gene Expression were Present Infibroblasts Grown from Normal and IPF/UIP SLBs.

Three normal and three IPF/UIP SLB-derived fibroblasts lines were subjected to RNA analysis using a specific human chemokine and chemokine receptor SuperArray. This analysis revealed that CCR7, CCL19, and CCL21 were present in both groups, but CCR7 expression was significantly higher in the IPF/UIP lines compared with the normal fibroblast lines. Further analysis of gene expression using TAQMAN real-time PCR confirmed the presence of transcripts for CCR7, CCL19, and CCL21 in all fibroblasts lines used in this study. Thus, these data demonstrated that CCR7, CCL19, and CCL21 gene transcripts were present in normal and IPF/UIP fibroblasts.

Marked CCR7 Protein Expression was Present in IPF/UIP Fibroblasts but not Normal Fibroblasts.

The inventors have shown that nearly 100% of UIP SLBs, exhibited a combination of focal and diffuse CCR7 protein expression in interstitial areas. Also, the focal areas of CCR7 appeared to coincide with histologically distinct fibroblastic foci. To determine whether primary fibroblasts grown from normal and IPF/UIP SLBs expressed CCR7, immunocytochemical staining for CCR7 was performed. IPF/UIP fibroblasts were strongly positive for CCR7 whereas normal fibroblasts expressed little or no CCR7.

CCL21 Directed the Migration of IPF/UIP but not Normal Fibroblasts.

CCR7 expression is upregulated on mature dendritic cells thereby allowing these cells to migrate to the lymph nodes for immune activation (Sozzani et al., J. Immunol., 1998, 161(3): 1083-1086)). On certain breast tumor ((Muller et al., Nature, 2001, 410(6824):50-56) cells and melanoma (Murakam et al., J. Dermatol. Sci., 2004, 36(2):71-78) cells, the interaction between CCR7 and CCL21 has been shown to be important in metastasis. In the present study, both CCL19 and CCL21 promoted the migration of IPF/UJP but not normal fibroblasts. However, CCL21 was the more potent inducer of IPF/UIP fibroblast migration, enhancing the migration of these cells by approximately 7-fold above that observed in IPF/UIP fibroblast cultures exposed to DMEM alone. To determine whether this migration was CCR7 dependent, one of IgG, anti-human CCR7, or anti-human CCL21 antibody (all at 5 µg/ml) was added to triplicate wells. While the presence of IgG did not alter the migration of IPF/UIP fibroblasts, the presence of anti-CCR7 or anti-CCL21 antibodies significantly inhibited the migratory response of IPF/UIP fibroblasts. Pretreating the fibroblasts with 200 ng/ml Pertussis Toxin also inhibited the CCL21-induced migratory response in IPF/UIP fibroblasts. Thus, these data indicated that CCR7 activation promoted the migration of IPF/UIP, but not normal fibroblasts.

CCR7 Activation Stimulated the Proliferation of Primary IPF/UIP Fibroblasts.

IPF/UIP is characterized by severe alveolar and interstitial scarring of the lung due, in part, to extensive fibroproliferation. The enhanced proliferative response of IPF/UIP fibroblast lines was observed in the present study in which all three IPF/UIP lines exhibited a baseline (i.e. DMEM alone) proliferation rate that was approximately 3-fold higher than the normal fibroblasts lines studied. In addition, the addition of CCL21, but not CCL19, at 10 ng/ml significantly increased the proliferative properties of all three primary IPF/UIP fibroblast lines above that observed in cultures exposed to DMEM alone. The proliferative properties of normal fibroblasts were not altered by the presence of either CCL19 or CCL21.

CCR7 Activation Promoted CCL5 but not De Novo Collagen Generation by Primary IPF/UIP Fibroblasts.

Previous studies have shown that chemokines may drive the expression of other chemokines in various cell types. For example, the addition of CCL5 to cultures of IPF/UIP fibroblasts significantly enhanced the expression of CCL7, a putative biomarker in IPF/UIP. To determine whether CCR7 activation via CCL21 altered the chemokine generating properties of IPF/UIP and normal fibroblasts, both groups of fibroblasts were exposed to CCL21 for 24 h prior to soluble multiplex protein analysis. CCL5 was present in cultures of IPF/UIP and normal fibroblasts, and CCL21 significantly increased CCL5 levels in IPF/UIP, but not normal fibroblasts. Surprisingly, the presence of CCL21 in cultures of IPF/UIP fibroblasts for 24 h did not alter their synthesis of soluble collagen, as determined using a Sircol collagen assay. This data, taken with the data from prior studies indicates that CCR7 activation enhanced the chemokine synthetic capabilities of IPF/UIP fibroblasts.

Expression of Alpha Smooth Muscle Actin (αSMA) was not Altered by CCL21 in Primary IPF/UIP and Normal Fibroblasts.

αSMA is a protein marker for a highly synthetic fibroblast subtype known as myofibroblasts (White et al., Am. J. Respir. Crit. Care Med., 2006, 173(1): 112-1121). Given the profound effects of CCL21 on the synthesis of chemokines by IPF/UIP fibroblasts we next addressed whether CCR7 ligands altered the expression of αSMA in these cells. Western blot analysis showed that cultures of IPF/UIP fibroblasts expressed higher levels of αSMA than cultures of normal fibroblasts consistent with the higher synthetic properties of the IPF/UIP cells. However, αSMA expression was not affected by the presence of CCL21. Although αSMA-positive IPF/UIP fibroblasts expressed CCR7 (based on immunocytochemical analysis), the addition of CCL21 to these cells did not appear to further enhance the level of this protein suggesting that CCR7 activation was not a major stimulus for fibroblast differentiation into myofibroblasts.

P44/p42 Extracellular Signal-Related Kinase (ERK 112) Signaling Pathway in IPF/UIP Fibroblasts was Activated Following CCR7 Activation by CCL21.

Many important cell functions are regulated by a group of signaling proteins collectively referred to as the mitogen-activated protein kinase (MAPK) pathways. Each pathway has an unique effect on cell cycle, growth, and migration due in part to the fact that each pathway is activated by distinct stimuli including growth factors, stress, and inflammatory cytokines. The cascade of activation initiated by these stimuli involves the sequential phosphorylation of a MAPKK kinase, a MAPK kinase, and a MAPK. This final step allows a MAPK to enter the nucleus and activate one or several downstream transcription factors thereby leading to biological responses such as cell proliferation, migration, and survival. To determine the effects of activated CCR7 on MAPK pathways, untreated and CCL21-activated fibroblast associated proteins were collected at 30 sec and 2, 5 and 30 minutes, and western blot analysis of the ERK 1/2, p38, and c-Jun N-terminal kinase (JNK) MAPK pathways were analyzed. While there was no change in phosphorylation of signaling proteins associated with the p38 and JNK pathways, the ERK 1/2 pathway showed evidence of phosphorylation changes following CCL21 addition to cultures of IPF/UIP fibroblasts. In addition, there was no evidence of phosphorylation of c-RAF, the MAPKKK of this pathway.

Mitogen-Activated Protein Kinase Kinase (MEK 1/2) was Phosphorylated in IPF/UIP Fibroblasts Following CCL21 Exposure.

Untreated (i.e. serum starved) primary normal and IPF/UIP fibroblast lines did not exhibit constitutively activated MEK 1/2. The addition of DMEM-0.5 alone to normal fibroblasts caused a time-dependent increase in the phosphorylation of MEK 1/2, which peaked at the 5 minutes. However, this phosphorylation profile was unchanged by the presence of 10 ng/ml of CCL21. While the addition of DMEM-0.5 alone promoted a time-dependent activation of MEK1/2 in IPF/UIP fibroblasts with peak activation at 5 minutes, the addition of CCL21 (at 10 ng/ml) resulted in an increase of phosphorylation at 2 and 5 minutes with the level of MEK 1/2 phosphorylation returning to media levels at the 30 min endpoint. Together, these data suggested the accelerated activation of MEK 1/2 in IPF/UIP fibroblasts exposed to CCL21.

CCL21 Accelerated ERK 112 Phosphorylation in IPF/UIP Fibroblasts.

Untreated primary normal and IPF/UIP fibroblasts exhibited constitutive ERK 1/2 phosphorylation, but the baseline activity of this MAPK appeared to be higher in normal fibroblasts compared with IPF/UIP fibroblasts, which showed very little constitutive ERK 1/2 phosphorylation. The addition of DMEM-0.5 alone to normal fibroblasts resulted in peak ERK 1/2 activation at 5 min. A similar pattern of ERK 1/2 activation was observed in cultures of normal fibroblasts exposed to 10 ng/ml of CCL21 added to DMEM-0.5 but the overall levels of ERK 1/2 phosphorylation were lower in these cultures. In cultures of IPF/UIP fibroblasts, the addition of DMEM-0.5 alone produced a pattern of ERK 1/2 phosphorylation similar to that observed in normal fibroblast cultures, however, the magnitude of activation was much higher in IPF/UIP fibroblasts compared to normal fibroblasts. In cultures of IPF/UIP fibroblasts exposed to CCL21 and DMEM-0.5, there was a significant increase in phosphorylation at 2 min compared with the phosphorylation of ERK 1/2 in cultures of these fibroblasts exposed to DMEM-0.5 alone. Due to the low constitutive ERK 1/2 phosphorylation in IPF/UIP fibroblasts, the phosphorylation levels following exposure of these cells to DMEM-0.5 alone or DMEM-0.5+10 ng/ml of CCL21 ranged from 60- to 125-fold higher than cultures containing untreated IPF/UIP fibroblasts.

Ribosomal S6 Kinase (p90RSK) Phosphorylation in IPF/UIP Fibroblasts was Promoted by CCL21.

P90RSK has been shown to be activated by the chemokine CXCL12 in the context of myelopoiesis (Lee et al., 2002, Blood 99(12):4307-4317). Analysis of p90RSK in the present study revealed that this transcription factor (located downstream of ERK 1/2) was present in a phosphorylated state in untreated normal and IPF/UIP fibroblasts. The changes in the activation of p90RSK were similar in cultures of normal fibroblasts regardless of the presence of CCL21. In contrast, the presence of CCL21 in cultures of IPF/UIP fibroblasts at all time points examined enhanced the phosphorylation of this transcription factor approximately 2.5-fold above that observed in untreated cultures. Together, these data indicated that CCR7 was an active receptor in IPF/UIP fibroblasts and this receptor appeared to signal, at least in part, via the ERK 1/2 pathway. Although normal fibroblasts showed activation of the ERK 1/2 pathway, this activation appeared to be independent of the presence of CCL21.

G-Protein Inhibition with Pertussis Toxin or CCR7 Gene Silencing with Small Interfering RNA Attenuated CCL21-Mediated ERK 1/2 Activation.

To confirm the role of CCR7 in IPF/UIP fibroblast activation, additional studies were undertaken to determine whether pertussis toxin (a Gi and Go protein inhibitor) or siRNA-mediated CCR7 gene silencing abolished the effects of CCL21 on ERK 1/2 activation. The addition of a specific CCR7 siRNA reduced the protein expression of this receptor by approximately 70% at 24 h after transfection. This inhibition of CCR7 protein expression persisted for the 30 min duration of these studies. Neither a Lamin A/C specific siRNA nor a random siRNA had any effect on the protein expression of CCR7 in IPF/UIP fibroblasts. Thus, these data showed that CCR7 was successfully targeted in vitro using a specific siRNA. The presence of either pertussis toxin or a CCR7 siRNA in cultures of IPF/UIP fibroblasts reduced MEK 1/2, ERK 1/2, and p90RSK phosphorylation to levels observed in cultures exposed to DMEM-0.5 alone Several studies have documented that primary human lung fibroblasts exhibit profibrotic activation in response to (Atamas et al., Am. J. Respir. Cell Mol. Biol., 2003, 29(6):743-9; Keane et al., J. Immunol., 1997, 159(3):1437-1443; Prasse et al., Am. J. Respir. Crit. Care Med., 2006, 173(7)781-792; Puxeddu et al., J. Allergy Clin. Immunol., 2006, 117(1):103-110) and are a robust source of (Keane et al., J. Immunol., 1997, 159(3): 1437-1443; Prasse et al., Am. J. Respir. Crit. Care Med., 2006, 173(7)781-79) chemokines.

The present study addressed the role of CCR7 expression by primary IPF/UIP fibroblasts derived from SLBs taken at the time of disease diagnosis. In contrast to primary normal fibroblasts derived from the normal margins of resected lung tumors, IPF/UIP fibroblasts and αSMA-positive myofibroblasts expressed CCR7, a receptor that is thought to be restricted to cells of hematopoietic origin. The activation of CCR7, via CCL21 more so than CCL19, promoted and/or significantly augmented the migration, proliferation and chemokine synthetic properties of IPF/UIP fibroblasts. Exogenous CCL21 through a CCR7-dependent manner activated the ERK 1/2 MAPK pathway. Thus, this study suggests that IPF/UIP fibroblasts acquire the ability to respond to CCR7 ligands, which are abundantly expressed in the lung regardless of disease status (Choi et al., J. Clin. Pathol., 2006 59(1): 28-39), and this responsiveness may have a major role in the excessive fibroproliferation that characterizes IPF/UIP.

In summary, this example shows that primary human fibroblasts derived from IPF/UIP SLBs express functional CCR7. Activation of CCR7 by its ligands, particularly CCL21, induced migration, proliferation and chemokine synthesis in IPF/UIP fibroblasts. CCL21-induced activation through CCR7 was G-protein dependent, and involved the activation of the ERK 1/2 MAPK pathway. Given this data and other evidence that targeting CCL21 inhibits experimental glomerular (Banas et al., J. Immunol., 2002, 168(9):4301-4307) and hepatic (Bonacchi et al. Gastroenterology, 2003, 125(4): 1060-1076) scarring, it is thought that CCR7 represents a novel target in IPF/UIP. Further, the data showed that CCL21-induced MEK 1/2, ERK 1/2, and p90RSK phosphorylation was dependent upon a functional G-protein coupled signaling events and CCR7.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps."

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. More specifically, it will be apparent that certain agents which are both chemically and physiologically related may be substituted for the agents described herein while the same or similar results are achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A method of treating pulmonary fibrosis in a mammal comprising decreasing the activity of CCL21 in the fibrocytes and/or fibroblasts present at a fibrotic lesion in pulmonary fibrosis, disorder wherein said decreasing the activity of CCL21 comprises administering an anti-CCL21 antibody that inhibits CCL21 in said fibroblasts, in an amount effective to alleviate one or more symptoms of pulmonary fibrosis.

2. The method of claim 1, wherein the method further comprises decreasing the activity of CCL19 in the fibroblasts associated with said pulmonary fibrosis comprising administering an anti-CCL19 antibody.

3. The method of claim 1, wherein said decreasing the activity of CCL21 comprises administering an anti-CCL21 antibody that decreases the expression of CCL21 in said fibroblasts, in an amount effective to alleviate one or more of the symptoms of pulmonary fibrosis.

4. The method of claim 1 comprising administering said antibody locally to the site of a fibrosing lesion.

5. The method of claim 4, wherein said fibrosing lesion is in a lung and said antibody is contacted locally with said lesion.

6. The method of claim 1 wherein said antibody comprises a targeting moiety to specifically locate said agent to the site of a fibrosing lesion.

7. The method of claim 1 wherein said antibody is administered using a mode of administration selected from the group consisting of topical administration, injection, inhalation, continuous release by depot or pump, or any combinations thereof.

8. A method of inhibiting fibroblast and/or fibrocyte proliferation in a patient with pulmonary fibrosis comprising contacting said fibroblast and/or fibrocyte with a composition that comprises an anti-CCL21 antibody.

9. The method of claim 8, further comprising contacting said fibroblast with a composition that comprises an anti-CCL19 antibody.

10. The method of claim 8 or 9, further comprising contacting said fibroblast with a composition that comprises an anti-CCR7 antibody.

11. The method of claim 8 wherein said fibrocytes and/or fibroblasts are located in vitro.

12. The method of claim 8 wherein said fibrocytes and/or fibroblasts are located in vivo.

13. The method of claim 8 wherein said fibrocytes and/or fibroblasts are located in vivo in lung tissue.

14. A method of inhibiting the migration of fibrocytes and/or activation of fibroblasts in a patient with pulmonary fibrosis comprising contacting said fibrocytes and/or fibroblasts with a composition comprising an anti-CCL21 antibody that inhibits that activity of CCL21, wherein said fibrocytes are located in vivo in a mammal and said method inhibits migration of fibrocytes to lung tissue in said mammal and prevents excessive production of extracellular matrix.

15. The method of claim 14 wherein said fibroblasts are resident pulmonary fibroblasts located in lung tissue in a mammal and said method inhibits activation of said fibroblasts in the lung tissue in said mammal, thereby preventing the excessive production of extracellular matrix.

16. A method of treating pulmonary fibrosis comprising inhibiting the migration of fibrocytes and/or the activation of resident pulmonary fibroblasts located in lung tissue in a subject suffering from fibrotic pulmonary disease comprising administering to said subject an anti-CCL21 antibody that inhibits the activity or expression of CCL21 in said fibrocytes and/or said fibroblasts thereby preventing the excessive production of extracellular matrix and ameliorating the symptoms of pulmonary fibrosis.

17. A method of treating or inhibiting the development of radiation-induced pulmonary laminitis and/or radiation induced pulmonary fibrosis in a subject comprising administering to said subject an anti-CCL21 antibody that decreases the presence or activity of CCL21 in the fibrocytes and/or fibroblasts in the pulmonary tissue of said subject, wherein said antibody is administered prior to, and/or during, and/or after the administration of radiation therapy.

18. The method of claim 17, wherein the method further comprises administering an anti-CCL19 antibody that decreases the presence or activity of CCL19 in the fibroblasts associated with said pulmonary fibrosis.

19. A method of treating or inhibiting the development of drug-induced pulmonary fibrosis in a subject comprising administering to said subject an anti-CCL21 antibody that decreases the presence or activity of CCL21 in the fibrocytes and/or fibroblasts in the pulmonary tissue of said subject, wherein said antibody is administered prior to, and/or during, and/or after the administration of the drug.

20. The method of claim 19 wherein the method further comprises administering an anti-CCL19 antibody that decreases the presence or activity of CCL19 in the fibroblasts associated with said pulmonary fibrosis.

21. The method of 19, wherein said drug is selected from the group consisting of a cytotoxic agent, an antibiotic, an antiarrhythmic agent, an anti-inflammatory agent, and an illicit drug.

22. The method of claim 19, wherein said drug is selected from the group consisting of Amphotericin B, bleomycin, bromocriptine, busulfan, carbamazepin, chlorambucil, cocaine, cyclophosphamide, diphenylhydantoin, ergotamine, flecainide, heroin, melphalan, methadone, methotrexate, methylphenidate, methylsergide, mineral oil, nitrofurantoin, nitrosureas, procarbazine, silicone, sulfasalazine tocainide, and the vinca alkaloid class of agents.

23. The method of any of claims 16 through 22 wherein said anti-CCL21 antibody is administered in combination with corticosteroid, an immunosuppressive agent, an anticoagulant, a diuretic, a cardiac glycoside, a calcium channel blocker, a vasodilator, a prostacyclin analogue, an endothelin antagonist, a phosphodiesterase inhibitors, a beta-2 agonist, an antimuscarinic agent, an endopeptidase inhibitor, a lipid lowering agent and thromboxane inhibitors, or combinations thereof.

* * * * *